United States Patent
Lang et al.

(10) Patent No.: US 10,106,608 B2
(45) Date of Patent: Oct. 23, 2018

(54) IMMUNOSTIMULATORY ANTI-CEACAM1 ANTIBODY

(71) Applicants: UNIVERSITAET DUISBURG-ESSEN, Essen (DE); Karl Sebastian Lang, Essen (DE); Bernhard Singer, Essen (DE); Vishal Khairnar, Essen (DE); Vikas Duhan, Essen (DE)

(72) Inventors: Karl Sebastian Lang, Essen (DE); Bernhard Singer, Essen (DE); Vishal Khairnar, Essen (DE); Vikas Duhan, Essen (DE); Fan Steven Zhou, Essen (DE)

(73) Assignee: UNIVERSITAET DUISBURG-ESSEN, Essen (DE)

(*) Notice: Subject to any disclaimer, the term of this patent is extended or adjusted under 35 U.S.C. 154(b) by 0 days.

(21) Appl. No.: 15/221,612

(22) Filed: Jul. 28, 2016

(65) Prior Publication Data

US 2017/0051058 A1   Feb. 23, 2017

Related U.S. Application Data

(63) Continuation-in-part of application No. PCT/EP2016/051708, filed on Jan. 27, 2016.

(30) Foreign Application Priority Data

Jan. 28, 2015 (DE) ........................ 10 2015 201 479

(51) Int. Cl.
| | |
|---|---|
| G01N 33/53 | (2006.01) |
| C07K 16/00 | (2006.01) |
| C07H 21/04 | (2006.01) |
| C07K 16/28 | (2006.01) |
| A61K 38/17 | (2006.01) |
| A61K 39/095 | (2006.01) |
| A61K 39/102 | (2006.01) |
| A61K 39/104 | (2006.01) |
| C12N 5/0783 | (2010.01) |

(52) U.S. Cl.
CPC ........ *C07K 16/2803* (2013.01); *A61K 38/177* (2013.01); *A61K 39/095* (2013.01); *A61K 39/102* (2013.01); *A61K 39/1045* (2013.01); *C12N 5/0638* (2013.01); *C07K 2317/24* (2013.01); *C07K 2317/565* (2013.01); *C07K 2317/75* (2013.01); *C07K 2317/76* (2013.01); *C07K 2317/92* (2013.01); *C07K 2319/30* (2013.01); *C12N 2501/58* (2013.01)

(58) Field of Classification Search
None
See application file for complete search history.

(56) References Cited

U.S. PATENT DOCUMENTS

| | | |
|---|---|---|
| 8,598,322 B2 | 12/2013 | Markel et al. |
| 2006/0014222 A1 | 1/2006 | Kingsman et al. |
| 2011/0189181 A1 | 8/2011 | Utku et al. |
| 2012/0141470 A1* | 6/2012 | Blumberg ........ C07K 14/70596 424/133.1 |
| 2014/0271618 A1 | 9/2014 | Markel et al. |
| 2014/0328841 A1 | 11/2014 | Blumberg et al. |
| 2015/0225457 A1* | 8/2015 | Blumberg .......... C07K 16/2803 424/134.1 |
| 2015/0273056 A1 | 10/2015 | Blumberg et al. |

FOREIGN PATENT DOCUMENTS

| | | |
|---|---|---|
| DE | 10 2010 024 636 A1 | 12/2011 |
| WO | WO 01/36486 A2 | 5/2001 |
| WO | WO 2005/058358 A2 | 6/2005 |
| WO | WO 2013/054331 A1 | 4/2013 |
| WO | WO 2013/082366 A1 | 6/2013 |
| WO | WO 2014/022332 A1 | 2/2014 |
| WO | WO 2014/059251 A1 | 4/2014 |

OTHER PUBLICATIONS

Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*

MacCallum et al. Antibody-antigen interactions: contact analysis and binding site topography. J. Mol. Biol., 262, 732-745, 1996. Year: 1996).*

Casset et al. A peptide mimetic of an anti-CD4 monoclonal antibody by rational design. Biochemical and Biophysical Research Communications, 307:198-205, 2003. (Year: 2003).*

Paul, Fundamental Immunology, 3rd Edition, 1993, pp. 292-295. (Year: 1993).*

Rudikoff et al Single amino acid substitution altering antigen-binding specificity. Proc Natl ACad SCi U S A. Mar. 1982;79(6):1979-83 (Year: 1982).*

A. Donda et al.: "Locally inducible human CD66a (CEACAM1) as an amplifier of the human intestinal T cell response", Eur. J. Immunol., vol. 30, pp. 2593-2603 (2000).

R. Kammerer et al.: "Biliary glycoprotein (CD66a), a cell adhesion molecule of the immunoglobulin superfamily, on human lymphocytes: structure, expression and involvement in T cell activation", Eur. J. Immunol., vol. 28, pp. 3664-3674 (1998).

"Anti-mouse CD66a (CEACAM1) PE", affymetrix eBioscience, J Immunol., vol. 166, No. 11 pp. 1-2 (2001).

B. C. Turner et al.: "Receptor-Dependent Coronavirus Infection of Dendritic Cells", Journal of Virology, vol. 78, No. 10pp. 5486-5490 (2004).

(Continued)

*Primary Examiner* — Maher M Haddad
(74) *Attorney, Agent, or Firm* — Norman B. Thot

(57) ABSTRACT

An anti-CEACAM1 antibody includes at least one antibody heavy chain ($V_H$) domain having antigen binding sites $CDR1^H$, $CDR2^H$ and $CDR3^H$, and at least one antibody light chain ($V_L$) domain having antigen binding sites $CDR1^L$, $CDR2^L$ and $CDR3^L$. The antigen binding site $CDR2^H$ has a sequence homology of at least 80% to the amino acid sequence WINTYTGEPT (SEQ ID No. 21).

8 Claims, 15 Drawing Sheets

Specification includes a Sequence Listing.

(56) References Cited

OTHER PUBLICATIONS

K. Nakagaki et al.: "Receptor-Independent Spread of a Highly Neurotropic Murine Coronavirus JHMV Strain from Initially Infected Microglial Cells in Mixed Neural Cultures", Journal of Virology, vol. 79, No. 10, pp. 6102-6110 (2005).

A. G. Tietjens: „Initiale Schritte der Hepatitis C Virus Infektion: Evaluation mit verschiedenen Modellsystemen, Dissertation, English Abstract, pp. 1-155 (2008).

M. Kellich: „Die funktionelle Bedeutung der Interaktion von löslichem CEACAM8 und CEACAM1 auf naiven B-Zellen und aktivierten Lymphozyten, Dissertation, English Abstract, pp. 1-105 (2013).

G. Greicius et al.: "CEACAM1 is a potent regulator of B cell receptor complex-induced activation", Journal of Leukocyte Biology, vol. 74, pp. 126-134 (2003).

D. M. Blau et al.: "Targeted Disruption of the *Ceacam1* (MHVR) Gene Leads to Reduced Susceptibility of Mice to Mouse Hepatitis Virus Infection", Journal of Virology, vol. 75, No. 17, pp. 8173-8186 (2001).

Q. Yu et al.: "Association of *Neisseria gonorrhoeae* Opa$_{CEA}$ with Dendritic Cells Suppresses Their Ability to Elicit an HIV-1-Specific T Cell Memory Response", PLOS ONE, vol. 8, Issue 2, No. e56705, pp. 1-13 (2013).

H. Adler et al.: "Perturbation of Lytic and Latent Gammaherpesvirus Infection in the Absence of the Inhibitory Receptor CEACAM 1", PLOS ONE, vol. 4, Issue 7, No. e6317, pp. 1-12 (2009).

S. D. Gray-Owen et al.: "CEACAM1: contact-dependent control of immunity", Nature Reviews Immunology, vol. 6, pp. 433-446 (2006).

I. D. Weiss et al.: "IFN-γ Treatment at Early Stages of Influenza Virus Infection Protects Mice from Death in a NK Cell-Dependent Manner", Journal of Interferon and Cytokine Research, vol. 30, No. 6, pp. 439-449 (2010).

M. Gencheva et al.: "Regulation of CEACAM1 transcription in human breast epithelial cells", BMC Molecular Biology, vol. 11, No. 79, pp. 1-14 (2010).

B. B. Singer et al.: "Carcinoembryonic Antigen-Related Cell Adhesion Molecule 1 Expression and Signaling in Human, Mouse, and Rat Leukocytes: Evidence for Replacement of the Short Cytoplasmic Domain Isoform by Glycosylphosphatidylinositol-Linked Proteins in Human Leukocytes", The Journal of Immunology, vol. 168, pp. 5139-5146 (2002).

Z. Chen et al.: "Editorial: CEACAM1: fine-tuned for fine-tuning", Journal of Leukocyte Biology, vol. 86, pp. 195-197 (2009).

E. O. Lobo et al.: "Pivotal advance: CEACAM1 is a negative coreceptor for the B cell receptor and promotes CD19-mediated adhesion of B cells in a PI3K-dependent manner", Journal of Leukocyte Biology, vol. 86, pp. 205-218 (2009).

K. Fink et al.: "Early type I interferon-mediated signals on B cells specifically enhance antiviral humoral responses", Eur. J. Immunol., vol. 36, pp. 2094-2105 (2006).

M. Battegay et al.: "Quantification of lymphocytic choriomeningitis virus with an immunological focus assay in 24- or 96-well plates", Journal of Virological Methods, vol. 33, pp. 191-198 (1991).

M. Recher et al.: "B cell-intrinsic deficiency of the Wiskott-Aldrich syndrome protein (WASp) causes severe abnormalities of the peripheral B-cell compartment in mice", Blood, vol. 119, No. 12, pp. 2819-2828 (2012).

\* cited by examiner

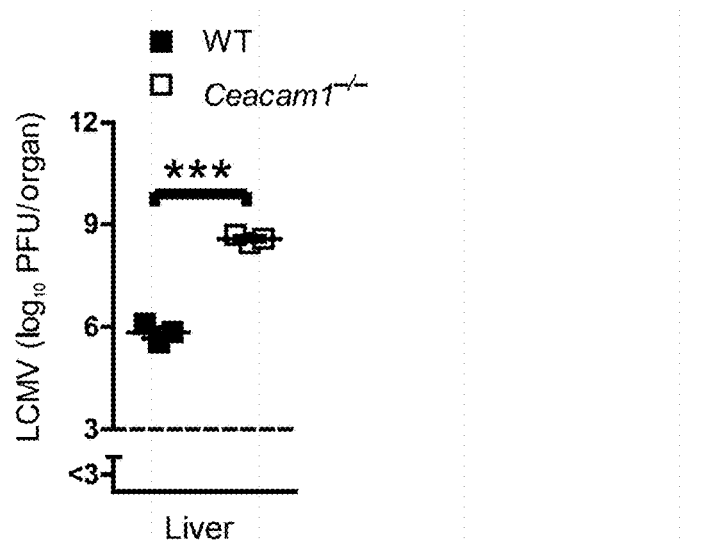
Figure 7 B
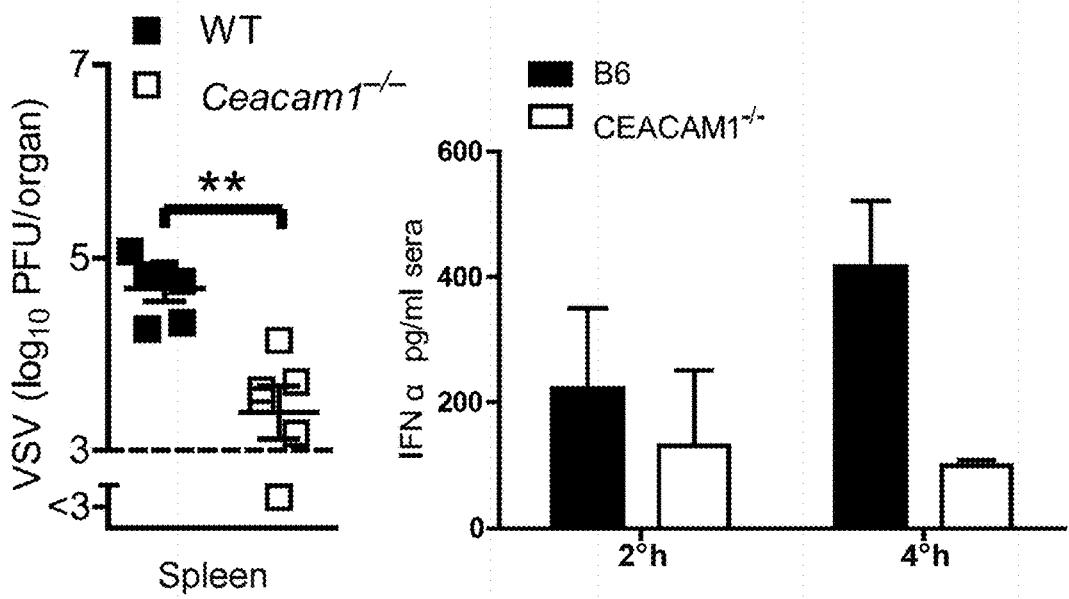
Figure 8 A
Figure 8 B

IMMUNOSTIMULATORY ANTI-CEACAM1 ANTIBODY

CROSS REFERENCE TO PRIOR APPLICATIONS

This application is a continuation in part of International Patent Application No. PCT/EP2016/051708, filed on Jan. 27, 2016, which claims priority to German Patent Application No. 10 2015 201 479.7, filed on Jan. 28, 2015. The entire disclosure of both applications is incorporated by reference herein. The International Application was published in German on Aug. 4, 2016 as WO 2016/120331 A1 under PCT Article 21(2).

FIELD

The present invention relates to substances for use in the therapy or diagnosis of neoplasias, (viral) infections, infectious diseases and/or T- and/or B-cell-dependent diseases, drugs and diagnostic agents, antibodies, variable antibody heavy chain ($V_H$) domains, variable antibody light chain ($V_L$) domains, isolated nucleic acids, B cell lines and a method for producing antibodies.

SEQUENCE LISTING

The Sequence Listing associated with this application is filed in electronic form via EFS-Web and is hereby incorporated by reference into this specification in its entirety. The name of the text file containing the Sequence Listing is Sequence_Listing_DUIS1601_Corrected. The size of the text file is 52,491 Bytes, and the text file was created on Oct. 21, 2016.

BACKGROUND

Carcinoembryonic antigen-related cell adhesion molecule 1 (CEACAM1) is a human glycoprotein which is also known under the name CD66a (Cluster of Differentiation 66a). It belongs to the "carcinoembryonic antigen" gene family. This family includes two subgroups, namely the subgroup of cell adhesion molecules, which include CEACAM1, and also the subgroup of the pregnancy-specific glycoproteins.

It is known that CEACAM1 is a specific cell-cell adhesion molecule which is present on leucocytes, epithelial cells and endothelial cells. Cells that express CEACAM1 on their surface, however, also release it into the blood stream. The glycoprotein mediates the cell adhesion by means of homophilic or heterophilic binding to other proteins of the cell adhesion molecule subgroup.

It is further known that diverse cell activities such as, for example, differentiation and the arrangement of three-dimensional tissue structures, angiogenesis, apoptosis, tumor suppression and metastasis, can be influenced by CEACAM1.

The publication by Singer et al. ("Adhesion Molecule 1 Expression and Carcinoembryonic Antigen-Related Cell Signaling in Human, Mouse, and Rat Leukocytes: Evidence for Replacement of the Short Cytoplasmic Domain Isoform by Glycosylphosphatidylinositol-Linked Proteins in Human Leukocytes", Bernhard B. Singer, Inka Scheffrahn, Robert Heymann, Kristmundur Sigmundsson, Robert Kammerer and Björn Öbrink, The Journal of Immunology (2002), vol. 168, 5139-5146) is concerned with studies of expression of CEACAM1 on leucocytes of humans, mice and rats.

The publication by Greicius et al. ("CEACAM1 is a Potent Regulator of B Cell Receptor Complexinduced Activation", Gediminas Greicius, Eva Severinson, Nicole Beauchemin, Björn Öbrink and Bernhard B. Singer, Journal of Leukocyte Biology (2003), vol. 74, 126-134) mentions that CEACAM1 regulates the tumor growth of epithelial cells, angiogenesis, NK-cell cytotoxicity and also T cell cytotoxicity.

The publication by Chen et al. ("Editorial: CEACAM1: fine-tuned for fine-tuning", Zhangguo Chen, Lanfen Chen and Richard S. Blumberg, Journal of Leukocyte Biology (2009), vol. 86, 195-197) underlines the importance of CEACAM1 in relation to tumor genesis, angiogenesis and metabolism.

The publication by Lobo et al. ("Pivotal Advance: CEACAM1 is a Negative Coreceptor for the B Cell Receptor and Promotes CD19-mediated Adhesion of B Cells in a PI3K-dependent Manner", Elizabeth O. Lobo, Zhifang Zhang and John E. Shively, Journal of Leukocyte Biology (2009), vol. 86, 205-218) discloses that CEACAM1 is a negative receptor for what is termed the B cell receptor (BCR).

The publication by Blau et al. ("Targeted Disruption of the Ceacam1 (MHVR) Gene Leads to Reduced Susceptibility of Mice to Mouse Hepatitis Virus Infection", Dianna M. Blau, Claire Turbide, Michel Tremblay, Melanie Olson, Stéphanie Létourneau, Eva Michaliszyn, Serge Jothy, Kathryn V. Holmes and Nicole Beauchemin, Journal of Virology (2001), vol. 75, 8173-8186) discloses that CEACAM1-Knockout mice are less susceptible to a hepatitis infection.

WO 2005/058358 A2 discloses fusion proteins derived from CEACAM1 in the context of inflammatory diseases.

U.S. Pat. No. 8,598,322 B2 and also WO 2013/054331 A1 each disclose anti-CEACAM1 antibodies, and also use thereof for the treatment of cancer.

WO 2013/082366 A1 discloses CEACAM1-antibodies for tumor treatment, in particular cancer treatment.

WO 2013/054331 A1 addresses CEACAM1 antibodies in the context of the treatment of viral infections and cancers.

In WO 2014/022332 A1, a composition is described which modulates the interaction between TIM3 and CEACAM1.

Although the potential use of CEACAM1 as what is termed a therapeutic target has been recognized in principle, to date many questions with respect to therapeutic usability of CEACAM1 as a target have still not been clarified. In particular, to date there are contradictory data as to whether CEACAM1 is expressed on B cells and to what extent CEACAM1-binding substances, in particular antibodies, are able to influence B cells in vitro.

Likewise, to date the usability of CEACAM1 for activating other cells of the immune system, such as T cells, for instance, is unknown.

There continues to be a great need for the development of therapeutically effective substances, the therapeutic target of which is CEACAM1.

SUMMARY

An aspect of the present invention is to provide therapeutically effective substances which can bind CEACAM1, such as for instance anti-CEACAM1 antibodies, which are able to activate cells of the immune system, such as T cells for instance, and preferably, in addition, for the treatment and/or prevention of neoplasias and/or infections. An aspect of the present invention is also provide the indication areas of viral infections, viral infectious diseases, and also B-cell-dependent diseases.

An aspect of the present invention is to provide therapeutic substances that are suitable in particular for the therapy and viral infections, viral infectious diseases, and also B-cell-dependent diseases. An aspect of the present invention is to address the problem of providing substances for use in the diagnosis of, in particular, viral infections, viral infectious diseases, and also B-cell-dependent diseases.

In an embodiment, the present invention provides an anti-CEACAM1 antibody comprising at least one antibody heavy chain (VH) domain comprising antigen binding sites CDR1H, CDR2H and CDR3H, and at least one antibody light chain (VL) domain comprising antigen binding sites CDR1L, CDR2L and CDR3L. The antigen binding site CDR2H has a sequence homology of at least 80% to the amino acid sequence WINTYTGEPT (SEQ ID No. 21).

BRIEF DESCRIPTION OF THE DRAWINGS

The present invention is described in greater detail below on the basis of embodiments and of the drawings in which.

FIG. 8A shows the spleen VSV titer of WT or CEACAM1−/− mice 7 h after intravenous infection with $2\times10^6$ PFU of VSV (n=6 per genotype). ** $P<0.01$ (Student t-test);

FIG. 8B shows the interferon-alpha levels in the serum of WT or CEACAM1−/− mice 2 and 4 hours after intravenous infection with $2\times10^8$ PFU of VSV;

DETAILED DESCRIPTION

Figure 1:
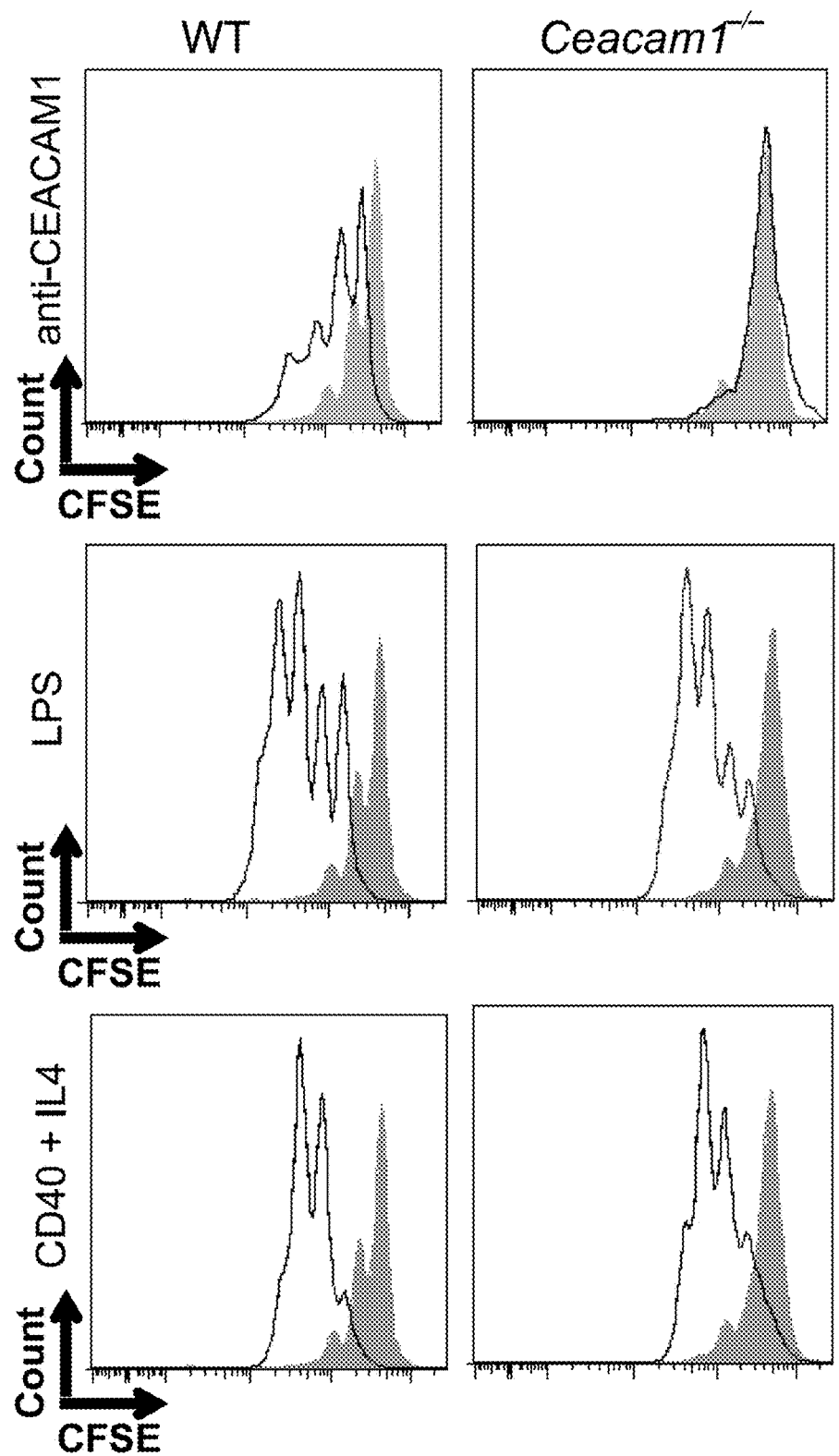
FIG. 1A shows representative continuous-flow cytometry histograms of profilerating B cells of wildtype (WT) or CEACAM1−/− mice (CEACAM1-Knockout mice), which were untreated (gray area), treated with anti-CEACAM1 antibody, LPS, or with recombinant mice-CD40 ligand in combination with mouse IL-4 (black line) for 48 hours. DAPI cells are shown (n=6)
FIG. 1B shows the absolute number of live cells B (DAPI−) at stated time points (n=3); sorted from the spleen, after treatment with or without recombinant mouse-CD40 ligand in combination with mouse IL-4 (n=3)
FIG. 1C shows representative histograms and statistical analysis of Annexin-V+ B cells: which were stimulated with recombinant mouse-CD40 ligand in combination with mouse IL-4 or left unstimulated, after 48 hours (DAPI− B cells are shown, n=6)
FIG. 1D shows the percentage of DAPI+ B cells from the spleen of WT and CEACAM1−/− mice after activation with recombinant mouse-CD40 ligand in combination with mouse IL-4 in the presence or absence of Btk inhibitor Ibrutinib cultured for 48 hours determined by FACS analysis (n=6). * $P<0.05$;  $P<0/01$; and * $P<0.001$ (Student t-test).
Figure 1:
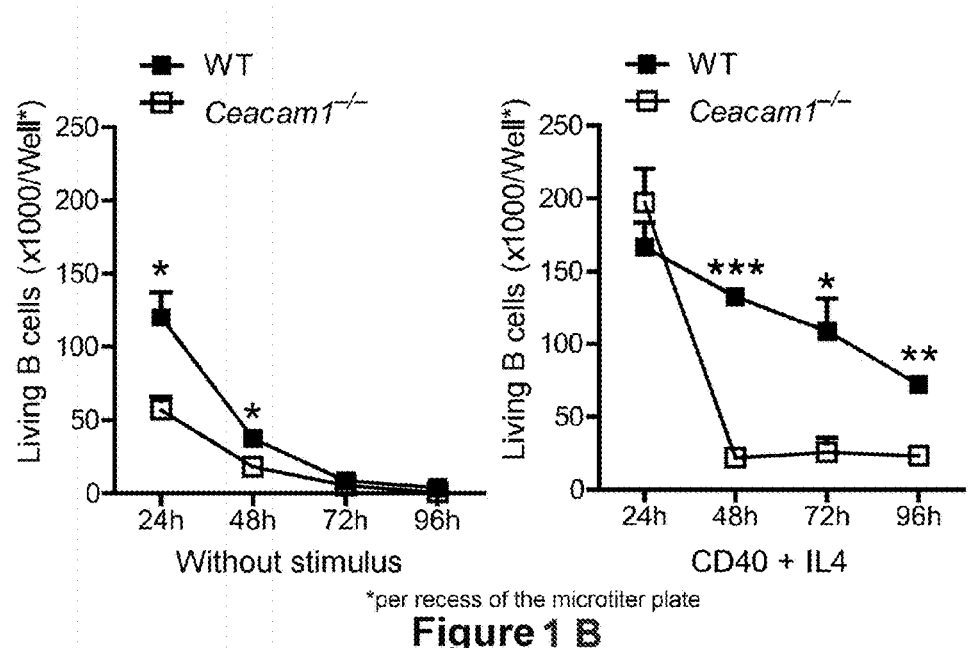
Figure 1:
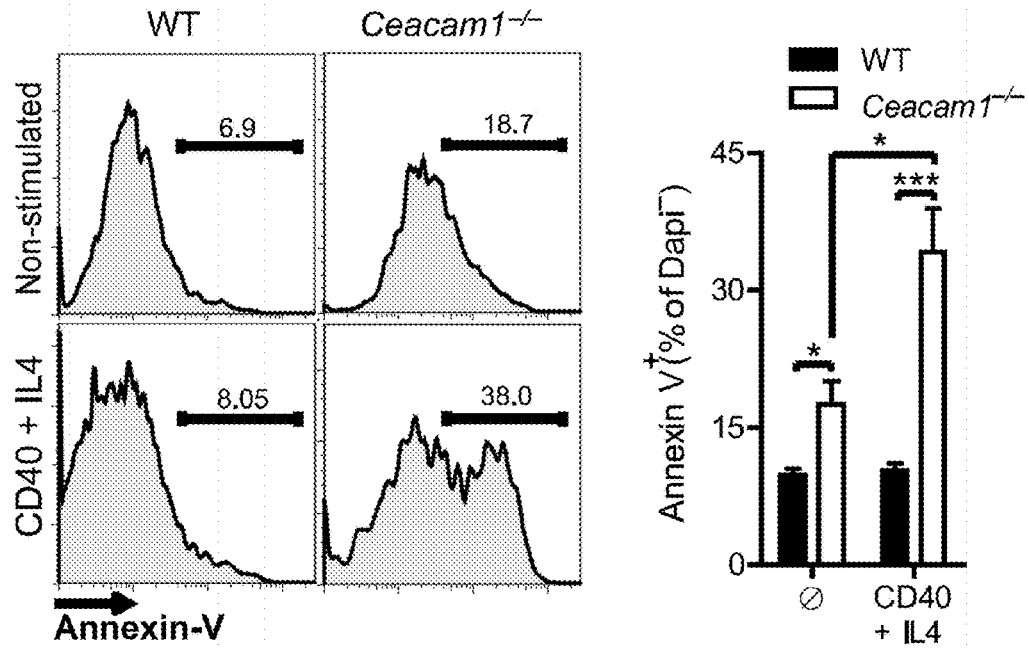
Figure 1:
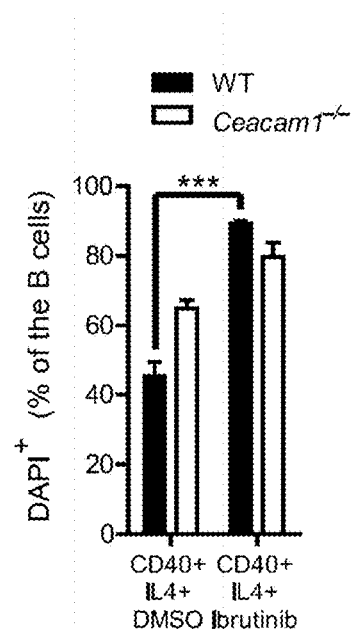

Surprisingly, it has been found that anti-CEACAM1 antibodies that contain an antigen-binding site CDR (Complementarity Determining Region) having at least 80% sequence homology to sequence WINTYTGEPT (SEQ ID No. 21) are particularly highly suitable.

Accordingly, a first aspect of the present invention relates to an anti-CEACAM1 antibody, comprising
(A) at least one antibody heavy chain ($V_H$) domain containing antigen binding sites $CDR1^H$, $CDR2^H$ and $CDR3^H$, and
(B) at least one antibody light chain ($V_L$) domain containing antigen binding sites $CDR1^L$, $CDR2^L$ and $CDR3^L$,
wherein $CDR2^H$ has at least 80% sequence homology to the following amino acid sequence:
WINTYTGEPT (SEQ ID No. 21).

According to a preferred embodiment, an antigen binding site $CDR2^H$ of at least 80% sequence homology to the amino acid sequence WINTYTGEPT (SEQ ID No. 21) can also be understood as an amino acid sequence that deviates from SEQ ID No. 21 by no more than two amino acid residues, preferably deviates from SEQ ID No. 21 by no more than a single amino acid residue, in particular is identical in sequence to SEQ ID No. 21.

Preferably, the dissociation constant $K_d$ of the binding of the anti-CEACAM1 antibody according to the present invention to CEACAM1 is not greater than 100 nM. In other words, the antigen-binding sites $CDR1^H$, $CDR2^H$, $CDR3^H$, $CDR1^L$, $CDR2^L$ and $CDR3^L$ are selected together such that the anti-CEACAM1 antibody binds to CEACAM1 with a dissociation constant $K_d$ of not greater than 100 nM, preferably not greater than 50 nM.

As used herein, CEACAM1 is preferably CEACAM1 of a mammal, in particular human CEACAM1.

The CDRs can be arranged in any sequence. Preferably, in the antibody heavy chain (VH) domain, the CDRs occur in the following sequence from the N to the C terminus: $CDR1^H$, $CDR2^H$, $CDR3^H$. Preferably, in the antibody light chain (VL) domain, the CDRs occur in the following sequence from the N to the C terminus: $CDR1^L$, $CDR2^L$, $CDR3^L$. In each case any number, preferably no more than 50, amino acid residues can be situated between the CDRs situated close to one another.

Further problems are solved according to the present invention by a substance according to independent embodiment 1 cited hereinafter, a drug according to embodiment 11 cited hereinafter, an antibody according to independent embodiment 12 cited hereinafter, a therapeutic antibody according to independent embodiment 13 cited hereinafter, a variable antibody heavy chain ($V_H$) domain according to independent embodiment 14 cited hereinafter, a variable antibody light chain ($V_L$) domain according to independent embodiment 15 cited hereinafter, isolated nucleic acids according to independent embodiments 16 and 17, a B-cell line according to embodiment 18 cited hereinafter, and also a method according to embodiment 19 cited hereinafter. Preferred embodiments are defined in dependent embodiments 2 to 9. The wording of all embodiments is hereby incorporated as contents of the present description by explicit reference.

In addition, the problems underlying the present invention are solved by the subjects of the present invention disclosed in the description.

The present invention is based on the following surprising findings:

Surprisingly, it has been found that the antibodies according to the present invention are suitable for activating T cells. It has been recognized that the antibodies according to the present invention are suitable for the prevention and treatment of neoplasias and infections.

Surprisingly, it was additionally found that activation of CEACAM1 in mice effects an activation, and in particular differentiation, of B cells and, in addition, permits in particular a beneficial influencing of the course of viral infections, and also infectious diseases. As a virus model, the lymphocytic choriomeningitis virus (LCMV) and vesicular stomatitis virus (VSV) are used. The LCMV is not cytopathic in mice. Therefore, the damage which results from an infection, is primarily caused by the immune response to the virus. Therefore, this virus behaves similar to the weakly cytopathic viruses Hepatitis-B virus (HBV), Hepatitis-C virus (HCV) and human immunodeficiency virus (HIV) in humans. The vesicular stomatitis virus is cytopathic in mice. It therefore behaves similar to the Ebola virus, polio virus, rabies virus, Ebstein-Barr virus (EBV), influenza virus, herpes simplex virus and also cytomegalovirus (CMV).

In addition, in the context of mice studies, surprisingly, it was shown that inhibition of CEACAM1 in vivo strongly inhibits the activation and differentiation or development of B cells, and in particular hinders the outbreak of a B-cell-dependent autoimmunity. In this case, in mice, a B-cell-dependent autoimmunity was induced by means of pristane. In this case, it was observed that inhibition of CEACAM1 prevented disease in mice. In addition, the inventors found that inhibition of CEACAM1 led to reduced serum-IGE concentrations.

The term "expression", in the context of the present invention, comprises all processes which are required for complete, that is to say functional, expression of the protein CEACAM1. Thus, the term "expression", in the context of the present invention, in particular comprises the transcription, subsequent RNA-processing, translation, and also protein maturation, such as, for example, protein folding and post-translational modifications of CEACAM1.

The phrase "function of CEACAM1", in the context of the present invention, defines the physiological function or the physiological functions of CEACAM1, in particular the ability thereof to influence the activity, and in particular differentiation, of B cells.

As described hereinbefore, the anti-CEACAM1 antibody has an antigen binding site $CDR2^H$ of at least 80% sequence homology to the amino acid sequence WINTYTGEPT (SEQ ID No. 21), the remaining antigen binding sites $CDR1^H$, $CDR3^H$, $CDR1^L$, $CDR2^L$ and $CDR3^L$) can in principle be variable with respect to the amino acid sequence thereof, but are suitable in their totality for improving the binding of the anti-CEACAM1 antibody to CEACAM1.

Sequence homology is to be understood in the broadest sense, in particular as sequence homology as according to the BLAST algorithm (Basic Local Alignment Search Tool) of the National Center for Biotechnology Information (NCBI) for protein sequence comparisons (blastp) in the version current on Jul. 14, 2016.

It is understood that the amino acid sequences, anti-CEACAM1 antibodies, antibody domains, antigen binding sites CDRs etc. shown and described herein can optionally have in each case post-translational modifications such as, for example, glycosylation, sulfation, phosphation, acetylation, acylation, etc. Alternatively, or in addition thereto, the amino acid sequences, anti-CEACAM1 antibodies, antibody domains, antigen binding sites CDRs etc. shown and described herein can in each case have synthetic modifications such as, by way of example, labeling (e.g. fluorophors, binding molecules (biotin, streptavidin, methotrexate etc.). Also, an anti-CEACAM1 antibody can optionally be provided thereby with a radioactive or spin label in such a manner that one of the naturally occurring atoms is replaced by a detectable isotope (e.g. $^3$H, $^{13}$C etc.).

Preferably, the antibody according to the present invention has an antigen-binding site CDR2$^H$ of at least 90% sequence homology, more preferably of at least 95% sequence homology, in particular with sequence identity, to the amino acid sequence WINTYTGEPT (SEQ ID No. 21).

According to a preferred embodiment, the anti-CEACAM1 antibody binds the N-domain of CEACAM1 as per SEQ ID No. 39.

According to a more greatly preferred embodiment, the anti-CEACAM1 antibody binds the N-domain of CEACAM1 as per SEQ ID No. 39, and in addition at least one further domain selected from the group consisting of A1-domain of CEACAM1 as per SEQ ID No. 40, B-domain of CEACAM1 as per SEQ ID No. 41 and A2-domain of CEACAM1 as per SEQ ID No. 42.

According to a preferred embodiment, the anti-CEACAM1 antibody binds the N-domain of CEACAM1 as per SEQ ID No. 39 and in addition the A1-domain CEACAM1 as per SEQ ID No. 40.

According to a preferred embodiment, the anti-CEACAM1 antibody binds the N-domain CEACAM1 as per SEQ ID No. 39, and in addition the B-domain of CEACAM1 as per SEQ ID No. 41.

According to a preferred embodiment, the anti-CEACAM1 antibody binds the N-domain of CEACAM1 as per SEQ ID No. 39 and in addition the A2-domain of CEACAM1 as per SEQ ID No. 42.

According to a preferred embodiment, the anti-CEACAM1 antibody binds the N-domain CEACAM1 as per SEQ ID No. 39, and in addition the A1-domain of CEACAM1 as per SEQ ID No. 40 and the B-domain of CEACAM1 as per SEQ ID No. 41.

According to a preferred embodiment, the anti-CEACAM1 antibody binds the N-domain of CEACAM1 as per SEQ ID No. 39, and in addition the A1-domain of CEACAM1 as per SEQ ID No. 40 and the A2-domain of CEACAM1 as per SEQ ID No. 42.

According to a preferred embodiment, the anti-CEACAM1 antibody binds the N-domain of CEACAM1 as per SEQ ID No. 39 and in addition the B-domain of CEACAM1 as per SEQ ID No. 41 and the A2-domain of CEACAM1 as per SEQ ID No. 42.

According to a more preferred embodiment, the anti-CEACAM1 antibody binds the N-domain of CEACAM1 as per SEQ ID No. 39 and in addition the A1-domain of CEACAM1 as per SEQ ID No. 40, the B-domain of CEACAM1 as per SEQ ID No. 41, and the A2-domain of CEACAM1 as per SEQ ID No. 42.

These instances of binding are achieved by the particular antigen-binding site CDR2$^H$, in particular the particular antigen-binding site CDR2$^H$ in combination with one or more further CDRs in the preferred embodiments.

Preferably, these instances of binding are in each case a binding in which the dissociation constant $K_d$ of the respective binding is no greater than 1000 nM, more preferably no greater than 500 nM, in particular no greater than 100 nM.

It is understood that the antibody in each case binds one or more epitopes within these sequences. An epitope can in each case be any type of epitope, such as, e.g. a linear epitope or a structural epitope, a primary epitope or a secondary epitope.

According to a preferred embodiment, the epitope that is bound by the antibody is 3 to 20 amino acid residues long and consists of 1 to 3 amino acid sequences of the N-domain and also 1 to 3 amino acid sequences of the A1-, B- and/or A2-domain.

The amino acid sequences SEQ ID Nos 39-42 are as follows:

```
SEQ ID No. 39: CEACAM1-N-domain
(= Ig-like V-type)
QLTTESMPFNVAEGKEVLLLVHNLPQQLFGYSWYKGERVDGNRQIVGYAI

GTQQATPGPANSGRETIYPNASLLIQNVTQNDTGFYTLQVIKSDLVNEEA

TGQFHVYP

SEQ ID No. 40: CEACAM1-A1-domain
(= Ig-like C2-type 1)
PKPSISSNNSNPVEDKDAVAFTCEPETQDTTYLWWINNQSLPVSPRLQLS

NGNRTLTLLSVTRNDTGPYECEIQNPVSANRSDPVTLN

SEQ ID No. 41: CEACAM1-B-domain
(= Ig-like C2-type 2)
PDTPTISPSDTYYRPGANLSLSCYAASNPPAQYSWLINGTFQQSTQELFI

PNITVNNSGSYTCHANNSVTGCNRTTVKTII

SEQ ID No. 42: CEACAM1-A2-domain
(= Ig-like C2-type 3)
PVVAKPQIKASKTTVTGDKDSVNLTCSTNDTGISIRWFFKNQSLPSSERM

KLSQGNTTLS

INPVKREDAGTYWCEVFNPISKNQSDPIMLN
```

The consensus sequence SEQ ID No. 43 of CEACAM1 is as follows:

```
MGHLSAPLHRVRVPWQGLLLTASLLTFWNPPTTAQLTTESMPFNVAEGKE

VLLLVHNLPQQLFGYSWYKGERVDGNRQIVGYAIGTQQATPGPANSGRET

IYPNASLLIQNVTQNDTGFYTLQVIKSDLVNEEATGQFHVYPELPKPSIS

SNNSNPVEDKDAVAFTCEPETQDTTYLWWINNQSLPVSPRLQLSNGNRTL

TLLSVTRNDTGPYECEIQNPVSANRSDPVTLNVTYGPDTPTISPSDTYYR

PGANLSLSCYAASNPPAQYSWLINGTFQQSTQELFIPNITVNNSGSYTCH

ANNSVTGCNRTTVKTIIVTELSPVVAKPQIKASKTTVTGDKDSVNLTCST

NDTGISIRWFFKNQSLPSSERMKLSQGNTTLSINPVKREDAGTYWCEVFN

PISKNQSDPIMLNVNYNALPQENGLSPGAIAGIVIGVVALVALIAVALAC

FLHFGKTGRASDQRDLTEHKPSVSNHTQDHSNDPPNKMNEVTYSTLNFEA

QQPTQPTSASPSLTATEIIYSEVKKQ
```

A polypeptide of the consensus sequence SEQ ID No. 43 of CEACAM1 preferably forms the following secondary structures (positions): beta-folded sheet (37-46), beta-folded sheet (37-46), beta-folded sheet (51-56), beta-folded sheet (60-73), helix (75-77), beta-folded sheet (78-83), turn (84-

87), beta-folded sheet (88-91), beta-folded sheet (99-101), beta-folded sheet (107-109), helix (114-116), beta-folded sheet (118-126), beta-folded sheet (132-141).

According to a particularly preferred embodiment, the epitope on the CEACAM1-N-domain recognized by the anti-CEACAM1 antibody according to the present invention comprises the amino acid residues Y68, K69, R72, F119 and E133 consensus sequence SEQ ID No. 43 of CEACAM1.

According to a preferred embodiment, CDR2$^L$ of the antibody according to the present invention has the following amino acid sequence: YTSX$_{b4}$LX$_{b6}$X$_{b7}$ (SEQ ID No. 22), wherein X$_{b4}$, X$_{b6}$, and X$_{b7}$ each independently of one another are any amino acid residue.

More preferably, in the amino acid sequence YTSX$_{b4}$LX$_{b6}$X$_{b7}$ (SEQ ID No. 22), the residues X$_{b4}$, X$_{b6}$, and X$_{b7}$ are defined in such a manner that: X$_{b4}$ is T or K, X$_{b6}$ is Q or H, and X$_{b7}$ is P or S.

Accordingly, the residues can be defined as follows: X$_{b4}$=T, X$_{b6}$=Q and X$_{b7}$=P; X$_{b4}$=T, X$_{b6}$=Q and X$_{b7}$=S; X$_{b4}$=T, X$_{b6}$=H and X$_{b7}$=P; X$_{b4}$=T, X$_{b6}$=H and X$_{b7}$=S; X$_{b4}$=K, X$_{b6}$=Q and X$_{b7}$=P; X$_{b4}$=K, X$_{b6}$=Q and X$_{b7}$=S; X$_{b4}$=K, X$_{b6}$=H and X$_{b7}$=P; or X$_{b4}$=T, X$_{b6}$=H and X$_{b7}$=S.

According to a particularly highly preferred embodiment, CDR2$^L$ has at least 80% sequence homology to one of the following amino acid sequences: YTSTLQP (SEQ ID No. 23), or YTSKLHS (SEQ ID No. 24).

According to a preferred embodiment, an antigen-binding site CDR2$^L$ of at least 80% sequence homology to the amino acid sequence TSTLQP (SEQ ID No. 23) or YTSKLHS (SEQ ID No. 24) can also be understood as an amino acid sequence that does not deviate from SEQ ID No. 23 or 24 by more than a single amino acid residue, in particular is identical in sequence to SEQ ID No. 23 or 24.

More highly preferably, CDR2$^L$ has at least 90% sequence homology, still more highly preferably at least 95% sequence homology, in particular sequence identity, to one of the following amino acid sequences: YTSTLQP (SEQ ID No. 23), or YTSKLHS (SEQ ID No. 24).

Particularly preferably, the antibody according to the present invention has a CDR2$^H$ of an amino acid sequence WINTYTGEPT (SEQ ID No. 21) and a CDR2$^L$ of at least 80% sequence homology to one of the following amino acid sequences: YTSTLQP (SEQ ID No. 23), or YTSKLHS (SEQ ID No. 24).

According to a preferred embodiment, CDR1$^H$ has the following amino acid sequence:
GYX$_{a3}$FX$_{a5}$X$_{a6}$YX$_{a8}$MX$_{a10}$ (SEQ ID No. 25), wherein X$_{a3}$, X$_{a5}$, X$_{a6}$, X$_{a8}$ and X$_{a10}$ in each case independently of one another are any amino acid residue.

According to a more highly preferred embodiment, CDR1$^H$ is characterized in that
X$_{a3}$ is T or I,
X$_{a5}$ is T or R,
X$_{a6}$ is selected from the group consisting of V, N and T,
X$_{a8}$ is G or V, and
X$_{a10}$ is selected from the group consisting of N, K and H.

According to a particularly preferred embodiment, CDR1$^H$ has at least 80% sequence homology to one of the following amino acid sequences: GYTFTVYGMN (SEQ ID No. 26), GYIFRNYGMK (SEQ ID No. 27), or GYTFTYVMH (SEQ ID No. 28).

According to a preferred embodiment, an antigen-binding site CDR1$^H$ of at least 80% sequence homology to the amino acid sequence SEQ ID No. 26, 27 or 28 can also be taken to mean an amino acid sequence which deviates by no more than two amino acid residues from SEQ ID No. 26, 27 or 28, more highly preferably deviates by no more than a single amino acid residue from SEQ ID No. 26, 27 or 28, in particular is identical in sequence to SEQ ID No. 26, 27 or 28.

More highly preferably, CDR1$^H$ has at least 90% sequence homology, still more highly preferably at least 95% sequence homology, in particular sequence identity to one of the following amino acid sequences: GYTFT-VYGMN (SEQ ID No. 26), GYIFRNYGMK (SEQ ID No. 27), or GYTFTTYVMH (SEQ ID No. 28).

According to a preferred embodiment, CDR1$^L$ has the following amino acid sequence: X$_{d1}$ASX$_{d4}$X$_{d5}$IX$_{d7}$X$_{d8}$X$_{d9}$LX$_{d11}$ (SEQ ID No. 29), wherein X$_{d1}$, X$_{d4}$, X$_{d5}$, X$_{d7}$, X$_{d8}$, X$_{d9}$ and X$_{d11}$, in each case independently of one another, are any amino acid residue.

According to a more highly preferred embodiment, CDR1$^L$ is characterized in that:
X$_{d1}$ is a basic amino acid residue, in particular K or R,
X$_{d4}$ is Q or D, in particular is Q;
X$_{d5}$ is D or H, in particular is D;
X$_{d7}$ is N or S,
X$_{d8}$ is K or N
X$_{d9}$ is an aromatic amino acid residue, in particular selected from the group consisting of F, Y and W, and in particular is F or Y, and
X$_{d11}$ is A or N.

According to a still more highly preferred embodiment, CDR1$^L$ is characterized in that:
X$_{d1}$ is a basic amino acid residue, in particular is K or R,
X$_{d4}$ is Q,
X$_{d5}$ is D,
X$_{d7}$ is N or S,
X$_{d8}$ is K or N,
X$_{d9}$ is F or Y, and
X$_{d11}$ is A or N.

According to a particularly preferred embodiment, CDR1$^L$ has at least 80% sequence homology to one of the following amino acid sequences: KASQDINKFLA (SEQ ID No. 30), RASQDISNYLN (SEQ ID No. 31), or KASDHIN-NWLA (SEQ ID No. 32).

According to a preferred embodiment, an antigen-binding site CDR1$^L$ of at least 80% sequence homology to the amino acid sequence SEQ ID No. 30, 31 or 32 can also be taken to mean an amino acid sequence that deviates by no more than two amino acid residues from SEQ ID No. 30, 31 or 32, more highly preferably deviates by no more than a single amino acid residue from SEQ ID No. 30, 31 or 32, in particular is identical in sequence to SEQ ID No. 30, 31 or 32.

More particularly CDR1$^L$ has at least 90% sequence homology, still more highly preferably at least 95% sequence homology, in particular is identical in sequence to one of the following amino acid sequences: KASQDIN-KFLA (SEQ ID No. 30), RASQDISNYLN (SEQ ID No. 31), or KASDHINNWLA (SEQ ID No. 32).

According to a particularly preferred embodiment, CDR2$^H$, CDR2$^L$, CDR1$^H$ and CDR1$^L$ are defined as described hereinbefore.

According to a particularly preferred embodiment, the anti-CEACAM1 antibody has:
a variable antibody heavy chain (V$_H$) domain having at least 80% sequence homology to SEQ ID No. 3 or SEQ ID No. 7; and/or
a variable antibody light chain (V$_L$) domain having at least 80% sequence homology to SEQ ID No. 5 or SEQ ID No. 9.

Still more highly preferably, the anti-CEACAM1 antibody according to the present invention has:

a variable antibody heavy chain ($V_H$) domain having at least 90% sequence homology to SEQ ID No. 3 or SEQ ID No. 7; and/or a variable antibody light chain ($V_L$) domain having at least 90% sequence homology to SEQ ID No. 5 or SEQ ID No. 9.

Still more highly preferably, the anti-CEACAM1 antibody according to the present invention has:

a variable antibody heavy chain ($V_H$) domain having at least 95% sequence homology to SEQ ID No. 3 or SEQ ID No. 7; and/or a variable antibody light chain ($V_L$) domain having at least 95% sequence homology to SEQ ID No. 5 or SEQ ID No. 9.

Still more highly preferably, the anti-CEACAM1 antibody according to the present invention has:

a variable antibody heavy chain ($V_H$) domain having sequence identity to SEQ ID No. 3 or SEQ ID No. 7; and/or a variable antibody light chain ($V_L$) domain having sequence identity to SEQ ID No. 5 or SEQ ID No. 9.

According to another particularly preferred embodiment, the anti-CEACAM1 antibody according to the present invention has:

a variable antibody heavy chain ($V_H$) domain as per SEQ ID No. 3 or SEQ ID No. 7 or an amino acid sequence that deviates from SEQ ID No. 3 or SEQ ID No. 7 by a single amino acid residue; and/or a variable antibody light chain ($V_L$) domain as per SEQ ID No. 5 or SEQ ID No. 9 or an amino acid sequence that deviates from SEQ ID No. 5 or SEQ ID No. 9 by a single amino acid residue.

Very particularly preferably, the anti-CEACAM1 antibody according to the present invention has:

a variable antibody heavy chain ($V_H$) domain as per SEQ ID No. 3 or SEQ ID No. 7; and a variable antibody light chain ($V_L$) domain as per SEQ ID No. 5 or SEQ ID No. 9.

Preferably, the anti-CEACAM1 antibody comprises to the CDR3$^H$ having the following amino acid sequence: $X_{c1}X_{c2}X_{c3}X_{c4}X_{c5}X_{c6}X_{c7}X_{c8}X_{c9}X_{c10}$ (SEQ ID No. 33), wherein:

$X_{c1}$ is Y or I,
$X_{c2}$ is R or T,
$X_{c3}$ is Y or T,
$X_{c4}$ is D or S,
$X_{c5}$ is G or N,
$X_{c6}$ is G or Y,
$X_{c7}$ is M or A,
$X_{c8}$ is D or L,
$X_{c9}$ is Y or D, and
$X_{c10}$ is N or is absent.

Preferably, CDR3$^H$ has at least 80% sequence homology, more highly preferably at least 90% sequence homology, still more highly preferably at least 95% sequence homology, in particular is identical in sequence to one of the following amino acid sequences:

YRYDGGMDY (SEQ ID No. 34) or ITTSNYALDN (SEQ ID No. 35).

According to a preferred embodiment, an antigen-binding site CDR3$^H$ of at least 80% sequence homology to an amino acid sequence SEQ ID No. 34 or 35 can also be understood as an amino acid sequence which deviates from SEQ ID No. 34 or 35 by no more than two amino acid residues, or highly preferably deviates from SEQ ID No. 34 or 35 by no more than a single amino acid residue, in particular is identical in sequence to SEQ ID No. 34 or 35.

Preferably, in addition, the anti-CEACAM1 antibody has a CDR3$^L$ having the following amino acid sequence: $X_{f1}QX_{f3}X_{f4}X_{f5}LX_{f7}X_{f8}X_{f9}$ (SEQ ID No. 36), wherein $X_{f1}$, $X_{f3}$, $X_{f4}$, $X_{f5}$, $X_{f7}$, $X_{f8}$ and $X_{f9}$ in each case independently of one another are any amino acid residues. Preferably, the amino acid residues are defined in such a manner that:

$X_{f1}$ is L or Q,
$X_{f3}$ is Y or G,
$X_{f4}$ is D or N,
$X_{f5}$ is N or T,
$X_{f7}$ is Y or P,
$X_{f8}$ is T or W,
$X_{f9}$ is T or is absent.

Preferably, CDR3$^L$ has at least 80% sequence homology, more highly preferably at least 90% sequence homology, still more highly preferably at least 95% sequence homology, in particular is identical in sequence, to one of the following amino acid sequences: LQYDNLYT (SEQ ID No. 37), or QQGNTLPWT (SEQ ID No. 38).

According to a preferred embodiment, an antigen-binding site CDR3$^L$ of at least 80% sequence homology to the amino acid sequence SEQ ID No. 37 or 38 can also be understood as an amino acid sequence which deviates from SEQ ID No. 37 or 38 by no more than two amino acid residues, more highly preferably deviates from SEQ ID No. 37 or 38 by no more than a single amino acid residue, in particular is identical in sequence to SEQ ID No. 37 or 38.

According to a preferred embodiment, the anti-CEACAM1 antibody according to the present invention comprises:

a CDR1$^H$ as per SEQ ID No. 25, in particular of at least 80% sequence homology to SEQ ID No. 26, SEQ ID No. 27 or SEQ ID No. 28;

a CDR2$^H$ of at least 80% sequence homology to SEQ ID No. 21; and a CDR3$^H$ as per SEQ ID No. 33, in particular of at least 80% sequence homology to SEQ ID No. 34 or SEQ ID No. 35.

According to a preferred embodiment, the anti-CEACAM1 antibody according to the present invention comprises:

a CDR1$^H$ as per SEQ ID No. 25, in particular of at least 80% sequence homology to SEQ ID No. 26, SEQ ID No. 27 or SEQ ID No. 28;

a CDR1$^L$ as per SEQ ID No. 29, in particular of at least 80% sequence homology to SEQ ID No. 30, SEQ ID No. 31 or SEQ ID No. 32;

a CDR2$^H$ of at least 80% sequence homology to SEQ ID No. 21; and a CDR2$^L$ as per SEQ ID No. 22, in particular of at least 80% sequence homology to SEQ ID No. 23 or SEQ ID No. 24.

According to a preferred embodiment, the anti-CEACAM1 antibody according to the present invention comprises:

a CDR2$^H$ of at least 80% sequence homology to SEQ ID No. 21;

a CDR2$^L$ as per SEQ ID No. 22, in particular of at least 80% sequence homology to SEQ ID No. 23 or SEQ ID No. 24;

a CDR3$^H$ as per SEQ ID No. 33, in particular of at least 80% sequence homology to SEQ ID No. 34 or SEQ ID No. 35; and a CDR3$^L$ as per SEQ ID No. 39, in particular of at least 80% sequence homology to SEQ ID No. 37 or SEQ ID No. 38.

According to a preferred embodiment, the anti-CEACAM1 antibody according to the present invention comprises:
- a $CDR1^H$ as per SEQ ID No. 25, in particular of at least 80% sequence homology to SEQ ID No. 26, SEQ ID No. 27 or SEQ ID No. 28;
- a $CDR1^L$ as per SEQ ID No. 29, in particular of at least 80% sequence homology to SEQ ID No. 30, SEQ ID No. 31 or SEQ ID No. 32;
- a $CDR2^H$ of at least 80% sequence homology to SEQ ID No. 21;
- a $CDR2^L$ as per SEQ ID No. 22, in particular of at least 80% sequence homology to SEQ ID No. 23 or SEQ ID No. 24;
- a $CDR3^H$ as per SEQ ID No. 33, in particular of at least 80% sequence homology to SEQ ID No. 34 or SEQ ID No. 35; and
- a $CDR3^L$ as per SEQ ID No. 39, in particular of at least 80% sequence homology to SEQ ID No. 37 or SEQ ID No. 38, wherein the antibody preferably binds the N-domain of CEACAM1 as per SEQ ID No. 39, in particular wherein the antibody preferably binds the N-domain of CEACAM1 as per SEQ ID No. 39 and in addition a further domain selected from the group consisting of A1-domain of CEACAM1 as per SEQ ID No. 40, B-domain of CEACAM1 as per SEQ ID No. 41 and A2-domain of CEACAM1 as per SEQ ID No. 42.

According to a particularly preferred embodiment, the anti-CEACAM1 antibody according to the present invention comprises:
- a $CDR1^H$ of at least 80% sequence homology to SEQ ID No. 26, SEQ ID No. 27 or SEQ ID No. 28;
- a $CDR1^L$ of at least 80% sequence homology to SEQ ID No. 30, SEQ ID No. 31 or SEQ ID No. 32;
- a $CDR2^H$ of at least 80% sequence homology to SEQ ID No. 21;
- a $CDR2^L$ of at least 80% sequence homology to SEQ ID No. 23 or SEQ ID No. 24;
- a $CDR3^H$ of at least 80% sequence homology to SEQ ID No. 34 or SEQ ID No. 35; and
- a $CDR3^L$ of at least 80% sequence homology to SEQ ID No. 37 or SEQ ID No. 38, wherein the antibody preferably binds the N-domain of CEACAM1 as per SEQ ID No. 39, in particular wherein the antibody preferably binds the N-domain of CEACAM1 as per SEQ ID No. 39 and in addition at least one further domain selected from the group consisting of A1-domain of CEACAM1 as per SEQ ID No. 40, B-domain of CEACAM1 as per SEQ ID No. 41 and A2-domain of CEACAM1 as per SEQ ID No. 42.

According to a very particularly preferred embodiment, the anti-CEACAM1 antibody according to the present invention comprises:
- a $CDR1^H$ as per SEQ ID No. 26, SEQ ID No. 27 or SEQ ID No. 28;
- a $CDR1^L$ as per SEQ ID No. 30, SEQ ID No. 31 or SEQ ID No. 32;
- a $CDR2^H$ as per SEQ ID No. 21;
- a $CDR2^L$ as per SEQ ID No. 23 or SEQ ID No. 24; and
- a $CDR3^H$ as per SEQ ID No. 34 or SEQ ID No. 35; and
- a $CDR3^L$ as per SEQ ID No. 37 or SEQ ID No. 38, wherein the antibody preferably binds the N-domain of CEACAM1 as per SEQ ID No. 39, in particular wherein the antibody preferably binds the N-domain of CEACAM1 as per SEQ ID No. 39 and in addition at least one further domain selected from the group consisting of A1-domain of CEACAM1 as per SEQ ID No. 40, B-domain of CEACAM1 as per SEQ ID No. 41 and A2-domain of CEACAM1 as per SEQ ID No. 42.

The antibody according to the present invention will generally bind to CEACAM1 with a dissociation constant $K_d$ of no more than 1000 nM, preferably binds to CEACAM1 with a dissociation constant $K_d$ of no more than 100 nM.

According to a preferred embodiment, the binding to CEACAM1 of the antibody according to the present invention has a dissociation constant $K_d$ of no more than 50 nM.

More highly preferably, the binding of the antibody to CEACAM1 has a dissociation constant $K_d$ of not more than 40 nM, in particular not more than 30 nM.

Surprisingly, it has been found that the antibody activity is optimum when the antibody binds the N domain and in addition the A1-domain, B-domain or A2-domain.

Accordingly, the present invention, in a further aspect, also relates to an anti-CEACAM1 antibody that binds to the N-domain of CEACAM1 as per SEQ ID No. 39, and preferably at least one further domain selected from the group consisting of A1-domain of CEACAM1 as per SEQ ID No. 40, B-domain of CEACAM1 as per SEQ ID No. 41 and the A2-domain of CEACAM1 as per SEQ ID No. 42.

According to a preferred embodiment, the anti-CEACAM1 antibody which is characterized in that it binds to the N-domain of CEACAM1 and at least one further of said domains, also has other properties as described hereinbefore.

It will be understandable to a person skilled in the art that the antibodies are generally obtained via gene expression. Therefore, a further aspect of the present invention relates to a nucleic acid encoding one of the anti-CEACAM1 antibodies according to the present invention.

Likewise, the present invention relates to cells, in particular mammalian cells, that contain such a nucleic acid.

The present invention also relates to the therapeutic, preventive, and in vitro application of the antibody. Therefore, an aspect relates to the anti-CEACAM1 antibody according to the present invention for use as a drug.

As noted hereinbefore, the anti-CEACAM1 antibody according to the present invention is suitable for prevention of neoplasias and infections.

Therefore, a further of the present invention relates to the anti-CEACAM1 antibody according to the present invention for use in a method for treatment and/or prevention of neoplasias and/or infections.

In other words, the present invention relates to a method for treatment and/or prevention of neoplasias and/or infections, comprising the administration of a sufficient amount to the patients that are to be treated.

According to a preferred embodiment, neoplasias are malign tumors and/or cancer and/or infections viral infections, or viral infectious diseases. These are described herein in more detail.

It will be understood that the anti-CEACAM1 antibody according to the present invention, for such a therapeutic or preventive use, can be dissolved in a suitable pharmaceutically compatible liquid or pasty carrier. Therefore, an aspect of the present present invention also relates to a pharmaceutical composition containing at least one anti-CEACAM1 antibody according to the present invention and at least one pharmaceutically compatible carrier. By way of example, a pharmaceutically compatible carrier can be an aqueous buffer (e.g. a hepes, tris or phosphate buffer), an organic solvent (e.g. dimethyl sulfoxide (DMSO), ethanol) or a mixture or two or more thereof.

As described above, the anti-CEACAM1 antibodies according to the present invention surprisingly are also suitable for activating T cells. This can also proceed ex vivo and therefore in vitro.

A further aspect of the present invention therefore relates to a method for activating T cells in vitro, comprising the following steps:
(i) providing non-activated T cells;
(ii) contacting the non-activated T cells with:
 (a) an anti-CEACAM1 antibody as claimed in any one of claims 1 to 12, and
 (b) an epitope against which the T cells are directed; and
(iii) culturing the T cells that are treated as per step (ii) under conditions that do not hinder the activation of the T cells.

T cells are preferably CD8-positive T cells. The T cells can be taken from a patient or can originate from a cell culture. The culturing conditions are preferably about 37° C. in nutrient solution at approximately pH 7.1-7.4 for some hours or days. The method is also elucidated by way of example in the examples hereinafter.

The term "antibody", as used herein, should be taken to mean in the broadest sense as any type of immunoglobulin or antigen-binding fragment of one such. Numerous forms of antibodies are known in the prior art. In addition to the antibody heavy chain ($V_H$) domain and the antibody light chain ($V_L$) domain, the antibody can be made in any way. In the experiments, a mouse-antibody was used. A person skilled in the art knows directly how such a mouse antibody is made up and is available. The constant part of the antibody (Fc) is then mouse-typical. The antibody can be humanized, in particular for therapeutic and/or preventive application.

By way of example, the antibody can be: Immunoglobulin A (IgA), Immunoglobulin D (IgD), Immunoglobulin E (IgE), Immunoglobulin G (IgG), Immunoglobulin M (IgM), Immunoglobulin Y (IgY) and Immunoglobulin W (IgW). Preferred antibodies are selected from the group consisting of IgA, IgG and IgD, in particular IgG. According to a preferred embodiment, the antibody according to the present invention is a humanized antibody, in particular a humanized IgG antibody.

An antigen binding fragment, in the context of the present invention, also has an antigen-binding site $CDR2^H$ of at least 80% sequence homology to an amino acid sequence WIN-TYTGEPT (SEQ ID No. 21), the remaining antigen-binding sites $CDR1^H$, $CDR3^H$, $CDR1^L$, $CDR2^L$ and $CDR3^L$ are variable. An example of an antigen-binding fragment is a "fragment antigen binding" (Fab fragment), a truncated antibody having one or two CDR regions, or an isolated variable fragment (Fv) of an antibody.

The antibodies disclosed in the context of the present invention preferably have in each case a structure characteristic of antibodies: They each have two identical heavy polypeptide chains and two identical light polypeptide chains, which are linked to one another by covalent disulfide bonds to form a Y-shape structure. The light chains each consist of a variable domain, hereinafter termed variable antibody light chain ($V_L$) domain, and a constant domain, hereinafter called constant antibody light chain ($C_L$) domain. The heavy chains, in contrast, each have a variable domain, hereinafter called variable antibody heavy chain ($V_H$) domain, and three constant domains, hereinafter called constant antibody heavy chain ($C_H$) domains. If, accordingly, in the context of the present invention, a variable antibody heavy chain ($V_H$) domain of the antibody is mentioned, or a variable antibody light chain ($V_L$) domain of the antibody is mentioned, this means that the antibody in total has two variable antibody heavy chain ($V_H$) domains, namely one variable antibody heavy chain ($V_H$) domain per heavy chain, or two variable antibody light chain ($V_L$) domains, namely one variable antibody light chain ($V_L$) domain per light chain, having the features disclosed hereinafter. The same applies correspondingly if, hereinafter, a constant antibody light chain ($C_L$) domain of the antibody is mentioned. If hereinafter constant antibody heavy chain ($C_H$) domains of the antibody are mentioned, this means the constant antibody heavy chain ($C_H$) domains of both heavy chains of the antibody.

According to a further aspect, the present invention relates to the use of an anti-CEACAM1 antibody as immunostimulant, wherein this is optionally used in combination with one or more other immunostimulants (e.g. TLR agonists, T-cell ligands etc.).

In other words, the present invention relates to an anti-CEACAM1 antibody for activating immune cells, in particular T cells.

Preferably, in this case, the anti-CEACAM1 antibody is an anti-CEACAM1 antibody according to the present invention as described herein.

An anti-CEACAM1 antibody, in particular an anti-CEACAM1 antibody according to the present invention as described herein can bring one or more CEACAM1 polypeptides and optionally other polypeptides into a shared configuration. This can lead to the activation of a CEACAM1-mediated signal transduction pathway, which in turn can activate T cells. An anti-CEACAM1 antibody, in particular an anti-CEACAM1 antibody according to the present invention, as described herein, can reinforce the action of immunostimulatory ligands.

According to a further aspect, the present invention proposes a substance (in particular an anti-CEACAM1 antibody according to the present invention) for use in the therapy, i.e. treatment and/or prevention, of viral infections and/or viral infectious diseases, preferably in humans or nonhuman animals. The substance can be provided, in particular for use in inoculation against viral infectious diseases, or be used for inoculation against viral infectious diseases.

According to a further aspect, the present invention relates to a substance (in particular an anti-CEACAM1 antibody according to the present invention) for use in the therapy, i.e. treatment and/or prevention, of bacterial infections and/or bacterial infectious diseases, preferably in humans or non-human animals. The substance can be provided, in particular for use in inoculation against bacterial infectious diseases, or be used for inoculation against bacterial infectious diseases.

According to a further aspect, the present invention relates to a substance (in particular an anti-CEACAM1 antibody according to the present invention) for use in the therapy, i.e. treatment and/or prevention, of sepsis.

The substance is distinguished particularly in that it activates CEACAM1, preferably the expression and/or function of CEACAM1.

In particular, the substance is an anti-CEACAM1 antibody according to the present invention.

Preferably, the CEACAM1 is EACAM1 as per SEQ ID No. 1 (therefore the expression product of SEQ ID No. 1) or CEACAM1 as per SEQ ID No. 43.

In an alternative embodiment, the CEACAM1 is CEACAM1 as per SEQ ID No. 2 (therefore the expression product of SEQ ID No. 2). The CEACAM1 as per SEQ ID No. 2, in contrast to the CEACAM1 as per SEQ ID No. 1, possesses what is termed an interleukin-2 secretory sequence (IL-2 secretory sequence). This sequence leads to the protein pursuing the secretory pathway, and therefore being secreted by cells. Without this modification, the protein would not be secreted.

The expression and/or function of CEACAM1 can be activated by the substance provided according to the present invention in differing ways.

According to the present invention, it can be envisaged, for example, that the substance activates the expression of CEACAM1 at the nucleic acid level.

In addition, it can be envisaged that the substance activates the expression of CEACAM1 by activating an endogenous CEACAM1 promoter.

In addition, it can be provided that the substance activates the expression of CEACAM1 at the mRNA level.

In addition, it can be provided according to the present invention that the substance activates CEACAM1 at the protein level.

In a further embodiment, the substance is a polynucleotide which encodes a polypeptide or protein, wherein the polypeptide or protein activates the expression and/or function of CEACAM1.

The substance provided according to the present invention preferably binds, in particular forming a crosslinking, to CEACAM1. The crosslinking leads to the fact that CEACAM1 molecules congregate in the membrane and, by interaction with themselves or other signal proteins, develop their action in the cell.

In a preferred embodiment, the substance is a substance directed toward CEACAM1.

The substance can in addition be in particular directed toward inhibitors, biological precursors and/or variants, in particular isoforms, of CEACAM1.

In principle, the substance can be selected from the group consisting of anti-sense RNA, aptamers, mirror aptamers, antibodies, soluble binding partners, in particular soluble ligands, of CEACAM1, soluble receptors, small interfering RNA (siRNA), small hairpin RNA (shRNA), siRNA-containing particles (such as siRNA-containing calcium phosphate particles), shRNA-containing particles (such as shRNA-containing calcium phosphate particles), siRNA-containing vesicles (such as siRNA-containing liposomes), shRNA-containing vesicles (such as siRNA-containing liposomes) and ribozymes. Preferably, the siRNA and shRNA are present in the siRNA-containing particles and shRNA-containing particles in packaged form.

According to a particularly preferred embodiment, the substance is an antibody directed toward CEACAM1 (anti-CEACAM1 antibody, activating antibody).

The antibody, in a further embodiment, is a murine antibody or leporine antibody. In other words, it can be preferred according to the present invention if the antibody is a rabbit antibody, mouse antibody or rat antibody, i.e. is an antibody which has been produced by a rabbit, a mouse or a rat.

The antibody can have, in particular, a variable antibody heavy chain ($V_H$) domain which is selected from the group consisting of variable antibody heavy chain ($V_H$) domains of murine origin and variable antibody heavy chain ($V_H$) domains of leporine origin. In other words, it can be provided in particular according to the present invention that the antibody has a variable antibody heavy chain ($V_H$) domain which has been produced by a mouse, a rat or a rabbit.

In addition, the antibody can have in particular a variable antibody light chain ($V_L$) domain which is selected from the group consisting of variable antibody light chain ($V_L$) domain of murine origin and variable antibody light chain ($V_L$) domain of leporine origin. In other words, it can be provided according to the present invention, in particular, that the antibody has a variable antibody light chain ($V_L$) domain which has been produced from a mouse, a rat or a rabbit.

To improve the compatibility of the antibody, in a further embodiment, it can be provided that the antibody has constant antibody heavy chain ($C_H$) domains of human origin and/or a constant antibody light chain ($C_L$) domain of human origin.

According to a preferred embodiment, the antibody is a humanized antibody. In this embodiment, the constant antibody heavy chain ($C_H$) domain and also the constant antibody light chain ($C_L$) domain of the antibody are in each case of human origin, whereas the variable antibody heavy chain ($V_H$) domain and variable antibody light chain ($V_L$) domain of the antibody are in each case of xenogenic, in particular murine or leporine, origin.

The antibody preferably has a variable antibody heavy chain ($V_H$) domain which is selected from the group consisting of variable antibody heavy chain ($V_H$) domain as per SEQ ID No. 3, variable antibody heavy chain ($V_H$) domain as per SEQ ID No. 7 and variable antibody heavy chain ($V_H$) domain as per SEQ ID No. 11.

In a further preferred embodiment, the antibody has a variable antibody light chain ($V_L$) domain which is selected from the group consisting of variable antibody light chain ($V_L$) domain as per SEQ ID No. 5, variable antibody light chain ($V_L$) domain as per SEQ ID No. 9 and variable antibody light chain ($V_L$) domain as per SEQ ID No. 13.

Particularly preferably, the antibody has a variable antibody heavy chain ($V_H$) domain as per SEQ ID No. 3 and a variable antibody light chain ($V_L$) domain as per SEQ ID No. 5.

In an alternative embodiment, the antibody has a variable antibody heavy chain ($V_H$) domain as per SEQ ID No. 7 and a variable antibody light chain ($V_L$) domain as per SEQ ID No. 9.

According to a further alternative embodiment, the antibody has a variable antibody heavy chain ($V_H$) domain as per SEQ ID No. 11 and a variable antibody light chain (VL) domain as per SEQ ID No. 13.

In a preferred embodiment, the antibody has a variable antibody heavy chain ($V_H$) domain which is encoded by a nucleotide sequence which is selected from the group consisting of SEQ ID No. 4, SEQ ID No. 8 and SEQ ID No. 12.

According to a further preferred embodiment, the antibody has a variable antibody light chain ($V_L$) domain which is encoded by a nucleotide sequence which is selected from the group consisting of SEQ ID No. 6, SEQ ID No. 10 and SEQ ID No. 14.

In a particularly preferred embodiment, the antibody has a variable antibody heavy chain ($V_H$) domain which is encoded by a nucleotide sequence as per SEQ ID No. 4, and a variable antibody light chain (VL) domain which is encoded by a nucleotide sequence as per SEQ ID No. 6.

According to an alternative embodiment, the antibody has a variable antibody heavy chain ($V_H$) domain which is encoded by a nucleotide sequence as per SEQ ID No. 8, and a variable antibody light chain (VL) domain which is encoded by a nucleotide sequence as per SEQ ID No. 10.

According to a further alternative embodiment, the antibody has a variable antibody heavy chain ($V_H$) domain which is encoded by a nucleotide sequence as per SEQ ID No. 12, and a variable antibody light chain (VL) domain which is encoded by a nucleotide sequence as per SEQ ID No. 14.

In addition, the antibody is preferably a monoclonal antibody.

The antibody, in a further embodiment, can be an antibody that is produced by a B-cell hybridoma line (B-cell clone) which is selected from the group consisting of 6G5J, B3-17 and 18-20.

According to further embodiments, the substance provided according to the present invention can be a natural binding partner of CEACAM1 or a modified form of such a binding partner. For example, the substance can be selected from the group consisting of soluble UspA1 protein of *Moraxella catarrhalis*, modified UspA1 protein of *Moraxella catarrhalis*, soluble Opa protein of *Neisseria gonorrhoeae*, modified Opa protein of *Neisseria gonorrhoeae*, soluble variable P5 protein of *Haemophilus influenzae*, modified variable P5 protein of *Haemophilus influenzae*, modified Tim3, modified glycoprotein of hepatitis virus, modified *salmonella* surface protein and modified *Escherichia coli* surface protein.

In a preferred embodiment, the substance is the soluble protein UspA1 of *Moraxella catarrhalis* as per SEQ ID No. 15.

In a further embodiment, the substance is the soluble protein UspA1 of *Moraxella catarrhalis*, which is encoded by a nucleotide sequence as per SEQ ID No. 16.

In a further embodiment, the substance is the soluble protein Opa of *Neisseria gonorrhoeae* as per SEQ ID No. 17.

In a further embodiment, the substance is a soluble variable protein P5 of *Haemophilus influenzae* as per SEQ ID No. 18.

In a further embodiment, the substance is the soluble human recombinant CEACAM1 fusion protein as per SEQ ID No. 19.

In a further embodiment, the substance is the soluble human recombinant CEACAM1-fusion protein which is encoded by a nucleotide sequence as per SEQ ID No. 20.

The viral infections or infectious diseases are preferably selected from the group consisting of viral hepatitis, hepatitis B, hepatitis C, HIV infection, Aids, influenza, Poliomyelitis, virus-induced myocarditis, Epstein-Barr virus infections or infectious diseases such as glandular fever, herpes simplex, cytomegalie, rabies and Ebola.

According to a further aspect, the present invention relates to a substance for use in the therapy, i.e. treatment and/or prevention, of B-cell-dependent diseases, preferably in humans or nonhuman animals.

The substance is distinguished particularly in that it inhibits CEACAM1, preferably the expression and/or function of CEACAM1.

The expression and/or function of CEACAM1 can be inhibited by the substance provided according to the present invention in different ways.

According to the present invention, it can be provided that the substance inhibits the expression of CEACAM1 at the nucleic acid level.

In addition, it can be provided that the substance inhibits the expression of CEACAM1 by activating an endogenous CEACAM1 promoter.

In addition, it can be provided that the substance inhibits the expression of CEACAM1 at the mRNA level.

In addition, it can be provided according to the present invention that the substance inhibits CEACAM1 at the protein level.

In a further embodiment, the substance is a polynucleotide which is encoded by a polypeptide or protein, wherein the polypeptide or protein inhibits the expression and/or function of CEACAM1.

The B-cell-dependent diseases are, preferably, autoimmune diseases and/or inflammatory diseases.

Preferably, the autoimmune diseases or inflammatory diseases are selected from the group consisting of Myasthenia gravis, systemic Lupus erythematodes, autoimmune thyroiditis, dermatitis such as atopic dermatitis and/or eczema, psoriasis, Sjögren's syndrome, Crohn's disease, conjunctivitis, Cholitis ulcerosa, bronchial asthma, allergic asthma, Lupus erythematodes such as cutaneous Lupus erythematodes, allergies, Wegener's disease (granulomatosis polyangiitis), Stevens-Johnson syndrome, sprue, Basedow's disease, sarcoidosis, primary biliary cirrhosis, autoimmune hepatitis, diabetes mellitus such as diabetes mellitus type 1 and/or diabetes mellitus type 2, arthritis such as rheumatoid arthritis, osteoarthritis and/or psoriasis arthritis, multiple sclerosis and B-cell lymphoma.

With respect to further features and advantages of the substance, to avoid unnecessary repetitions, reference is made in its entirety to the details made in the context of the first aspect of the present invention. The embodiments and advantages described there apply accordingly also to the substance according to the second aspect of the present invention.

According to a further aspect, the present invention relates to a drug, preferably for use in the therapy, i.e. treatment and/or prevention, of viral infections, viral infectious diseases and/or B-cell-dependent diseases, in particular in human or nonhuman animals.

The drug is distinguished particularly in that it contains at least one substance as per an aspect of the present invention cited above.

Preferably, the drug additionally contains a pharmaceutically compatible carrier material. As suitable carrier materials, in principle inorganic and/or organic carrier materials come into consideration. For example, the carrier can be selected from the group consisting of water, vegetable oils, fatty compounds, benzyl alcohols, alkylene glycols, polyethylene glycols, glycerol triacetate, gelatin, carbohydrates such as lactose and/or starch, magnesium stearate, tallow, Vaseline and mixtures thereof. With respect to suitable carrier materials, reference may be made for example to the textbook by Bauer et al. (Lehrbuch der Pharmazeutischen Technologie [Textbook of Pharmaceutical Technology], 6th edition, 1999, Wissenschaftliche Verlagsgesellschaft mbH, Stuttgart, Germany) and also to the textbook by Rowe et al. (Handbook of Pharmaceutical Excipients, 5th edition, 2006, Pharmaceutical Press and American Pharmacists Association), the disclosure of which with respect to the carrier materials described there is incorporated into the contents of the present description by explicit reference.

According to the present invention, it can additionally be provided that the drug in addition contains at least one auxiliary which is selected, for example, from the group consisting of lubricants, preservatives, stabilizers, resorption accelerators, wetting agents, emulsifiers, salts for affecting the osmotic pressure, buffer substances, dyes, flavorings, perfumes, further active ingredients and mixtures thereof.

The drug can be, in particular, an inoculate against viral infectious diseases.

With respect to further features and advantages of the drug, in particular of the at least one substance, the viral infections, viral infectious diseases and/or B-cell-dependent diseases, to avoid unnecessary repetitions, reference is made in its entirety to the description to date. The embodiments and advantages described there with respect to the substance and also the viral infections, viral infectious diseases and/or B-cell-dependent disease mentioned there apply accordingly also to the drug according to the third aspect of the present invention.

According to a further aspect, the present invention relates to a substance for use in the diagnosis of viral infections, viral infectious disease and/or B-cell-dependent diseases, preferably in humans or nonhuman animals.

The substance is distinguished particularly in that it is provided or used for detecting CEACAM1, preferably for detecting the expression and/or function of CEACAM1.

Detecting the expression and/or function of CEACAM1 by the substance provided according to the present invention can proceed in various ways.

According to the present invention, it can be provided, for example, that the substance is used for detecting the expression of CEACAM1 at the nucleic acid level.

In addition, it can be provided that the substance is used for detecting the expression of CEACAM1 at the mRNA level.

In a further embodiment, the substance is a polynucleotide which encodes a polypeptide or protein, wherein the polypeptide or protein inhibits the expression and/or function of CEACAM1.

In a preferred embodiment, the substance is a substance directed against CEACAM1.

Particularly preferably, the substance directed against CEACAM1 is an antibody (anti-CEACAM1 antibody). Such an antibody can be used in the context of detection methods known to those skilled in the art, for example ELISA (Enzyme-Linked Immunosorbent Assay). In the case of ELISA, a specific antibody directed toward the antigen (CEACAM1) that is to be determined is bound to a carrier material, for example cellulose or polystyrene. On the carrier material, after an incubation with a sample that contains CEACAM1 as antigen, immune complexes form. In a subsequent step, to these immune complexes are added a labeled antibody which is likewise directed against the antigen CEACAM1, but expediently binds at a different site than the antibody bound to the carrier material. This labeled antibody is usually an antibody-enzyme conjugate, wherein the enzyme is generally alkali phosphatase or horseradish peroxide. By adding the labeled antibody, ultimately ternary complexes form from the antigen (CEACAM1) and the two antibodies directed in each case against the antigen (CEACAM1). These ternary complexes may be visualized by adding chromogenic substrates, such as, for example, para-nitrophenol. The concentration of CEACAM1 in the sample can be determined therefrom via photometric determination of the immune complex bound marker enzymes by comparison with standards of known antigen concentration. It is likewise possible to use antibodies directed against CEACAM1 (anti-CEACAM1 antibodies) in the context of ELISPOT methods. The methods mentioned in this paragraph are sufficiently familiar to those skilled in the art so that further explanations are dispensed with.

In a further embodiment, the substance can be an oligonucleotide which is suitable, for example by means of what is termed the polymerase chain reaction (PCR), to amplify selectively certain DNA sections of CEACAM1, and in this manner to produce a preferably quantitative detection of CEACAM1.

According to a further embodiment, the substance can be an oligonucleotide or polynucleotide which is hybridized with CEACAM1 under stringent conditions. With the aid of such oligonucleotides or polynucleotides, for example Southern Blots or Northern Blots can be carried out, in order in this manner to detect the DNA or RNA content of CEACAM1. In this manner, for example the transcription rate of CEACAM1 may also be investigated. Corresponding methods are likewise sufficiently familiar to those skilled in the art such that further details are likewise dispensed with at this point.

With respect to further features and advantages of the substance and also with respect to possible viral infections, viral infectious diseases and/or B-cell-dependent diseases, to avoid unnecessary repetitions, likewise reference is made completely to the description above. The embodiments and advantages described there with respect to the substance and also the viral infections, viral infectious diseases and/or B-cell-dependent diseases mentioned there apply accordingly also to the substance according to the fourth aspect of the present invention.

According to a further aspect, the present invention relates to a diagnostic agent, preferably for use in the diagnosis of viral infections, viral infectious diseases and/or B-cell-dependent diseases, in particular in humans or nonhuman animals.

The diagnostic agent is distinguished particularly in that it contains at least one substance according to an above-mentioned aspect of the present invention.

With respect to further features and advantages of the diagnostic agent, in particular of the at least one substance, the viral infections, viral infectious diseases and/or B-cell-dependent diseases, likewise reference is made in its entirety to the description to date. The embodiments and advantages described there with respect to the substance and also the viral infections, viral infectious diseases and/or B-cell-dependent diseases mentioned there also apply similarly to the diagnostic agent as per the fifth aspect of the present invention.

According to a further aspect, the present invention relates to an antibody directed against CEACAM1 (anti-CEACAM1 antibody).

The antibody is distinguished particularly in that it comprises a variable antibody heavy chain ($V_H$) domain selected from the group consisting of variable antibody heavy chain ($V_H$) domain as per SEQ ID No. 3, variable antibody heavy chain ($V_H$) domain as per SEQ ID No. 7 and variable antibody heavy chain ($V_H$) domain as per SEQ ID No. 11, and/or a variable antibody light chain ($V_L$) domain, selected from the group consisting of variable antibody light chain ($V_L$) domain as per SEQ ID No. 5, variable antibody light chain ($V_L$) domain as per SEQ ID No. 9 and variable antibody light chain ($V_L$) domain as per SEQ ID No. 13.

The antibody, in a preferred embodiment, has a variable antibody heavy chain ($V_H$) domain as per SEQ ID No. 3 and a variable antibody light chain ($V_L$) domain as per SEQ ID No. 5.

In an alternative embodiment, the antibody has a variable antibody heavy chain ($V_H$) domain as per SEQ ID No. 7 and a variable antibody light chain ($V_L$) domain as per SEQ ID No. 9.

In a further alternative embodiment, the antibody has a variable antibody heavy chain ($V_H$) domain as per SEQ ID No. 11 and a variable antibody light chain ($V_L$) domain as per SEQ ID No. 13.

The antibody, in a preferred embodiment, is a murine antibody or leporine antibody. In other words, it is preferred according to the present invention when the antibody is a mouse antibody, rat antibody or rabbit antibody, i.e. an antibody which has been produced by a mouse, a rat, or a rabbit.

In particular, the variable antibody heavy chain ($V_H$) domain can be selected from the group consisting of variable antibody heavy chain ($V_H$) domain of murine origin and variable antibody heavy chain ($V_H$) domain of leporine origin. In other words, according to the present invention it can be provided in particular that the variable antibody heavy chain ($V_H$) domain has been produced by a mouse, a rat or a rabbit.

In addition, in particular the variable antibody light chain ($V_L$) domain can be selected from the group consisting of variable antibody light chain ($V_L$) domain of murine origin and variable antibody light chain ($V_L$) domain of leporine origin. In other words, according to the present invention it can be provided in particular that the variable antibody light chain ($V_L$) domain has been produced by a mouse, a rat or a rabbit.

To improve the compatibility of the antibody, in a further embodiment, it can be provided that the antibody has a constant antibody heavy chain ($C_H$) domain of human origin and/or a constant antibody light chain ($C_L$) domain of human origin.

According to a further embodiment, the antibody is a humanized antibody. In this embodiment, the constant antibody heavy chain ($C_H$) domain and also the constant antibody light chain ($C_L$) domain of the antibody are each of human origin, whereas the variable antibody heavy chain ($V_H$) domain and variable antibody light chain ($V_L$) domain of the antibody are each of xenogenic origin, in particular murine or leporine origin.

In addition, the antibody is preferably a monoclonal antibody.

The antibody can be, in particular, an antibody which is produced by a B cell hybridoma line (B cell clone), which is selected from the group consisting of 6G5J, B3-17 and 18-20.

The antibody is in addition preferably an antibody for use in medicine.

In principle, the antibody can be a diagnostic and/or therapeutic antibody. Correspondingly, the antibody can be provided for use in the diagnosis and/or therapy, i.e. treatment and/or prevention, of diseases.

In principle, the antibody can be an antibody for use in the diagnosis of viral infections, viral infectious diseases, B-cell-dependent diseases and/or tumors.

Preferably, the antibody can be an antibody for use in the therapy, i.e. treatment and/or prevention, of diseases.

Particularly preferably, the antibody is provided for use in the therapy, i.e. treatment and/or prevention, of viral infections, viral infectious diseases, B-cell-dependent diseases and/or tumors. In other words, the antibody, according to a particularly preferred embodiment, is an antibody for use in the therapy, i.e. treatment and/or prevention, of viral infections, viral infectious diseases, B-cell-dependent diseases and/or tumors.

The tumors can in principle be benign tumors or malignant tumors.

Preferably, the tumors are malignant tumors. The malignant tumors can in this case be selected, in particular, from the group consisting of carcinomas, melanomas, plastomas, lymphomas and sarcomas.

The carcinomas can be selected from the group consisting of anal carcinoma, bronchial carcinoma, pulmonary carcinoma, endometrial carcinoma, gall bladder carcinoma, hepatocellular carcinoma, scrotal carcinoma, colorectal carcinoma, laryngeal carcinoma, esophageal cancer, stomach cancer, breast cancer, renal carcinoma, ovarian cancer, tumor of the pancreas, pharyngeal carcinoma, carcinoma of the prostate, thyroid carcinoma and cervical carcinoma.

The sarcomas can be selected from the group consisting of angiosarcoma, chondrosarcoma, Ewing sarcoma, fibrosarcoma, Kaposi's sarcoma, liposarcoma, leiomyosarcoma, malign fibrous histiocytoma, neurogenic sarcoma, osteosarcoma and rhabdomyosarcoma.

With respect to further features and advantages of the antibody, in particular of possible viral infections, viral infectious diseases and/or B-cell-dependent diseases, for the diagnosis and/or therapy of which the antibody can be applied or used, to avoid unnecessary repetition, likewise reference is made in its entirety to the description hereinbefore.

According to a further aspect, the present invention relates to a further antibody directed against CEACAM1 (anti-CEACAM1 antibody).

The antibody is distinguished particularly in that it comprises a variable antibody heavy chain ($V_H$) domain which is encoded by a nucleotide sequence that is selected from the group consisting of SEQ ID No. 4, SEQ ID No. 8 and SEQ ID No. 12, and/or a variable antibody light chain (VL) domain which is encoded by a nucleotide sequence that is selected from the group consisting of SEQ ID No. 6, SEQ ID No. 10 and SEQ ID No. 14.

Particularly preferably, the antibody comprises a variable antibody heavy chain ($V_H$) domain which is encoded by a nucleotide sequence as per SEQ ID No. 4, and a variable antibody light chain ($V_L$) domain which is encoded by a nucleotide sequence as per SEQ ID No. 6.

In an alternative embodiment, the antibody comprises a variable antibody heavy chain ($V_H$) domain which is encoded by a nucleotide sequence as per SEQ ID No. 8 and a variable antibody light chain ($V_L$) domain which is encoded by a nucleotide sequence as per SEQ ID No. 10.

In a further alternative embodiment, the antibody comprises a variable antibody heavy chain ($V_H$) domain which is encoded by a nucleotide sequence as per SEQ ID No. 12, and a variable antibody light chain ($V_L$) domain which is encoded by a nucleotide sequence as per SEQ ID No. 14.

The antibody, in a preferred embodiment, is a murine antibody or leporine antibody. In other words, it is preferred according to the present invention when the antibody is a mouse antibody, rat antibody or rabbit antibody, i.e. an antibody which has been produced by a mouse, a rat or a rabbit.

In particular, the variable antibody heavy chain ($V_H$) domain can be selected from the group consisting of variable antibody heavy chain ($V_H$) domain of murine origin and variable antibody heavy chain ($V_H$) domain of leporine origin. In other words, according to the present invention it can be provided, in particular, that the variable antibody heavy chain ($V_H$) domain has been produced by a mouse, a rat or a rabbit.

In addition, in particular the variable antibody light chain ($V_L$) domain can be selected from the group consisting of variable antibody light chain ($V_L$) domain of murine origin and variable antibody light chain ($V_L$) domain of leporine origin. In other words, according to the present invention it can be provided, in particular, that the variable antibody light chain ($V_L$) domain has been produced by a mouse, a rat or a rabbit.

To improve the compatibility of the antibody, in a further embodiment it can be provided that the antibody comprises a constant antibody heavy chain ($C_H$) domain of human origin and/or a constant antibody light chain ($C_L$) domain of human origin.

According to a further embodiment, the antibody is a humanized antibody. In this embodiment, the constant antibody heavy chain ($C_H$) domain and also the constant antibody light chain ($C_L$) domain of the antibody are in each case of human origin, whereas the variable antibody heavy chain ($V_H$) domain and variable antibody light chain ($V_L$) domain of the antibody are in each case of xenogenic origin, in particular of murine or leporine origin.

In addition, the antibody is preferably a monoclonal antibody.

The antibody can in particular be an antibody that is produced by a B cell hybridoma line (B cell clone) that is selected from the group consisting of 6G5J, B3-17 and 18-20.

The antibody is in addition preferably an antibody for application in medicine.

In principle, the antibody can be a diagnostic and/or therapeutic antibody. Correspondingly, the antibody can be provided for application in the diagnosis and/or therapy, i.e. treatment and/or prevention, of diseases.

In principle, the antibody can be an antibody for application in the diagnosis of viral infections, viral infectious diseases, B-cell-dependent diseases and/or tumors.

Preferably, the antibody is an antibody for application in the therapy, i.e. treatment and/or prevention, of diseases.

Particularly preferably, the antibody is provided for application in the therapy, i.e. treatment and/or prevention, of viral infections, viral infectious diseases, B-cell-dependent diseases and/or tumors. In other words, the antibody, according to a particularly preferred embodiment, is an antibody for application in the therapy, i.e. treatment and/or prevention, of viral infections, viral infectious diseases, B-cell-dependent diseases and/or tumors.

With respect to further features and advantages of the antibody, in particular of possible viral infections, viral infectious diseases, B-cell-dependent diseases and/or tumors, for the diagnosis and/or therapy of which the antibody can be used or applied, to avoid unnecessary repetition, likewise reference is made in its entirety to the description hereinbefore.

According to a further aspect, the present invention relates to a variable antibody heavy chain ($V_H$) domain of an antibody directed against CEACAM1 (anti-CEACAM1 antibody).

The variable antibody heavy chain ($V_H$) domain is selected from the group consisting of antibody heavy chain ($V_H$) domain as per SEQ ID No. 3, variable antibody heavy chain ($V_H$) domain as per SEQ ID No. 7 and variable antibody heavy chain ($V_H$) domain as per SEQ ID No. 11.

The variable antibody heavy chain ($V_H$) domain, in a preferred embodiment, is of murine or leporine origin. In other words, it is preferred according to the present invention when the variable antibody heavy chain ($V_H$) domain has been produced by a mouse, a rat or a rabbit.

The antibody is preferably a monoclonal antibody.

With respect to further features and advantages of the variable antibody heavy chain ($V_H$) domain, and also of the antibody, to avoid unnecessary repetition, likewise reference is made in its entirety to the description hereinbefore. The embodiments and also advantages in respect of the variable antibody heavy chain ($V_H$) domain and also the antibody also apply accordingly to the variable antibody heavy chain ($V_H$) domain according to the eighth aspect of the present invention.

According to a further aspect, the present invention relates to a variable antibody light chain ($V_L$) domain of an antibody directed against CEACAM1 (anti-CEACAM1 antibody).

The variable antibody light chain ($V_L$) domain is selected from the group consisting of variable antibody light chain ($V_L$) domain as per SEQ ID No. 5, variable antibody light chain ($V_L$) domain as per SEQ ID No. 9 and variable antibody light chain ($V_L$) domain as per SEQ ID No. 13.

The variable antibody light chain ($V_L$) domain, in a preferred embodiment, is of murine or leporine origin. In other words, it is preferred according to the present invention when the variable antibody light chain ($V_L$) domain has been produced by a mouse, a rat or a rabbit.

The antibody is preferably a monoclonal antibody.

With respect to further features and advantages of the variable antibody light chain ($V_L$) domain and also of the antibody, to avoid unnecessary repetition, likewise reference is made in its entirety to the description hereinbefore. The embodiments and advantages described there in relation to the variable antibody light chain ($V_L$) domain and the antibody also apply accordingly to the variable antibody light chain ($V_L$) domain according to the ninth aspect of the present invention.

According to a further aspect, the present invention relates to an isolated nucleic acid which encodes a variable antibody heavy chain ($V_H$) domain of an antibody directed against CEACAM1 (anti-CEACAM1 antibody).

The nucleic acid and also the antibody are preferably a human nucleic acid or human antibody. The antibody is preferably a monoclonal antibody.

The nucleic acid comprises a nucleotide sequence or consists of a nucleotide sequence that is selected from the group consisting of SEQ ID No. 4 and SEQ ID No. 8 and SEQ ID No. 12.

With respect to further features and advantages of the nucleic acid, to avoid unnecessary repetition, likewise reference is made in its entirety to the description given before. The embodiments and advantages described there in particular in relation to the variable antibody heavy chain ($V_H$) domain and the antibody also apply correspondingly to the nucleic acid according to the tenth aspect of the present invention.

According to a further aspect, the present invention relates to an isolated nucleic acid which encodes a variable antibody light chain ($V_L$) domain of an antibody directed against CEACAM1 (anti-CEACAM1 antibody).

The nucleic acid and also the antibody are preferably a human nucleic acid and/or human antibody. The antibody is preferably a monoclonal antibody.

The nucleic acid comprises a nucleotide sequence or consists of a nucleotide sequence which is selected from the group consisting of SEQ ID No. 6, SEQ ID No. 10 and SEQ ID No. 14.

With respect to further features and advantages of the nucleic acid, to avoid unnecessary repetition, likewise reference is made in its entirety to the description hereinbefore. The embodiments and advantages described there in particular in relation to the variable antibody light chain ($V_L$) domain and also the antibody also apply correspondingly to the nucleic acid according to the eleventh aspect of the present invention.

According to a further aspect, the present invention relates to a hybridoma cell which produces an antibody according to an abovementioned aspect of the present invention.

The hybridoma cell is preferably formed by fusion of B-lymphocytes, which originate from an experimental animal immunized against CEACAM1 and produce antibodies directed against CEACAM1 (anti-CEACAM1 antibodies), and myeloma cells. The experimental animal can be selected from the group consisting of mouse, rat, rabbit and goat. Myeloma cells are taken to mean in general cells (plasma cells) of a cell line obtained from a myeloma (plasmacytoma) of an animal. The myeloma cells can be obtained in the context of the present invention from the myeloma of a mouse, a rat, a rabbit or a goat.

Preferably, the myeloma cells are cells from the mouse myeloma cell line NS1/0.

The hybridoma cell preferably belongs to a B cell hybridoma line (B cell clone) that is selected from the group consisting of 6G5J, B3-17 and 18-20.

With regard to further features and advantages of the hybridoma cell, to avoid unnecessary repetition, likewise reference is made in its entirety to the description hereinbefore. The embodiments and advantages described there in particular with respect to the antibody apply correspondingly also to the hybridoma cell according to the twelfth aspect of the present invention.

According to a further aspect, the present invention relates to a method for producing an antibody directed against CEACAM1 (anti-CEACAM1 antibody), in particular an antibody according to the sixth or seventh aspect of the present invention.

The method has the following steps:
(a) fusing B cells which originate from an experimental animal immunized against an antigen, and myeloma cells, forming hybridoma cells,
(b) selecting the hybridoma cells,
(c) isolating hybridoma cells that produce antibodies directed against the antigen.

As compared with methods of the type in question, the method according to the present invention is particularly distinguished in that the antigen is selected from the group consisting of CEACAM1 as per SEQ ID No. 1, CEACAM1 as per SEQ ID No. 2 (therefore the expression product of SEQ ID No. 1 or 2) and/or CEACAM1 as per SEQ ID No. 43, a fragment, in particular epitope, of SEQ ID No. 1 and a fragment, in particular epitope, of SEQ ID No. 2 (therefore the expression product of SEQ ID No. 1 or 2) and/or SEQ ID No. 43.

In a preferred embodiment, the antigen is CEACAM1 as per SEQ ID No. 1 (therefore the expression product of SEQ ID No. 1) and/or CEACAM1 as per SEQ ID No. 43 or a fragment, in particular epitope, thereof.

In an alternative embodiment, the antigen is CEACAM1 as per SEQ ID No. 2 (therefore the expression product of SEQ ID No. 2) or a fragment, in particular epitope, thereof.

The experimental animal, in a preferred embodiment, is a mouse, a rat, a rabbit or a goat. The use of a mouse as an experimental animal, however, is particularly preferred according to the present invention.

The B cells can be fused with cells from a cell line obtained from a myeloma of a mouse, a rat, a rabbit or a goat.

Preferably, the B cells are fused with cells of the mouse myeloma cell line NS1/0.

The step a), that is to say the cell fusion, can be carried out using polyethylene glycol (PEG). For this purpose, the B cells and myeloma cells are added together into an aqueous polyethylene glycol-containing fusion solution and centrifuged. Since the water is substantially bound by PEG, the cell membranes are brought together in close contact, as a result of which spontaneous fusion of the cell membranes is achieved.

Alternatively, step a) can be performed under the action of electrical voltage, i.e. as what is termed electrofusion. During the electrofusion, by means of electrical pulses, the cell membranes are "melted" locally, as a result of which a coalescence of the cell membranes is achieved. In order to support the fusion, small amounts of PEG can be added.

The B cells and the myeloma cells are, in a further embodiment, fused in a ratio of 5:1 (B cells to myeloma cells).

Step b) in a preferred embodiment is carried out using a selective medium, in which only hybridoma cells are capable of surviving. As a selective medium, preferably, what is termed HAT medium is used. The HAT medium contains the chemical substances hypoxanthine, aminopterine and thymidine. Hypoxanthine is a precursor for essential molecules (purines) that are required for the buildup of deoxyribonucleic acid (DNA). For the conversion thereof, however, the enzyme hypoxanthine-guanine phosphoribosyl transferase (HGPRT) is necessary. Since, in the fusion a myeloma cell line is used, from which precisely this enzyme is missing or is present in inactive form, individual myeloma cells are therefore not capable of survival in this medium. Spleen cells, in contrast, possess HGPRT, but are not themselves capable of survival, and rapidly die off in the culture medium. Only hybridoma cells can be cultured, since they possess the immortality of the myeloma cells and also the HGPRT genes of the spleen cells. Aminopterine serves only for blocking other purine synthesis pathways. Since, as a result, the essential thymidine can no longer be produced de novo, it must be added to the medium.

Step c) is preferably carried out by means of ELISA (Enzyme-linked immunosorbant assay) test or by continuous-flow cytometry.

In a further embodiment, the isolated hybridoma cells are expanded. This ensures that a sufficiently large number of hybridoma cells are available that produce the antibody directed against CEACAM1 (anti-CEACAM1 antibody).

With respect to further features and advantages of the method, in particular the hybridoma cells, the antigen and also the antibody, reference is made in its entirety to the details given hereinbefore and also in the example section. The embodiments and advantages described there in particular in respect of the hybridoma cell, the antigen and also the antibody, also apply correspondingly to the method as per the thirteenth aspect of the present invention.

The other sequences shown in the present application are as follows:

SEQ ID No. 1: human CEACAM1 (Hu-CEACAM1 + Hu-IgG-Fc2) (Homo sapiens):
CAGCTGACCACCGAGAGCATGCCCTTCAACGTGGCCGAGGGCAAGGAG

GTGCTGCTGCTGGTGCACAACCTGCCCCAGCAGCTGTTCGGCTACAGCTG

GTACAAGGGCGAGAGGGTGGACGGCAACAGGCAGATCGTGGGCTACGCCA

TCGGCACCCAGCAGGCCACCCCCGGCCCCGCCAACAGCGGCAGGGAGACC

ATCTACCCCAACGCCAGCCTGCTGATCCAGAACGTGACCCAGAACGACAC

CGGCTTCTACACCCTGCAGGTGATCAAGAGCGACCTGGTGAACGAGGAGG

CCACCGGCCAGTTCCACGTGTACCCCGAGCTGCCCAAGCCCAGCATCAGC

AGCAACAACAGCAACCCCGTGGAGGACAAGGACGCCGTGGCCTTCACCTG

CGAGCCCGAGACCCAGGACACCACCTACCTGTGGTGGATCAACAACCAGA

GCCTGCCCGTGAGCCCCAGGCTGCAGCTGAGCAACGGCAACAGGACCCTG

ACCCTGCTGAGCGTGACCAGGAACGACACCGGCCCCTACGAGTGCGAGAT
CCAGAACCCCGTGAGCGCCAACAGGAGCGACCCCGTGACCCTGAACGTGA
CCTACGGCCCCGACACCCCCACCATCAGCCCCAGCGACACCTACTACAGG
CCCGGCGCCAACCTGAGCCTGAGCTGCTACGCCGCCAGCAACCCCCCCGC
CCAGTACAGCTGGCTGATCAACGGCACCTTCCAGCAGAGCACCCAGGAGC
TGTTCATCCCCAACATCACCGTGAACAACAGCGGCAGCTACACCTGCCAC
GCCAACAACAGCGTGACCGGCTGCAACAGGACCACCGTGAAGACCATCAT
CGTGACCGAGCTGAGCCCCGTGGTGGCCAAGCCCCAGATCAAGGCCAGCA
AGACCACCGTGACCGGCGACAAGGACAGCGTGAACCTGACCTGCAGCACC
AACGACACCGGCATCAGCATCAGGTGGTTCTTCAAGAACCAGAGCCTGCC
CAGCAGCGAGAGGATGAAGCTGAGCCAGGGCAACACCACCCTGAGCATCA
ACCCCGTGAAGAGGGAGGACGCCGGCACCTACTGGTGCGAGGTGTTCAAC
CCCATCAGCAAGAACCAGAGCGACCCCATCATGCTGAACGTGGAGTGCCC
ACCTTGCCCAGCACCACCTGTGGCAGGACCTTCAGTCTTCCTCTTCCCCC
CAAAACCCAAGGACACCCTCATGATCTCCCGGACCCCTGAGGTCACATGC
GTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGC
AGTACAACAGCACGTACCGTGTGGTCAGCGTCCTCACCGTCCTGCACCAG
GACTGGCTGAATGGCAAGGAGTACAAGTGCAAGGTCTCCAACAAAGGCCT
CCCATCCTCCATCGAGAAAACCATCTCCAAAGCCAAAGGGCAGCCCCGAG
AACCACAGGTGTACACCCTGCCCCCATCCCGGGAGGAGATGACCAAGAAC
CAGGTCAGCCTGACCTGCCTGGTCAAAGGCTTCTATCCCAGCGACATCGC
CGTGGAGTGGGAGAGCAATGGGCAGCCGGAGAACAACTACAAGACCACGC
CTCCCGTGCTGGACTCCGACGGCTCCTTCTTCCTCTACAGCAAGCTCACC
GTGGACAAGAGCAGGTGGCAGCAGGGGAACGTCTTCTCATGCTCCGTGAT
GCATGAGGCTCTGCACAACCACTACACGCAGAAGAGCCTCTCCCTGTCTC
CGGGTAAA

SEQ ID No. 2: human CEACAM1 (IL2 Secretory
sequence + Hu-CEACAM1 + Hu-IgG-Fc2)
(Homo sapiens):
CCTGAGATCACCGGCGAAGGAGGGCCACCATGTACAGGATGCAACTCC
TGTCTTGCATTGCACTAAGTCTTGCACTTGTCACGAATTCGCAGCTGACC
ACCGAGAGCATGCCCTTCAACGTGGCCGAGGGCAAGGAGGTGCTGCTGCT
GGTGCACAACCTGCCCCAGCAGCTGTTCGGCTACAGCTGGTACAAGGGCG
AGAGGGTGGACGGCAACAGGCAGATCGTGGGCTACGCCATCGGCACCCAG
CAGGCCACCCCCGGCCCCGCCAACAGCGGCAGGGAGACCATCTACCCCAA
CGCCAGCCTGCTGATCCAGAACGTGACCCAGAACGACACCGGCTTCTACA
CCCTGCAGGTGATCAAGAGCGACCTGGTGAACGAGGAGGCCACCGGCCAG
TTCCACGTGTACCCCGAGCTGCCCAAGCCCAGCATCAGCAGCAACAACAG
CAACCCCGTGGAGGACAAGGACGCCGTGGCCTTCACCTGCGAGCCCGAGA
CCCAGGACACCACCTACCTGTGGTGGATCAACAACCAGAGCCTGCCCGTG
AGCCCCAGGCTGCAGCTGAGCAACGGCAACAGGACCCTGACCCTGCTGAG CGTGACCAGGAACGACACCGGCCCCTACGAGTGCGAGATCCAGAACCCCG
TGAGCGCCAACAGGAGCGACCCCGTGACCCTGAACGTGACCTACGGCCCC
GACACCCCCACCATCAGCCCCAGCGACACCTACTACAGGCCCGGCGCCAA
CCTGAGCCTGAGCTGCTACGCCGCCAGCAACCCCCCCGCCCAGTACAGCT
GGCTGATCAACGGCACCTTCCAGCAGAGCACCCAGGAGCTGTTCATCCCC
AACATCACCGTGAACAACAGCGGCAGCTACACCTGCCACGCCAACAACAG
CGTGACCGGCTGCAACAGGACCACCGTGAAGACCATCATCGTGACCGAGC
TGAGCCCCGTGGTGGCCAAGCCCCAGATCAAGGCCAGCAAGACCACCGTG
ACCGGCGACAAGGACAGCGTGAACCTGACCTGCAGCACCAACGACACCGG
CATCAGCATCAGGTGGTTCTTCAAGAACCAGAGCCTGCCCAGCAGCGAGA
GGATGAAGCTGAGCCAGGGCAACACCACCCTGAGCATCAACCCCGTGAAG
AGGGAGGACGCCGGCACCTACTGGTGCGAGGTGTTCAACCCCATCAGCAA
GAACCAGAGCGACCCCATCATGCTGAACGTGGAGTGCCCACCTTGCCCAG
CACCACCTGTGGCAGGACCTTCAGTCTTCCTCTTCCCCCCAAAACCCAAG
GACACCCTCATGATCTCCCGGACCCCTGAGGTCACATGCGTGGTGGTGGA
CGTGAGCCACGAAGACCCTGAGGTCAAGTTCAACTGGTACGTGGACGGCG
TGGAGGTGCATAATGCCAAGACAAAGCCGCGGGAGGAGCAGTACAACAGC
ACGTACCGTGTGGTCAGCGTCCTCACCGTCCTGCACCAGGACTGGCTGAA
TGGCAAGGAGTACAAGTGCAAGGTCTCCAACAAAGGCCTCCCATCCTCCA
TCGAGAAAACCATCTCCAAAGCCAAAGGGCAGCCCCGAGAACCACAGGTG
TACACCCTGCCCCCATCCCGGGAGGAGATGACCAAGAACCAGGTCAGCCT
GACCTGCCTGGTCAAAGGCTTCTATCCCAGCGACATCGCCGTGGAGTGGG
AGAGCAATGGGCAGCCGGAGAACAACTACAAGACCACGCCTCCCGTGCTG
GACTCCGACGGCTCCTTCTTCCTCTACAGCAAGCTCACCGTGGACAAGAG
CAGGTGGCAGCAGGGGAACGTCTTCTCATGCTCCGTGATGCATGAGGCTC
TGCACAACCACTACACGCAGAAGAGCCTCTCCCTGTCTCCGGGTAAA SEQ ID No. 3: anti-human CEACAM1 antibody
(clone 6G5J) - heavy chain (V-D-J-REGION)
(Mus musculus):
KPGETVKISCKTSGYIFRNYGMKWVKQAPGKGLKWMGWINTYTGEPTY
ADDFKGRFAFSLETSASTAYLQINNLKNEDMATYFCARRGM**ITTSNYALD
N**WGQGTSVTVSS SEQ ID No. 4: anti-human CEACAM1 antibody
(clone 6G5J) - heavy chain (V-D-J-REGION)
(Mus musculus):
aagcctggag agacagtcaa gatctcctgc aagacttctg
ggtatatatt cagaaactat ggaatgaaat gggtgaagca
ggctccagga aagggtttaa agtggatggg ctggataaac
acctatactg gagagccaac atatgctgat gacttcaagg
gacggtttgc cttctctttg gaaacctctg ccagcactgc
ctatttgcag atcaacaacc tcaaaaatga ggacatggct
acatatttct gtgcaagaag ggggatgatt acgacgagta
attatgctct ggacaactgg ggtcaaggaa cctcagtcac
cgtctcctca g SEQ ID No. 5: anti-human CEACAM1 antibody
(clone 6G5J) - light chain (V-J-REGION)
(Mus musculus):
SSLSASLGDRVTISCRASQDISNYLNWYQQKPDGTIKLLIYYTSKLHSGV

PSRFSGSGSGTDYSLTISNLDQEDIATYFCQQGNTLPWTFGGGTKLEIK

SEQ ID No. 6: anti-human CEACAM1 antibody
(clone 6G5J) - light chain (V-J-REGION)
(Mus musculus):
tcctccctgt ctgcctctct gggagacaga gtcaccatca gttgcagggc aagtcaggac attagcaatt atttaaactg gtatcagcag aaaccagatg gaactattaa actcctgatc tactacacat caaagttaca ctcaggagtc ccatcaagat tcagtggcag tgggtctgga acagattatt ctctcaccat tagcaacctg gaccaggaag atattgccac ttacttttgc caacagggta atactcttcc gtggacgttc ggtggaggca ccaagctgga aatcaaac SEQ ID No. 7: anti-human CEACAM1 antibody
(clone 18-20) - heavy chain (V-D-J Region)
(Mus musculus):
KPGETVKISCKASGYTFTVYGMNWVKQAPGKDLKWMGWINTYTGEPTY

ADDFKGRFAFSLETSASTAYLQINNLKNEDMATYFCARKAFYRYDGGMDY

WGQGTSVTVSS

SEQ ID No. 8: anti-human CEACAM1 antibody
(clone 18-20) - heavy chain (V-D-J Region)
(Mus musculus):
aagcctggag agacagtcaa gatctcctgc aaggcttctg ggtataccatt cacagtctat ggaatgaact gggtgaagca ggctccagga aaggatttaa agtggatggg ctggataaac acctacactg gagagccaac atatgctgat gacttcaagg gacggtttgc cttctctttg gaaacctctg ccagcactgc ctatttgcag atcaacaacc tcaaaaatga ggacatggct acatatttct gtgcaagaaa ggccttctat aggtacgacg ggggtatgga ctactgggt caaggaacct cagtcaccgt ctcctcag SEQ ID No. 9: anti-human CEACAM1 antibody
(clone 18-20) - light chain (V-J-Region)
(Mus musculus):
SSLSASLGGKVTITCKASQDINKFLAWYQHKPGKGPRLLIHYTSTLQPGI

PSRFSGSGSGRDYSFSISNLEPEDIATYYCLQYDNLYTFGGGTKLEIK

SEQ ID No. 10: anti-human CEACAM1 antibody
(clone 18-20) - light chain (V-J-Region)
(Mus musculus):
tcctcactgt ctgcatctct gggaggcaaa gtcaccatca cttgcaaggc aagccaagac attaacaagt ttttagcttg gtaccaacac aagcctggaa aagtcctag ctgctcata cattacacat ctacattaca gccaggcatc ccatcaaggt tcagtggaag tgggtctggg agagattatt ccttcagcat cagcaacctg gagcctgaag atattgcaac ttattattgt ctacaatatg ataatctgta cacgttcggt gggggaccaa agctggaaat aaaac SEQ ID No. 11: anti-human CEACAM1 antibody
(clone B3-17) - heavy chain (V-D-J-REGION)
(Mus musculus):
GPELVKPGTSVKMSCKASGYTFTTYVMHWVQQKPGQGLDWIGFFNPYN

DGTKYNEKFKGKATLTSDKSSSTAYMELSSLTSEDSAVYYCARWAYDGSY

AYWGQGTTLTVSS

SEQ ID No. 12: anti-human CEACAM1 antibody
(clone B3-17) - heavy chain (V-D-J-REGION)
(Mus Musculus):
ggacctgagc tggtaaagcc tgggacttca gtgaagatgt cctgcaaggc ttctggatac acattcacta cctatgttat gcactgggtg caacagaagc ctgggcaggg ccttgactgg attggatttt ttaatcctta caatgatggt actaagtaca atgagaagtt caaaggcaag gccacactga cttcagacaa atcctccagc acagcctaca tggaactcag cagcctgacc tctgaggact ctgcggtcta ttactgtgca agatgggcct acgatggtag ctacgcctac tggggccaag gcaccactct cacagtctcc tcag SEQ ID No. 13: anti-human CEACAM1 antibody
(clone B3-17) - light chain (V-J-REGION)
(Mus musculus):
SYLSVFLGGRVTITCKASDHINNWLAWYQQKPGNAPRLLISGATSLETGV

PSRFSGSGSGKDYTLSIISLQTEDVATYYCQQYWRTPFTFGSGTKLEIK

SEQ ID No. 14: anti-human CEACAM1 antibody
(clone B3-17) - light chain (V-J-REGION)
(Mus musculus):
tcctacttgt ctgtatttct aggaggcaga gtcaccatta cttgcaaggc aagtgaccac attaataatt ggttagcctg gtatcagcag aaaccaggaa atgctcctag gctcttaata tctggggcaa ccagtttgga aactggggtt ccttcaagat tcagtggcag tggatctgga aaggattaca ctctcagcat tatcagtctt cagactgaag atgttgctac ttattactgt caacagtatt ggagaactcc attcacgttc ggctcgggga caaagttgga aataaaac SEQ ID No. 15: soluble UspA 1 (Moraxella
catarhalis) GenBank: U61725.1:
MNKIYKVKKNAAGHLVACSEFAKGHTKKAVLGSLLIVGALGMATTASAQ

ATKGTGKHVVDNKDNKAKGDYSTASGGKDNEAKGNYSTVGGGDYNEAKGN

YSTVGGGSSNTAKGEKSTIGGGDTNDANGTYSTIGGGYYSRAIGDSSTIG

GGYYNQATGEKSTVAGGRNNQATGNNSTVAGGSYNQATGNNSTVAGGSHN

QATGEGSFAAGVENKANANNAVALGKNNTIDGDNSVAIGSNNTIDSGKQN

VFILGSSTNTTNAQSGSVLLGHNTAGKKATAVSSAKVNGLTLGNFAGASK

TGNGTVSVGSENNERQIVNVGAGNISADSTDAVNGSQLYALATAVKADAD

ENFKALTKTQNTLIEQGEAQDALIAQNQTDITANKTAIERNFNRTVVNGF

EIEKNKAGIAKNQADIQTLENNVGEELLNLSGRLLDQKADIDNNINNIYD

LAQQQDQHSSDIKTLKKNVEEGLLDLSGRLIDQKADLTKDIKTLENNVEE
GLLDLSGRLIDQKADIAKNQADIAQNQTDIQDLAAYNELQDQYAQKQTEA
IDALNKASSANTDRIATAELGIAENKKDAQIAKAQANENKDGIAKNQADI
QLHDKKITNLGILHSMVARAVGNNTQGVATNKADIAKNQADIANNIKNIY
ELAQQQDHSSDIKTLAKVSAANTDRIAKNKAEADASFETLTKNQNTLIE
QGEALVEQNKAINQELEGFAAHADVQDKQILQNQADITTNKAAIEQNINR
TVANGFEIEKNKAGIATNKQELILQNDRLNQINETNNRQDQKIDQLGYAL
KEQGQHFNNRISAVERQTAGGIANAIAIATLPSPSRAGEHHVLFGSGYHN
GQAAVSLGAAGLSDTGKSTYKIGLSWSDAGGLSGGVGGSYRWK

SEQ ID No. 16: soluble UspA1 (Moraxella
catarhalis) GenBank: U61725.1:
tgtgagcaaa tgactggcgt aaatgactga tgaatgtcta tttaatgaaa gatatcaata tataaaagtt gactatagcg atgcaataca gtaaaatttg ttacggctaa acataacgac ggtccaagat ggcggatatc gccatttacc aacctgataa tcagtttgat agccattagc gatggcatca agttgtgttg ttgtattgtc atataaacgg taaatttggt ttggtggatg ccccatctga tttaccgtcc cctaataag tgaggggggg ggagacccca gtcatttatt aggagactaa gatgaacaaa atttataaag tgaaaaaaaa tgccgcaggt cacttggtgg catgttctga atttgccaaa ggccatacca aaaaggcagt tttgggcagt ttattgattg ttggggcatt gggcatggca acgacggcgt ctgcacaagc aaccaaaggc acaggcaagc acgttgttga caataaggac aacaaagcca aaggcgatta ctctaccgcc agtggtggca aggacaacga agccaaaggc aattactcta ccgtcggtgg tggcgattat aacgaagcca aaggcaatta ctctaccgtc ggtggtggct ctagtaatac cgccaaaggc gagaaatcaa ccatcggtgg tggcgatact aacgacgcca acggcacata ctctaccatc ggtggtggct attatagccg agcctatagc gatagctcta ccatcggtgg tggttattat aaccaagcca caggcgagaa atcaacggtt gcaggggggca ggaataacca agccacaggc aacaactcaa cggttgcagg cggctcttat aaccaagcca caggcaacaa ctcaacggtt gcaggtggct ctcataacca agccacaggt gaaggttcat ttgcagcagg tgtagagaac aaagccaatg ccaacaacgc cgtcgctcta ggtaaaaata caccatcga tggcgataac tcagtagcca tcggctctaa taataccatt gacagtggca acaaaatgt ctttattctt ggctctagca caaacacaac aaatgcacaa gcggctccg tgctgctggg tcataatacc gctggcaaaa aagcaaccgc tgttagcagt gccaaagtga acggcttaac cctaggaaat tttgcaggtg catcaaaaac tggtaatggt actgtatctg tcggtagtga gaataatgag cgtcaaatcg tcaatgttgg tgcaggtaat atcagtgctg attcaacaga tgctgttaat ggctcacagc tatatgcttt ggccacagct gtcaaagccg atgccgatga aaactttaaa gcactcacca aaactcaaaa tactttgatt gagcaaggtg aagcacaaga cgcattaatc gctcaaaatc aaactgacat cactgccaat aaaactgcca ttgagcgaaa ttttaataga actgttgtca atgggtttga gattgagaaa aataaagctg gtattgctaa aaaccaagcg gatatccaaa cgcttgaaaa caatgtcgga gaagaactat aaatctaag cggtcgcctg cttgatcaaa aagcggatat tgataataac atcaacaata tctatgatct ggcacaacag caagatcagc atagctctga tatcaaaaca cttaaaaaaa atgtcgaaga aggtttgttg gatctaagtg gtcgcctcat tgatcaaaaa gcagatctta cgaaagacat caaaacactt gaaaacaatg tcgaagaagg tttgttggat ctaagcggtc gcctcattga tcaaaaagca gatattgcta aaaaccaagc tgacattgct caaaaccaaa cagacatcca agatctggcc gcttacaacg agctacaaga ccagtatgct caaaagcaaa ccgaagcgat tgacgctcta aataaagcaa gctctgccaa tactgatcgt attgctactg ctgaattggg tatcgctgag aacaaaaaag acgctcagat cgccaaagca caagccaatg aaaataaaga cggcattgct aaaaaccaag ctgatatcca gttgcacgat aaaaaaatca ccaatctagg tatccttcac agcatggttg caagagcggt aggaaataac acacaaggtg ttgctaccaa taaagctgac attgctaaaa accaagcaga tattgctaat aacatcaaaa atatctatga gctggcacaa cagcaagatc agcatagctc tgatatcaaa accttggcaa aagtaagtgc tgccaatact gatcgtattg ctaaaaacaa agctgaagct gatgcaagtt ttgaaacgct caccaaaaat caaaatactt tgattgagca aggtgaagca ttggttgagc aaaataaagc catcaatcaa gagcttgaag ggtttgcggc tcatgcagat gttcaagata agcaaatttt acaaaaccaa gctgatatca ctaccaataa ggccgctatt gaacaaaata tcaatagaac tgttgccaat gggtttgaga ttgagaaaaa taaagctggt attgctacca ataagcaaga gcttattctt caaaatgatc gattaaatca aattaatgag acaaataatc gtcaggatca gaagattgat caattaggtt atgcactaaa agagcagggt cagcatttta ataatcgtat tagtgctgtt gagcgtcaaa cagctggagg tattgcaaat gctatcgcaa ttgcaacttt accatcgccc agtagagcag gtgagcatca tgtcttattt

```
ggttcaggtt atcacaatgg tcaagctgcg gtatcattgg gtgcggctgg gttaagtgat acaggaaaat caacttataa gattggtcta agctggtcag atgcaggtgg attatctggt ggtgttggtg gcagttaccg ctggaaatag agcctaaatt taactgctgt atcaaaaaat atggtctgta taaacagacc atattttat ctaaaaactt atcttaactt ttatgaagca tcataagcca aagctgagta ataataagag atgttaaaat aagagatgtt aaaactgcta acaatcggc ttacgacgat aaaataaaat acctggaatg gacagcccca aaaccaatgc tgagatgata aaaatcgcct caaaaaaatg acgcatcata acgataaata aatccatatc aaatccaaaa tagccaattt gtaccatgct aaccatggct ttataggcag cgattcccgg catcatacaa atcaagctag gtacaatcaa ggctttaggc ggcaggccat gacgctgagc a
```

SEQ ID No. 17: soluble Opa (*Neisseria gonorrhoeae*) UniProtKB/Swiss-Prot: Q0PS02_NEIME:
YAAERITHDYPKATGANNTSTVSDYFRNIRAHSIHPRVSVGYDFGGWRIA
ADYASYRKWKESNSSTNAENRDSIQNYVKIETKHQGNGSFHAASSLGLSA
IYDFKLNDKFKPYIGARVAYGHVKHQVHSVESKNTIITSKPTGNTPAGGP
VPTGFVPKSAYHESHSISSL SEQ ID No. 18: Outer membrane protein P5 (*Haemophilus influenzae*) UniProtKB/Swiss-Prot: P43840.1:
MKKTAIALVVAGLAAASVAQAAPQENTFYAGVKAGQASFHDGLRALARE
YKVGYHRNSFTYGVFGGYQILNQNNLGLAVELGYDDFGRAKGREKGKTVV
KHTNHGTHLSLKGSYEVLEGLDVYGKAGVALVRSDYKLYNENSSTLKKLG
EHHRARASGLFAVGAEYAVLPELAVRLEYQWLTRVGKYRPQDKPNTALNY
NPWIGSINAGISYRFGQGAAPVVAAPEVVSKTFSLNSDVTFAFGKANLKP
QAQATLDSIYGEMSQVKSAKVAVAGYTDRIGSDAFNVKLSQERADSVANY
FVAKGVAADAISATGYGKANPVTGATCDQVKGRKALIACFAPDRRVEIAV
NGTK SEQ ID No. 19: soluble human recombinant CEACAM1 fusion protein (human CEACAM1(ENSG00000079385) with "IL-2 Secretory Leader" sequence and human IgG-Fc2 fusion protein):
PEITGEGGPPCTGCNSCLALHVLHLSRIRQLTTESMPFNVAEGKEVLLLV
HNLPQQLFGYSWYKGERVDGNRQIVGYAIGTQQATPGPANSGRETIYPNA
SLLIQNVTQNDTGFYTLQVIKSDLVNEEATGQFHVYPELPKPSISSNNSN
PVEDKDAVAFTCEPETQDTTYLWWINNQSLPVSPRLQLSNGNRTLTLLSV
TRNDTGPYECEIQNPVSANRSDPVTLNVTYGPDTPTISPSDTYYRPGANL
SLSCYAASNPPAQYSWLINGTFQQSTQELFIPNITVNNSGSYTCHANNSV
TGCNRTTVKTIIVTELSPVVAKPQIKASKTTVTGDKDSVNLTCSTNDTGI
SIRWFFKNQSLPSSERMKLSQGNTTLSINPVKREDAGTYWCEVFNPISKN
QSDPIMLNVECPPCPAPPVAGPSVFLFPPKPKDTLMISRTPEVTCVVVDV
SHEDPEVKFNWYVDGVEVHNAKTKPREEQYNSTYRVVSVLTVLHQDWLNG KEYKCKVSNKGLPSSIEKTISKAKGQPREPQVYTLPPSREEMTKNQVSLT
CLVKGFYPSDIAVEWESNGQPENNYKTTPPVLDSDGSFFLYSKLTVDKSR
WQQGNVFSCSVMHEALHNHYTQKSLSLSPGK SEQ ID No. 20: soluble human recombinant CEACAM1 fusion protein (human CEACAM1(ENSG00000079385) with "IL-2 Secretory Leader" sequence and human IgG-Fc2 fusion protein):
```
cctgagatca ccggcgaagg agggccacca tgtacaggat gcaactcctg tcttgcattg cactaagtct tgcacttgtc acgaattcgc agctgaccac cgagagcatg cccttcaacg tggccgaggg caaggaggtg ctgctgctgg tgcacaacct gccccagcag ctgttcggct acagctggta agggcgag agggtggacg gcaacaggca gatcgtgggc tacgccatcg gcacccagca ggccaccccc ggccccgcca acagcggcag ggagaccatc taccccaacg ccagcctgct gatccagaac gtgacccaga cgacaccgg cttctacacc ctgcaggtga tcaagagcga cctggtgaac gaggaggcca ccggccagtt ccacgtgtac cccgagctgc ccaagcccag catcagcagc aacaacagca ccccgtgga ggacaaggac gccgtggcct tcacctgcga gcccgagacc caggacacca cctacctgtg gtggatcaac aaccagagcc tgcccgtgag cccaggctg cagctgagca acggcaacag accctgacc ctgctgagcg tgaccaggaa cgacaccggc ccctacgagt gcgagatcca gaacccgtg agcgccaaca ggagcgaccc cgtgaccctg aacgtgacct acggccccga cacccccacc atcagcccca gcgacaccta caggcc ggcgccaacc tgagcctgag ctgctacgcc gccagcaacc ccccgccca gtacagctgg ctgatcaacg gcaccttcca gcagagcacc caggagctgt tcatccccaa catcaccgtg aacaacagcg gcagctacac ctgccacgcc aacaacagcg tgaccggctg caacaggacc accgtgaaga ccatcatcgt gaccgagctg agcccgtgg tggccaagcc ccagatcaag gccagcaaga ccaccgtgac cggcgacaag gacagcgtga acctgacctg cagcaccaac gacaccggca tcagcatcag gtggttcttc aagaaccaga gcctgcccag cagcgagagg atgaagctga gccagggcaa caccaccctg agcatcaacc ccgtgaagag ggaggacgcc ggcacctact ggtgcgaggt gttcaacccc atcagcaaga accagagcga cccatcatg ctgaacgtgg agtgccccc ttgcccagca ccacctgtgg caggaccttc agtcttcctc ttccccccaa aacccaagga caccctcatg atctcccgga cccctgaggt cacatgcgtg gtggtggacg tgagccacga agaccctgag gtcaagttca actggtacgt ggacggcgtg
```

```
                      -continued
gaggtgcata atgccaagac aaagccgcgg gaggagcagt acaacagcac gtaccgtgtg gtcagcgtcc tcaccgtcct gcaccaggac tggctgaatg gcaaggagta caagtgcaag gtctccaaca aaggcctccc atcctccatc gagaaaacca tctccaaagc caaagggcag ccccgagaac cacaggtgta caccctgccc ccatcccggg aggagatgac caagaaccag gtcagcctga cctgcctggt caaaggcttc tatcccagcg acatcgccgt ggagtgggag agcaatgggc agccggagaa caactacaag accacgcctc ccgtgctgga ctccgacggc tccttcttcc tctacagcaa gctcaccgtg gacaagagca ggtggcagca ggggaacgtc ttctcatgct ccgtgatgca tgaggctctg cacaaccact acacgcagaa gagcctctcc ctgtctccgg gtaaa
```

EXAMPLE SECTION 1.1.1 Description and Analysis of the Drawings

FIG. 1A shows representative continuous-flow cytometry histograms of profilerating B cells of wildtype (WT) or CEACAM1-/- mice (CEACAM1-Knockout mice), which were untreated (gray area), treated with anti-CEACAM1 antibody, LPS, or with recombinant mice-CD40 ligand in combination with mouse IL-4 (black line) for 48 hours. DAPI cells are shown (n=6).

FIG. 1B shows the absolute number of live cells B (DAPI-) at stated time points (n=3); sorted from the spleen, after treatment with or without recombinant mouse-CD40 ligand in combination with mouse IL-4 (n=3).

FIG. 1C shows representative histograms and statistical analysis of Annexin-V+ B cells: which were stimulated with recombinant mouse-CD40 ligand in combination with mouse IL-4 or left unstimulated, after 48 hours (DAPI- B cells are shown, n=6).

FIG. 1D shows the percentage of DAPI+ B cells from the spleen of WT and CEACAM1-/- mice after activation with recombinant mouse-CD40 ligand in combination with mouse IL-4 in the presence or absence of Btk inhibitor Ibrutinib cultured for 48 hours determined by FACS analysis (n=6). * $P<0.05$;  $P<0/01$; and * $P<0.001$ (Student t-test).

The results shown graphically in FIGS. 1A to 1D show that CEACAM1 promotes the survival of B cells in vitro.

Figure 2:
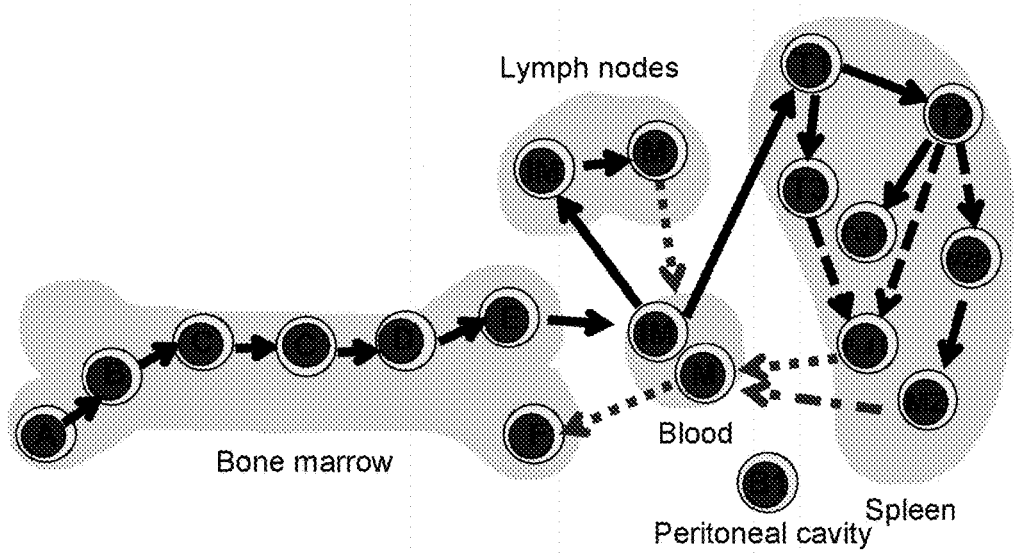
FIG. 2A shows a scheme of development, maturation and migration of B cells in bone marrow, blood, lymph nodes and spleen.
FIGS. 2B-E show the total number of B cell subpopulations of wildtype (WT) and CEACAM1−/− mice, measured by means of continuous-flow cytometry in bone marrow (b, n=6), in blood (c, n=4), lymph nodes (d, n=4) and in the spleen (e, n=10)
Figure 2:
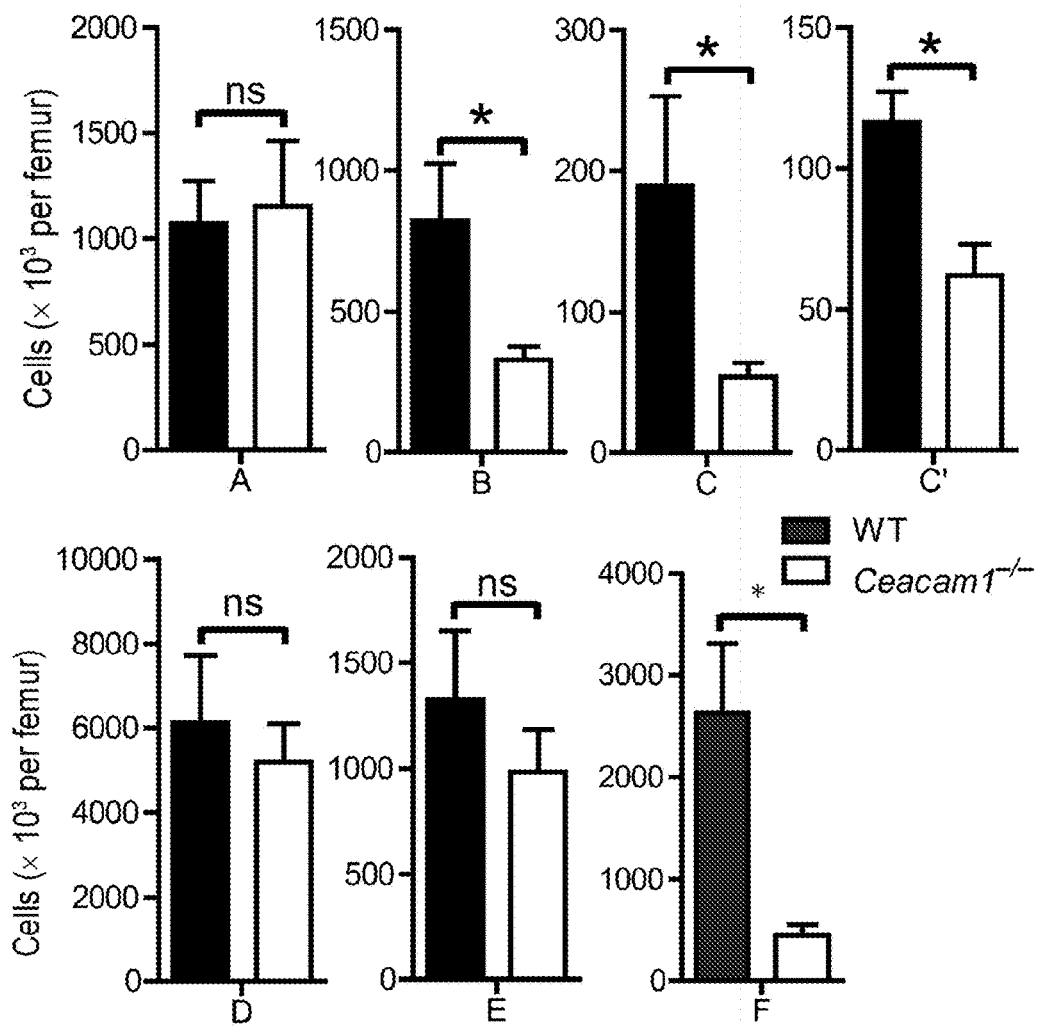
Figure 2:
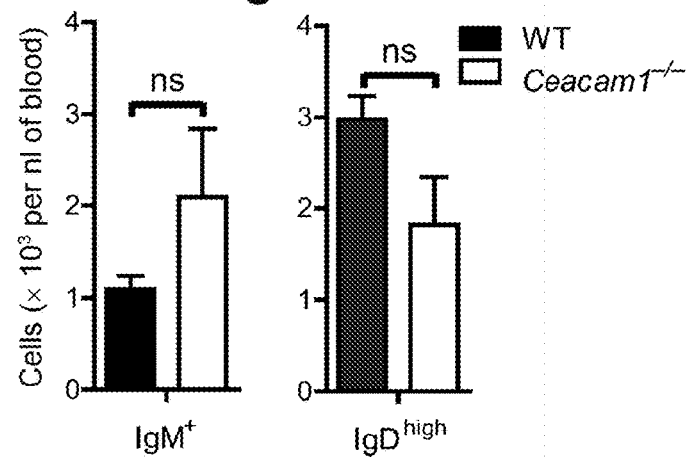
Figure 2:
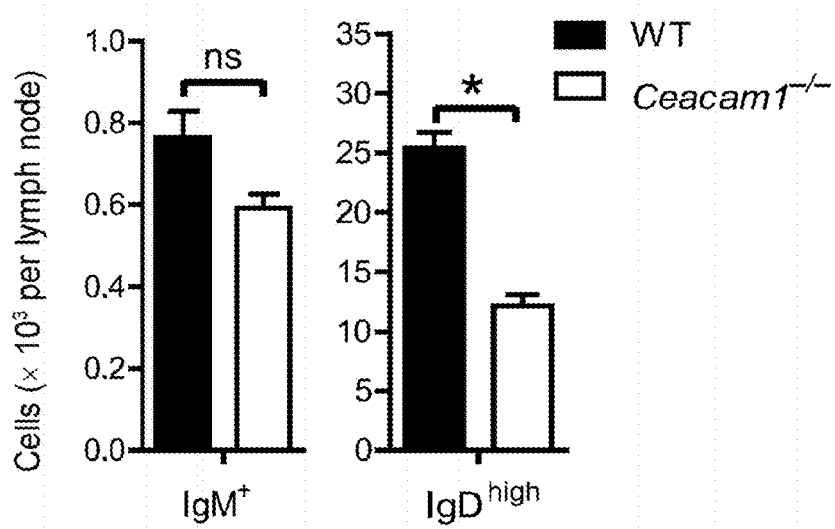
Figure 2:
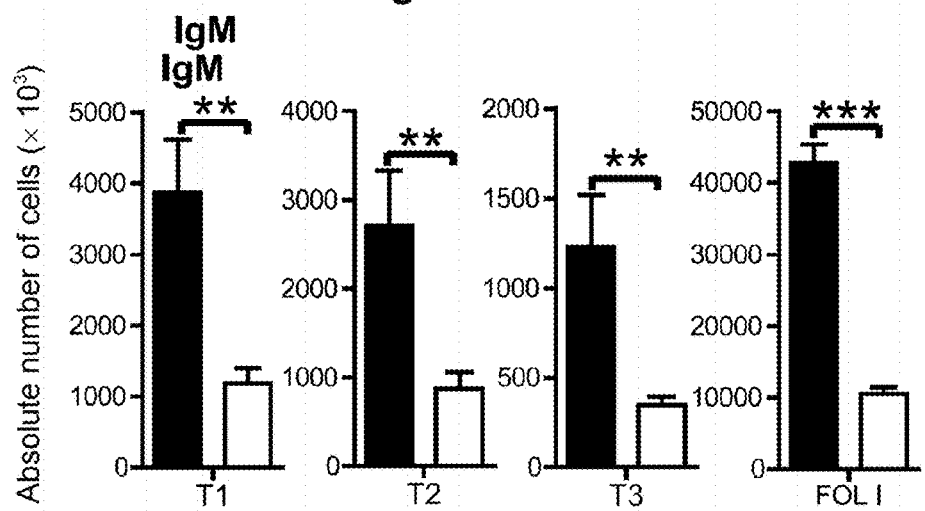
Figure 2:
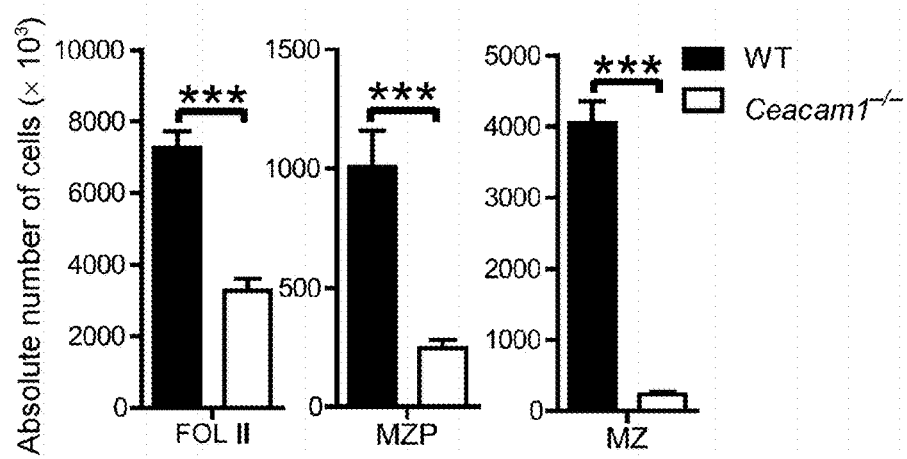

FIG. 2A shows a scheme of development, maturation and migration of B cells in bone marrow, blood, lymph nodes and spleen. The continuous arrows show the probable development pathway. The dashed arrows show a development pathway that is still under discussion. The dotted arrows show the differentiation after antigen stimulation. The "dash-dot arrow" shows assumed development pathways.

FIGS. 2B-E show the total number of B cell subpopulations of wildtype (WT) and CEACAM1-/- mice, measured by means of continuous-flow cytometry in bone marrow (b, n=6), in blood (c, n=4), lymph nodes (d, n=4) and in the spleen (e, n=10). For markers see Methods.

The results shown graphically in FIGS. 2A to 2D show that the expression of CEACAM1 promotes B cell differentiation and the survival of B cells in vivo.

Figure 3:
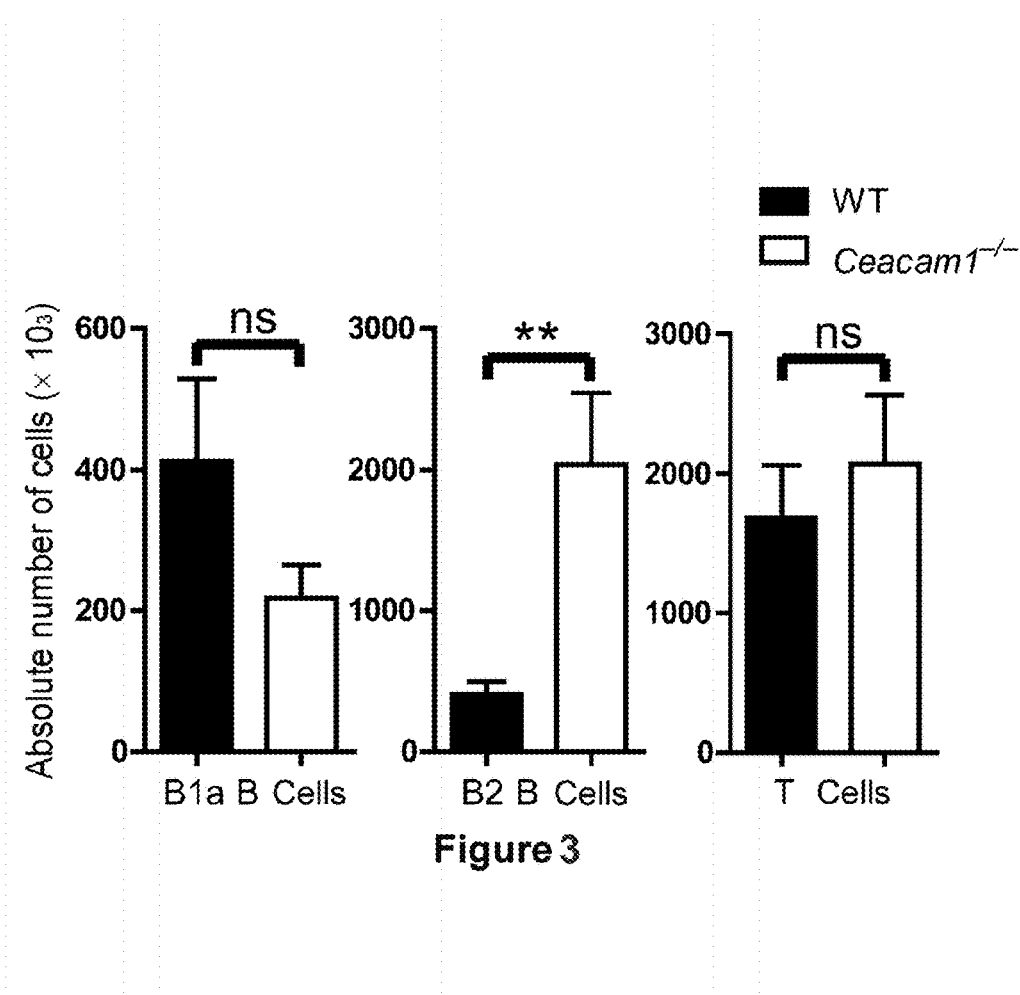
FIG. 3 shows the total number of B1a and B2 B cell subpopulations (B1a, CD19lowCD5int; B2, CD19highCD5neg) and T cells of wildtype (WT) and CEACAM1−/− mice, measured by means of continuous-flow cytometry in the abdominal cavity (n=6). * $P<0.05$ (Student t-test); ns=not significant.

FIG. 3 shows the total number of B1a and B2 B cell subpopulations (B1a, CD19lowCD5int; B2, CD19highCD5neg) and T cells of wildtype (WT) and CEACAM1-/- mice, measured by means of continuous-flow cytometry in the abdominal cavity (n=6). * $P<0.05$ (Student t-test); ns=not significant.

The results shown graphically in FIG. 3 show that the expression of CEACAM1 changes the B1 B cells.

Figure 4:
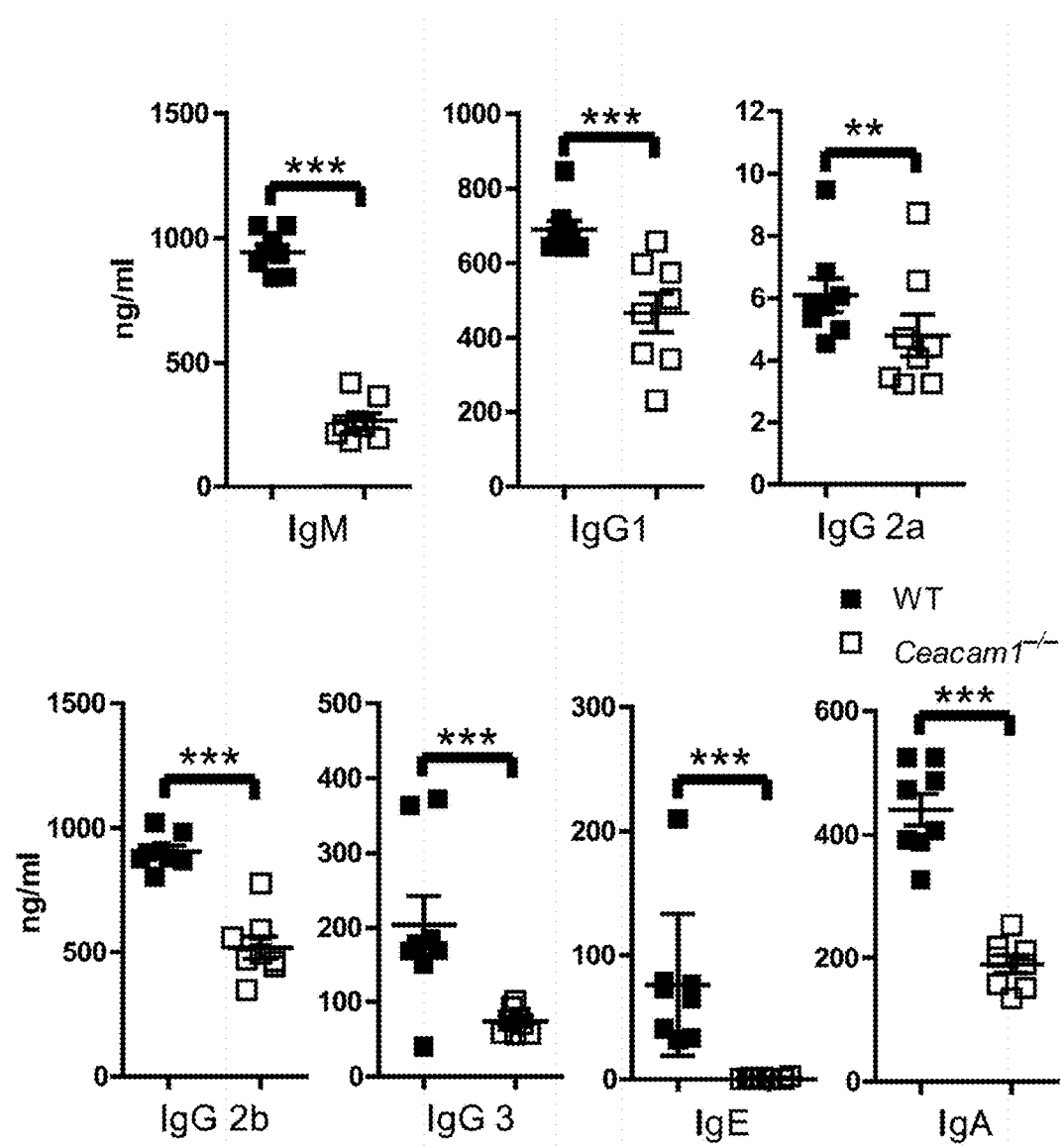
FIG. 4 shows the amount of serum immunoglobulins in naïve wildtype (WT) and CEACAM1−/− mice (n=8 per genotype).  $P<0.01$; and * $P<0.001$ (Student t-test)

FIG. 4 shows the amount of serum immunoglobulins in naïve wildtype (WT) and CEACAM1-/- mice (n=8 per genotype).  $P<0.01$; and * $P<0.001$ (Student t-test).

The results shown graphically in FIG. 4 show an advantageous influencing of the serum immunoglobulins by CEACAM1.

Figure 5:
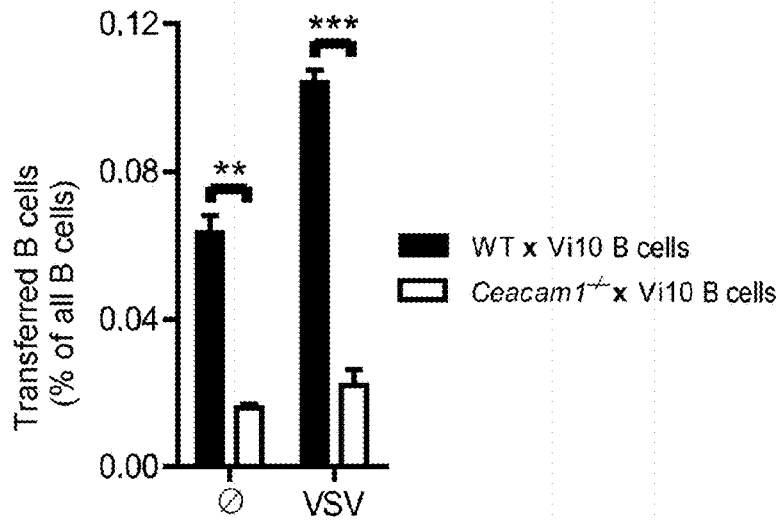
FIG. 5A shows the percentage of WT×Vi10 B cells and CEACAM1−/−×Vi10 B cells which were transferred adoptively to WT mice ($1\times10^7$ per mouse) on day −1 and which were infected with $2\times10^6$ PFU of vesicular stromatitis virus (VSV) on day 0. Analysis day 3 after infection (n=3)
FIGS. 5B-C show the total VSV neutralizing antibodies and neutralizing IgG antibodies in WT and CEACAM1−/− mice after intravenous infection with $2\times10^6$ PFU VSV (B, n=6-9 per group) and/or after the intravenous infection with $2\times10^8$ PFU of UV-inactivated VSV (C, n=8-9 per group)
FIG. 5D shows the VSV-neutralizing antibody response and neutralizing IgG antibodies in the sera of WT and CEACAM1−/− mice that had received $1\times10^7$ VSV-specific B cells (Vi10) on day −1 and were then infected with $2\times10^6$ PFU VSV on day 0 (n=7-9 per group)
FIG. 5E shows the VSV titer in various organs of WT and CEACAM1−/− mice after intravenous infection with $2\times10^6$ PFU VSV analyzed 8 days after infection (n=6 per group)
FIG. 5F shows the survival of WT and CEACAM1−/− mice after intravenous infection with $2\times10^6$ PFU VSV (n=9-12 per group)
FIG. 5G shows the survival of WT and CEACAM1−/− mice that were untreated or had been treated adoptively with $1\times10^7$ of VSV-specific B cells (Vi10) on day −1 and had been infected on day 0 with $2\times10^6$ PFU of VSV (n=4-9). * $P<0.05$;  $P<0.01$; and * $P<0.001$ (Student t-test)
Figure 5:
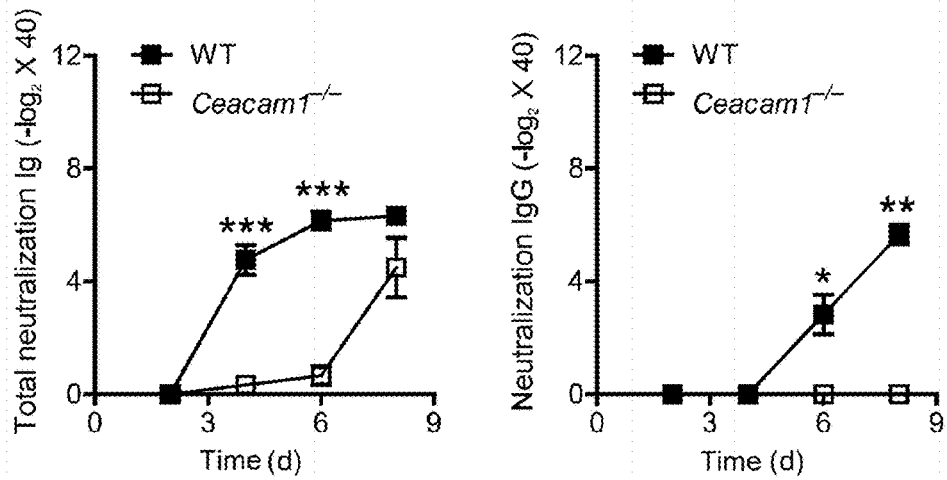
Figure 5:
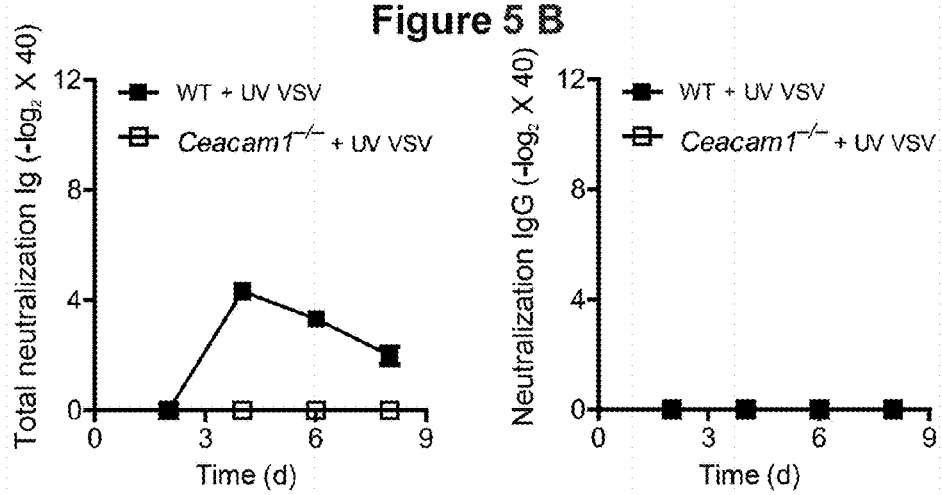
Figure 5:
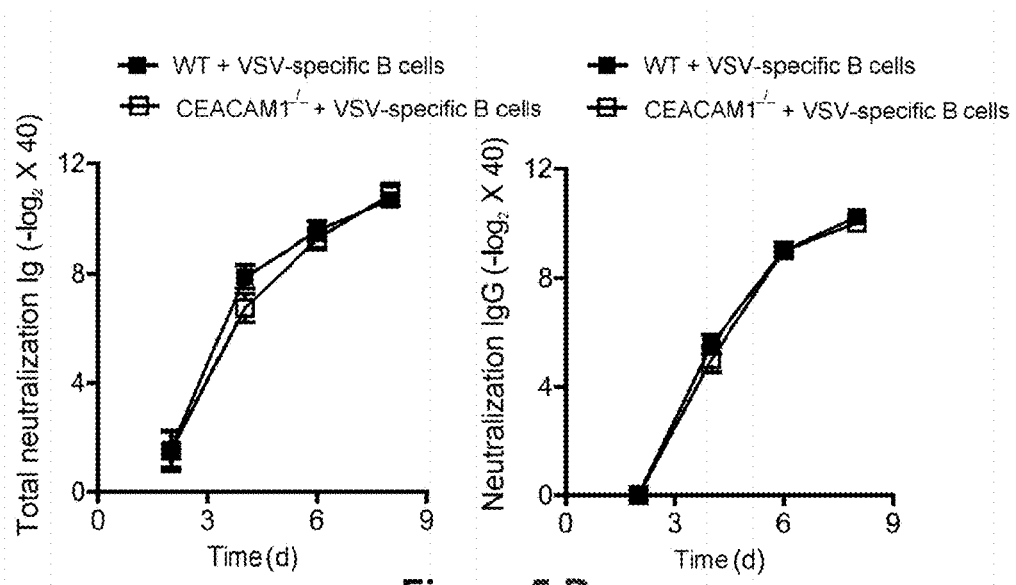
Figure 5:
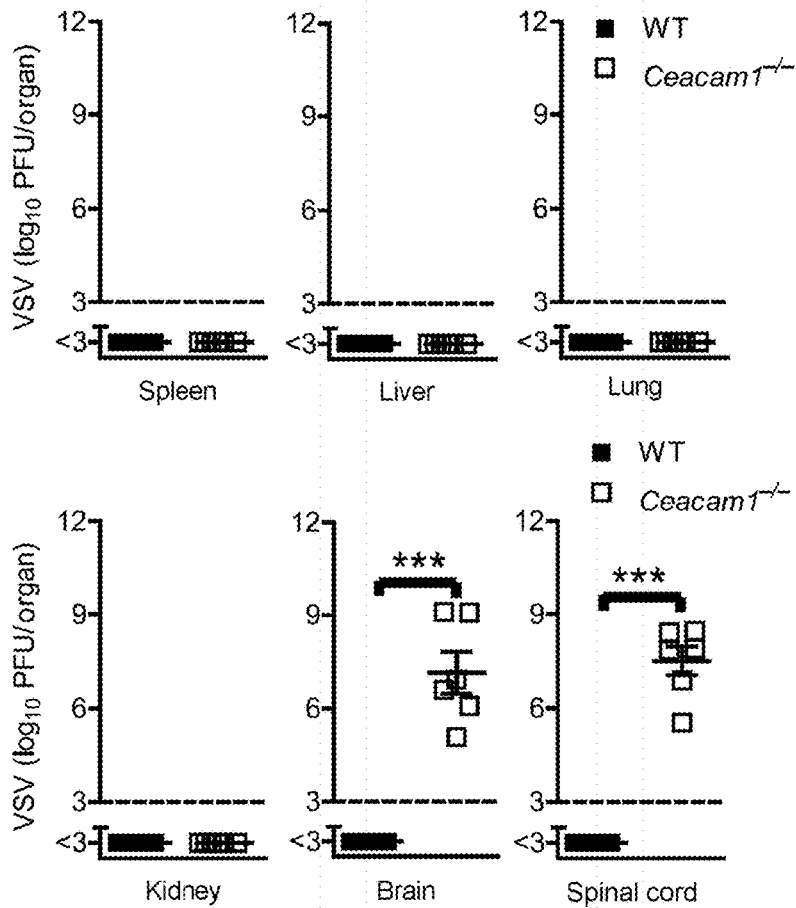
Figure 5:
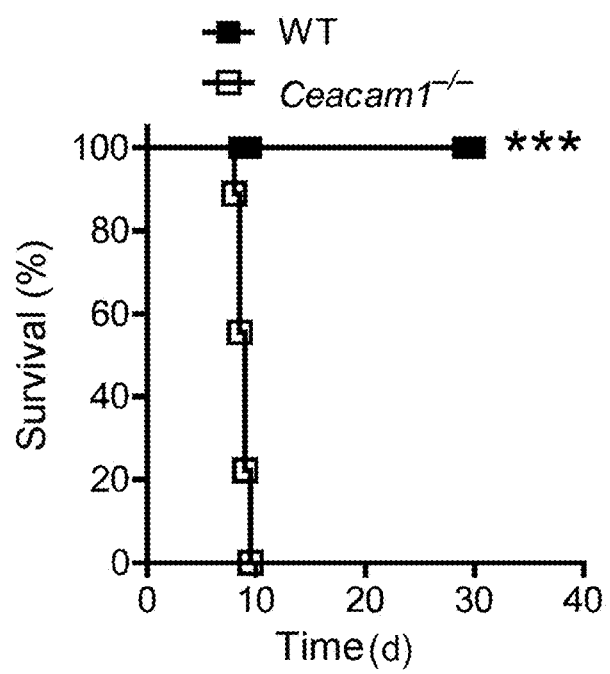
Figure 5:
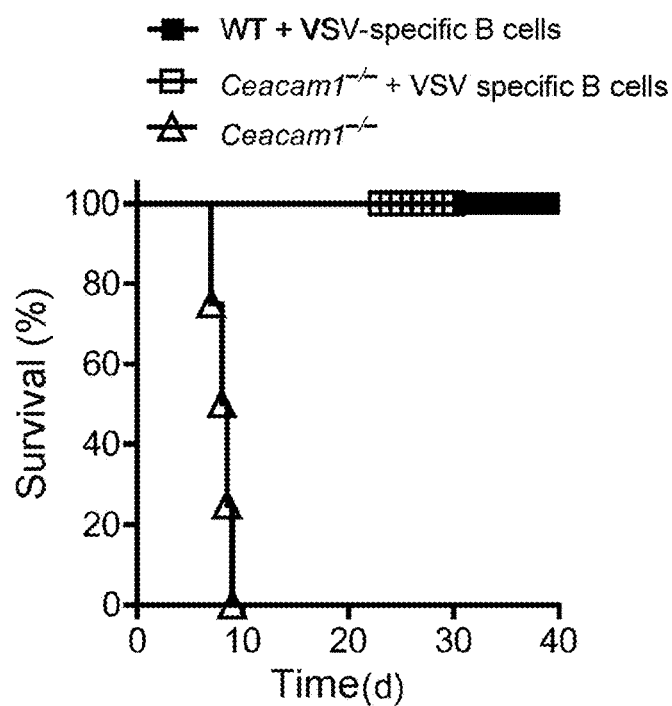

FIG. 5A shows the percentage of WT×Vi10 B cells and CEACAM1-/-×Vi10 B cells which were transferred adoptively to WT mice ($1\times10^7$ per mouse) on day -1 and which were infected with $2\times10^6$ PFU of vesicular stromatitis virus (VSV) on day 0. Analysis day 3 after infection (n=3).

FIGS. 5B and C show the total VSV neutralizing antibodies and neutralizing IgG antibodies in WT and CEACAM1-/- mice after intravenous infection with $2\times10^6$ PFU VSV (B, n=6-9 per group) and/or after the intravenous infection with $2\times10^8$ PFU of UV-inactivated VSV (C, n=8-9 per group).

FIG. 5D shows the VSV-neutralizing antibody response and neutralizing IgG antibodies in the sera of WT and CEACAM1-/- mice that had received $1\times10^7$ VSV-specific B cells (Vi10) on day -1 and were then infected with $2\times10^6$ PFU VSV on day 0 (n=7-9 per group).

FIG. 5E shows the VSV titer in various organs of WT and CEACAM1-/- mice after intravenous infection with $2\times10^6$ PFU VSV analyzed 8 days after infection (n=6 per group).

FIG. 5F shows the survival of WT and CEACAM1-/- mice after intravenous infection with $2\times10^6$ PFU VSV (n=9-12 per group).

FIG. 5G shows the survival of WT and CEACAM1-/- mice that were untreated or had been treated adoptively with $1\times10^7$ of VSV-specific B cells (Vi10) on day -1 and had been infected on day 0 with $2\times10^6$ PFU of VSV (n=4-9). * $P<0.05$;  $P<0.01$; and * $P<0.001$ (Student t-test).

The results shown graphically in FIGS. 5A to 5G show that activation of CEACAM1 is essential for an infection with VSV.

Figure 6:
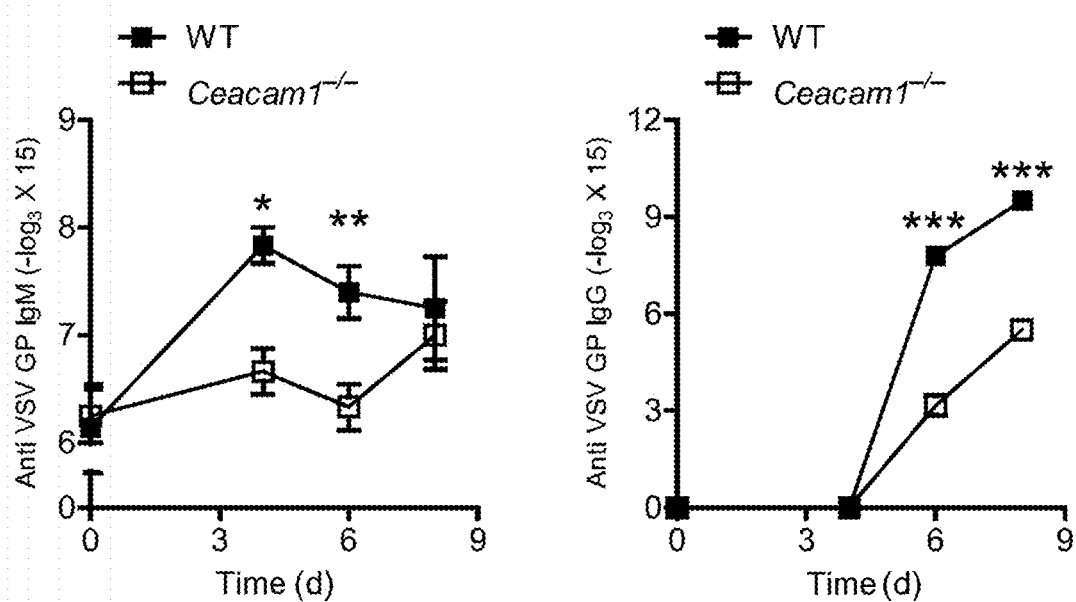
FIG. 6 shows anti-VSV-specific IgM and IgG antibodies in wildtype (WT) and CEACAM1−/− mice after intravenous infection with $2\times10^6$ PFU of VSV (n=4-7 per group). * $P<0.05$;  $P<0.01$; and * $P<0.001$ (Student t-test). Data that are for two experiments (mean±SEM)

FIG. 6 shows the anti-VS V-specific IgM and IgG antibodies in wildtype (WT) and CEACAM1-/- mice after intravenous infection with $2\times10^6$ PFU of VSV (n=4-7 per group). * $P<0.05$;  $P<0.01$; and * $P<0.001$ (Student t-test). Data that are for two experiments (mean±SEM).

The results shown graphically in FIG. 6 show that CEACAM1 is essential for anti-VSV-specific Ig production.

Figure 7:
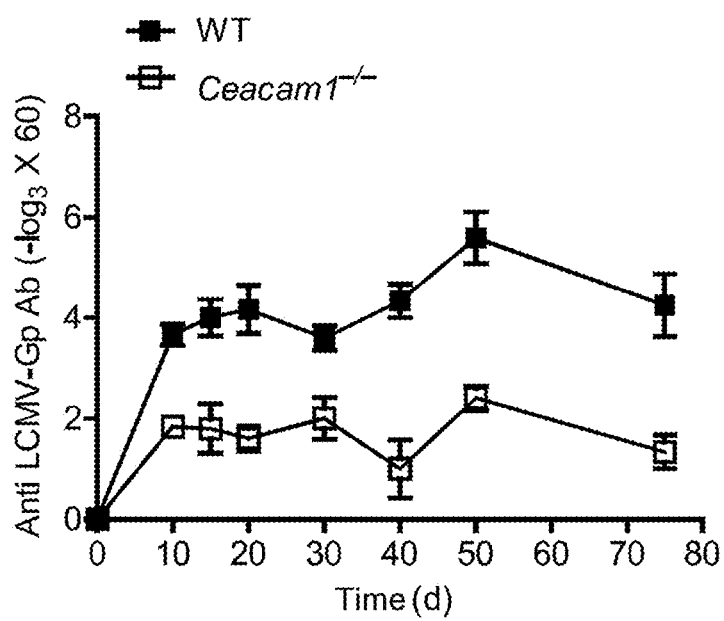
FIG. 7A shows the lymphoytic choriomeningitis virus (LCMV) glycoprotein-specific IgG antibody in the serum of wildtype (WT) and CEACAM1−/− mice after intravenous infection with 200 PFU of LCMV-WE (n=3-6 per group)
FIG. 7B shows the liver virus titer of WT and CEACAM1−/− mice 10 days after intravenous infection with $2\times10^6$ PFU of LCMV-WE (n=3 per group). *** $P<0.001$ (Student t-test)

FIG. 7A shows the lymphoytic choriomeningitis virus (LCMV) glycoprotein-specific IgG antibody in the serum of wildtype (WT) and CEACAM1-/- mice after intravenous infection with 200 PFU of LCMV-WE (n=3-6 per group).

FIG. 7B shows the liver virus titer of WT and CEACAM1-/- mice 10 days after intravenous infection with $2\times10^6$ PFU of LCMV-WE (n=3 per group). *** $P<0.001$ (Student t-test).

The results shown graphically in FIGS. 7A and 7B show that activation of CEACAM1 increases the LCMV-dependent B cell activation.

FIG. 8A shows the spleen VSV titer of WT or CEACAM1-/- mice 7 h after intravenous infection with $2\times10^6$ PFU of VSV (n=6 per genotype). ** $P<0.01$ (Student t-test).

FIG. 8B shows the interferon-alpha levels in the serum of WT or CEACAM1−/− mice 2 and 4 hours after intravenous infection with 2×10$^8$ PFU of VSV.

The results shown graphically in FIGS. 8A and 8B show deficit edge zones, replication and interferon induction in CEACAM1−/− mice.

Figure 9:
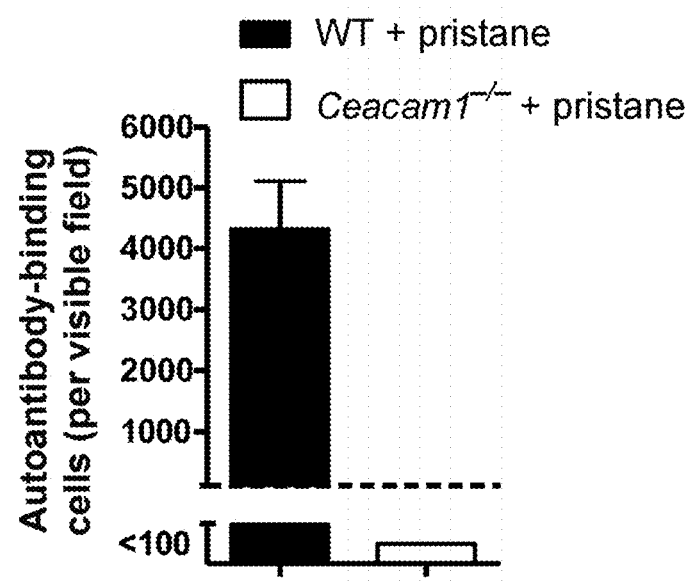
FIG. 9 shows the number of auto-antibody-binding cells on liver tissue slices that have been treated with serum of WT and CEACAM1−/− mice 100 days after intraperitoneal injection with 500 µL of pristane, and fluorescent anti-mouse IgG (n=3-5)

FIG. 9 shows the number of auto-antibody-binding cells on liver tissue slices that have been treated with serum of WT and CEACAM1−/− mice 100 days after intraperitoneal injection with 500 μL of pristane, and fluorescent anti-mouse IgG (n=3-5).

Figure 10:
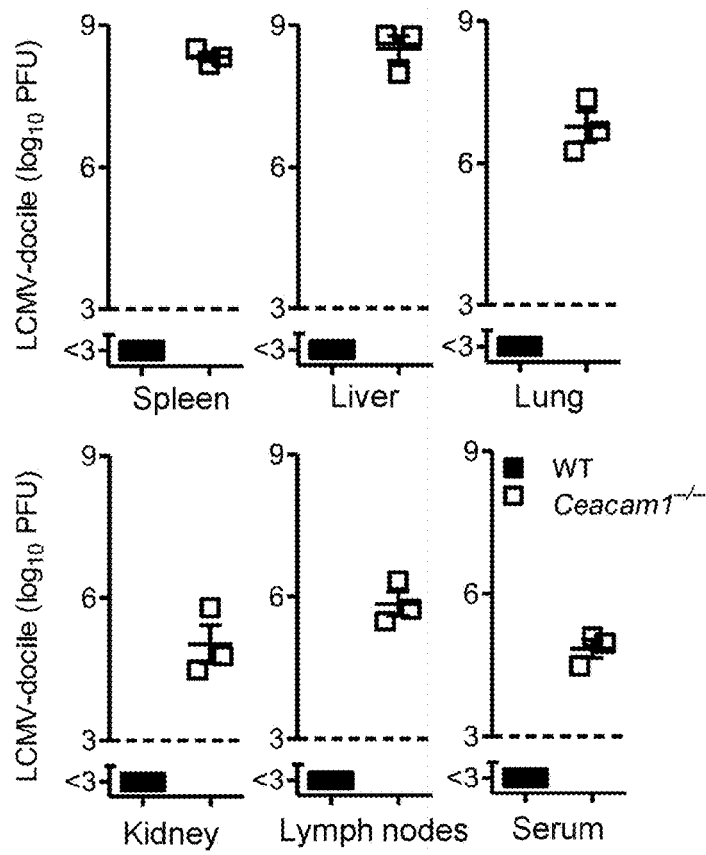
FIG. 10 shows the amount of virus in different organs of wildtype (WT) or CEACAM1−/− mice after infection with 200 PFU of the chronic lymphocytary choriomeningitis virus strain (LCMV docile), measured 10 days after infection (n=3)

FIG. 10 shows the amount of virus in different organs of wildtype (WT) or CEACAM1−/− mice after infection with 200 PFU of the chronic lymphocytary choriomeningitis virus strain (LCMV docile), measured 10 days after infection (n=3).

Figure 11:
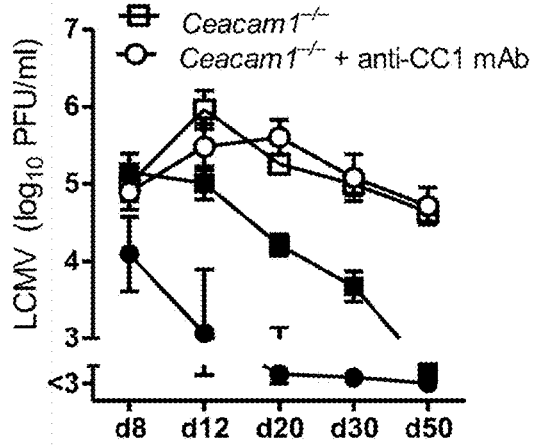
FIG. 11A shows the amount of virus in blood of wildtype (WT) or CEACAM1−/− mice which had been treated with control antibodies or anti-CEACAM1 antibodies (200 µg day −1) and had additionally been infected on day 0 with $2\times10^4$ PFU of the chronic lymphocytary choriomeningitis virus strain (LCMV docile) (n=6)
FIG. 11B shows alanine-aminotransferase (biomarker for liver damage) in the serum of wildtype (WT) or CEACAM1−/− mice which had been treated with control antibodies or anti-CEACAM1 antibodies (200 mg day −1) and had additionally been infected on day 0 with $2\times10^4$ PFU of the chronic lymphocytary choriomeningitis virus strain (LCMV docile) (n=6)
Figure 11:
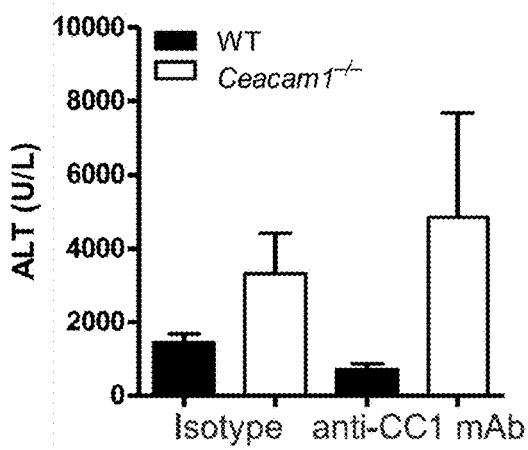

FIG. 11A shows the amount of virus in blood of wildtype (WT) or CEACAM1−/− mice which had been treated with control antibodies or anti-CEACAM1 antibodies (200 μg day −1) and had additionally been infected on day 0 with 2×10$^4$ PFU of the chronic lymphocytary choriomeningitis virus strain (LCMV docile) (n=6).

FIG. 11B shows the alanine-aminotransferase (biomarker for liver damage) in the serum of wildtype (WT) or CEACAM1−/− mice which had been treated with control antibodies or anti-CEACAM1 antibodies (200 μg day −1) and had additionally been infected on day 0 with 2×10$^4$ PFU of the chronic lymphocytary choriomeningitis virus strain (LCMV docile) (n=6).

Figure 12:
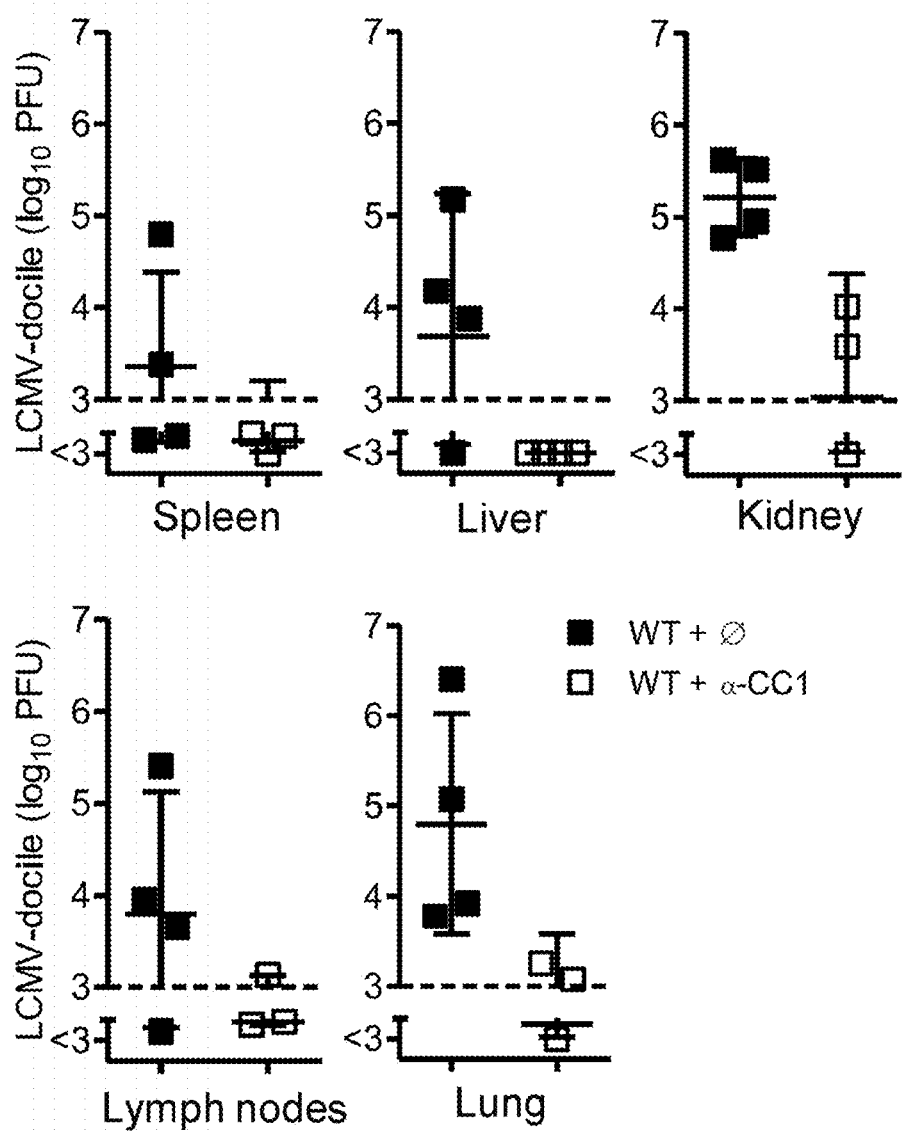
FIG. 12 shows the amount of virus in different organs of wildtype (WT) mice (measured day 60) that had been infected on day 0 with 2×10⁶ PFU of the chronic lymphocytary choriomeningitis virus strain (LCMV docile) and additionally on day 16 were left untreated or treated with anti-CEACAM1 antibodies (200 µg) (n=3-4).

FIG. 12 shows the amount of virus in different organs of wildtype (WT) mice (measured day 60) that had been infected on day 0 with 2×10$^6$ PFU of the chronic lymphocytary choriomeningitis virus strain (LCMV docile) and additionally on day 16 were left untreated or treated with anti-CEACAM1 antibodies (200 μg) (n=3-4).

1.1.2 Methods and Materials:
1.2.1 Mice:

Ceacam1$^{−/−}$ mice were reared on the generic background of C57BL/6 (back-crossed at least 8 times and up to 16 times) and were raised homozygotically. Vi10/CD45.1 mice that express a VSV-specific B cell receptor as transgene were used for cell transfer studies, and mice that express the CD45.1 transgene were used for reconstitution of bone marrow. In all studies, 6- to 8-week-old mice of the same sex were used. All animals were held in ventilated individual cages. In the survival experiments, the health state of the mice was checked twice per day. The animal experiments were carried out with approval by the state agency for nature, environment and consumer protection of Nordrhein Westfalen (Recklinghausen, Germany) and in accordance with the German animal protection law or in accordance with the institute guidelines of the Ontario Cancer Institute of the University Health Network and of McGill University, USA. Animals that displayed serious symptoms of illness or paralysis or suffered considerable weight loss during a VSV infection were taken out of the experiment and counted as deaths for the statistical analysis.

1.2.2 Virus Assays and Plaque Assays:

Vesicular stomatitis virus (VSV), strain Indiana (VSV-IND, Mudd-Summers isolate) was originally obtained by Prof. D. Kolakofsky (University of Geneva, Switzerland). The virus was multiplied on BHK-21 cells having a multiplicity of infection (MOI) of 0.01. The VSV concentration was determined as described and was then plated out in the plaque technique onto Vero cells (Fink, K. et al. "Early type I interferon-mediated signals on B cells specifically enhance antiviral humoral responses." European Journal of Immunology (2006), 36, 2094-2105.). Mice were infected intravenously with VSV in the doses stated. Virus titers were measured using a plaque assay. For this assay, organs were comminuted in Dulbecco's Modified Eagle Medium (DMEM), that contains 2% of fetal calf serum (FCS), made 1:3 over 12 stages and plated out on Vero cells. After 2-hours incubation at 37° C., a coating medium (overlay) was added and the virus preparation was again incubated at 37° C. The plaques were counted 24 h later by means of staining using crystal violet.

The strain of the lymphocytary choriomeningitis virus LCMV-WE was originally obtained by F. Lehmann-Grube (Heinrich Pette Institute, Hamburg, Germany) and multiplied in L929 cells, MC57 cells or both. Mice were infected intravenously in the dose stated. LCMV virus titer was ascertained by a plaque assay on MC57 fibroblasts as described previously (Battegay, M. et al. "Quantification of lymphocytic choriomeningitis virus with an immunological focus assay in 24- or 96-well plates." J Virol Methods (1991), 33, 191-198.). In brief, comminuted organs were plated out with MC57 cells as described above and incubated at 37° C.

The strain of the lymphocytary choriomeningitis virus LCMV docile was originally obtained by F. Lehmann-Grube (Heinrich Pette Institute, Hamburg, Germany) and multiplied in L929 cells, MC57 cells, or both.

The influenza A virus was obtained by the Westendorf Working Group, University of Duisburg-Essen.

After incubation for 3 hours at 37° C., a coating medium was added and the virus preparation was again incubated at 37° C. The plaques were enumerated 72 h later by means of staining using LCMV-NP (nucleoprotein of LCMV). The cells were fixed (using 4% formaldehyde solution), permeabilized (using 1% Triton-X solution), blocked (using 10% FCS in phosphate-buffered saline PBS) and stained using anti-LCMV-NP antibodies (produced inhouse). As a secondary antibody, a conjugated anti-rabbit-IgG antibody with enhanced chemoluminescence (ECL) was used. Plaques were detected by a staining reaction (0.2 M $Na_2HPO_4$+0.1 M citric acid+30% $H_2O_2$+o-phenylenediamine dihydrochloride), wherein all chemicals were obtained from Sigma-Aldrich.

1.2.3 Test for Neutralizing Antibodies:

Serum was prediluted (1:40). The complement system was inactivated at 56° C. for 30 min. In order to record IgG kinetics, diluted samples were treated with 2-mercaptoethanol (0.1 M) in order to remove IgM. Serum was adjusted 1:2 over 12 stages and was incubated with 1×10$^3$ plaque-forming units (PFU) of the VSV. After 90 minutes of incubation at 37° C., the virus-serum mixture was plated out on Vero cells. After one hour, a coating medium was added and the mixture was again incubated for 24 h at 37° C. The plaques were enumerated by staining with crystal violet. Antibody titers are shown as 2- or 3-fold dilution stages (−$\log_2$ and −$\log_3$)-fold predilution (i.e. ×40).

1.2.4 Culture of B Cells:

Spleen preparations of mice of the wildtype (WT) and Ceacam1$^{−/−}$ mice were homogenized in MACS buffer (1% FCS and 0.8% 0.5 M EDTA) for magnet-activated cell sorting. B220$^+$ B cells were isolated by positive selection with CD45R-conjugated magnetic particles (MACS Miltenyi Biotech). By means of continuous-flow cytometry, it was verified that the purity of the B220$^+$ cells was greater than 95%. For proliferation studies, the cells were labeled with 5 μM carboxyfluorescein succinimidyl ester (CFSE) and 2×10$^5$ cells per well were cultured in 96-well plates in cell culture medium RMPI 1640 with addition of 10% LPS-free FCS (without lipopolysaccharide), 1% antibiotics and 0.1% 50 mM 2-mercaptoethanol. Thereafter, they were treated with anti-CEACAM1 antibody (20 μg/ml, clone CC1; donated by Dr. Kathryn V. Holmes, University of Colorado, Denver, USA) or recombinant mouse-CD40 ligands (1 μg/ml) in combination with mice-IL4 (10 ng/ml; R&D Systems) or LPS (10 ng/ml; Sigma Aldrich) for 48 h. Likewise, B cells (as described above) purified for inhibition experiments were cultured in the above-described medium with recombinant mouse-CD40 ligands (1 μg/ml) in combination with mouse-IL4 (10 ng/ml; R&D Systems) and treated with 10 μM Ibrutinib (Selleck). As a control, the same amounts of DMSO (dimethyl sulfoxide) that is used for dissolving Ibrutinib were added to wells. The cell death was measured by staining with 4',6-diamidine-2-phenylindole (DAPI; Life Technologies). For survival experiments, B cells were cultured as stated hereinbefore and the cells with Annexin-V (BD Biosciences) were thereafter stained using DAPI. At the stated time points, the proliferation and survival were determined by fluorescence-activated cell sorting (FACS). For cell signal experiments, splenocytes were dissociated in very low endotoxic-DMEM (VLE-DMEM) with addition of 10% LPS-free FCS and 1% antibiotic and treated with anti-CEACAM1 antibody (clone CC1, 20 μg/ml; K. Holmes) and anti-IgM antibody (10 μg/ml) (Jackson ImmunoResearch Laboratories, Inc.) for differing times at 37° C.

1.2.5 Continuous-flow Cytometry:

Peripheral blood cells were stained with antibodies anti-Ly6G (RB6-8C5), anti-CD115 (AFS98), anti-CD45R (B220; RA3-6B2), anti-CD90.2 (30-H12), anti-CEACAM1 (CC1; with corresponding isotype control anti-IgG1 [M1-14D12]), anti-IgD (11-26c), anti-CD93 (AA4.1), anti-CD19 (1D3) (all from eBioscience) and anti-IgM (II/41; BD Biosciences). Isolated bone marrow cells were suspended in FACS buffer (0.5 M EDTA, 0.1% sodium azide, 1% FCS in PBS) and incubated with antibodies anti-CD45R (B220; RA3-6B2), anti-IgD (11-26c), anti-IgM (II-41), anti-CEACAM1 (CC1), anti-CD24 (M1/69) (all from eBioscience), anti-CD43 (1B-11) and anti-BP1 (6C3) (from BioLegend). Inguinal lymph nodes were disaggregated in FACS buffer and the cells were stained for antibodies anti-CD45R (B220; RA3-6B2), anti-CD19 (1D3), anti-IgD (11-26c) (all from eBioscience) and anti-IgM (II/41) (BD Biosciences). Spleens were dissociated in FACS buffer and splenocytes were incubated with antibodies anti-CD45R (B220; RA3-6B2), anti-CD19 (1D3), anti-CD93 (AA4.1), anti-CD21/35 (8D9), anti-CD23 (B3B4), anti-IgD (11-26c), anti-CEACAM1 (CC1), anti-CD45.1 (A20), anti-CD45.2 (104) (all from eBioscience) and anti-IgM (II/41) (BD). Human peripheral blood samples were stained with antibodies anti-IgD (IA6-2) and anti-CD27 (M-T271) (both from BD Biosciences) and antibody anti-CEACAM1 (mAB, B3-17) (from Dr. Singer, Essen). Peritoneal B cells were stained for antibodies anti-CD19 (1D3), anti-CD45R (B220; RA3-6B2), anti-IgM (II/41) (all from eBioscience) and anti-CD5 (53-7.3) (BD Biosciences) and anti-CD43 (1B-11) (from BioLegend). Dead cells were discriminated by staining with propidium iodide (PI, eBioscience) and/or DAPI and were excluded from all analyses apart from blood analyses. For cell signal experiments, cells were fixed and permeabilized (BD Phosflow, BD Biosciences) as per the manufacturer's instructions. The cells were stained with antibody anti-Btk (pY223)/Itk (pY180) (BD Phosflow). All antibodies were diluted 1:100 to their starting concentration in FACS buffer. For quantitative determination of the total cell counts, FACS particles were used (BD Biosciences). All stained cells were analyzed in a continuous-flow cytometer of the LSRII type or FACSFortessa (BD Biosciences) type, and the data were analyzed using Flowjo software.

1.2.6 Gating Strategy for Identifying Subgroups of B Cells

TABLE 1

Gating Strategy for Identifying Subgroups of B Cells

| Origin | B cell subgroup | Marker |
| --- | --- | --- |
| Bone marrow | immature, newly formed | B220$^+$ CD43$^-$ IgD$^{-/low}$ IgM$^+$ |
|  | mature recirculating, follicular (FO) | B220$^+$ CD43$^-$ IgD$^{high}$ IgM$^-$ |
| Blood | immature, newly formed | B220$^+$ IgD$^{-/low}$ IgM$^+$ |
|  | mature recirculating, follicular (FO) | B220$^+$ IgD$^{high}$ IgM$^-$ |
|  | native-like | B220$^+$ CD93$^{high}$ IgD$^-$ IgM$^-$ |
| Lymph nodes | immature, newly formed | B220$^+$ CD19$^+$ IgD$^{-/low}$ IgM$^+$ |
|  | mature recirculating, follicular (FO) | B220$^+$ CD19$^+$ IgD$^{high}$ IgM$^-$ |
| Spleen | Marginal zone (MZ) | B220$^+$ CD19$^+$ CD93$^{-/low}$ CD21/35$^{high}$ CD23$^-$ |
|  | follicular (FO) | B220$^+$ CD19$^+$ CD93$^{-/low}$ CD21/35$^{int}$ CD23$^+$ |
|  | transitional T1 | B220$^-$ CD19$^-$ CD93$^+$ CD23$^-$ IgM$^{high}$ |
|  | transitional T2 | B220$^-$ CD19$^-$ CD93$^+$ CD23$^+$ IgM$^{high}$ |
|  | transitional T3 | B220$^-$ CD19$^-$ CD93$^+$ CD23$^+$ IgM$^{low}$ |

1.2.7 LCMV Glycoprotein GP1-specific IgG Measurements:

The detection of LCMV glycoprotein GP1-specific IgG by ELISA (Enzyme Linked Immunosorbent Assay) has already been described (Recher, M. et al. "Deliberate removal of T cell help improves virus-neutralizing antibody production." Nature immunology (2004), 5, 934-942.). In brief, flat-bottomed 96-well plates Nunc Immuno Plates (Thermo Scientific) were coated with anti-human IgG (Jackson ImmunoResearch Laboratories, Inc) ENREF 60 in coating buffer (0.1 M Na$_2$CO$_3$+0.1 M NaHCO$_3$; pH 9.6) overnight at 4° C. On the next day, the plates were washed with a wash buffer (PBS with 0.05% Tween20) and a blocking of unspecific binding was performed for 2 hours with 2% FCS in PBS. The plates were incubated for 3 hours at room temperature with LCMV Gp-Fc supernatant (produced inhouse). The plates were washed and established with prediluted (1:20) serum over 12 recesses with dilutions of 1:3 in sequential recesses. After an incubation of 90 minutes, the plates were incubated with horseradish peroxidase (HRP)-conjugated anti-mouse-IgG antibodies (Sigma). After one hour of incubation, the plates were developed as described hereinafter.

1.2.8 ELISA Measurements:

For detection of VSV-specific anti-IgG- and anti-IgM antibodies, flat-bottomed 96-well plates Nunc Immuno Plates (Thermo Scientific) were coated with baculovirus VSV-GP (Lang, K. S. et al. "MyD88 protects from lethal encephalitis during infection with vesicular stomatitis virus." European journal of immunology (2007), 37, 2434-2440.) in coating buffer 0.1 M NaCO$_3$ (0.1 M Na$_2$CO$_3$+0.1 M NaHCO$_3$; pH 9.6) overnight at 4° C. On the next day, the plates were washed with a wash buffer (PBS with 0.05% Tween20) and a blocking of unspecific binding with 2% FCS in PBS was performed for 1 to 2 hours. The plates were washed once and established with prediluted (1:15) serum over 12 recesses with dilutions of 1:3 in sequential recesses. The plates were incubated at room temperature for 2 h. The plates were washed with wash buffer and incubated with HRP-conjugated anti-mouse-IgG-antibody (Sigma) or anti-mouse-IgM-antibody (Sigma) for 30 to 60 min. The plates were washed and incubated in the dark with 1×TMB substrate solution (eBioscience), after which 10% $H_2SO_4$ solution was added in order to interrupt the staining reaction. The optical density was measured at 450 nm (FLUOstar Omega, BMG LABTECH). Various immunoglobulin isotypes and subtypes were measured in naïve serum of WT mice and Ceacam1$^{-/-}$ mice, as has been described (Recher, M. et al. "B cell-intrinsic deficiency of the Wiskott-Aldrich syndrome protein (WASp) causes severe abnormalities of the peripheral B cell compartment in mice." Blood (2012), 119, 2819-2828.).

1.2.9 Formation of Mouse-anti-human-CEACAM1-antibody:

Female mice from 8 to 10 weeks in age were immunized in three stages with human CEACAM1-Fc (50 µg/90 µl in PBS) mixed with Gerbu adjuvants MM (60 µl) (ideally on day 0, day 14 and day 21; intraperitoneally (i.p.) the first immunization, subcutaneously (s.c.) the second and third immunization). The amount of the first immunization was twice the amount of all subsequent immunizations. One week after the third immunization, blood was withdrawn from the mice for obtaining serum. In order to test whether the titer was sufficient, an ELISA or a continuous-flow cytometric analysis was carried out. The titer of day 0 to day 21 had generally increased 100 to 1000 fold. Mice having a sufficient titer were boosted with 25 µg of human CEACAM1-Fc dissolved in sterile PBS without adjuvant i.v. and i.p., four days before the mice were killed and the splenocytes (spleen cells) were obtained.

The mice were killed by cervical fracture and the spleen was removed under aseptic conditions. The spleen was squashed through a 70 µm nylon cell sieve. Splenocytes were transferred into a 50 ml Falcon tube and washed three times with DMEM medium that did not contain any additives (e.g. FCS). In parallel, the fusion partner cell line (the mice myeloma cell line NS1/0) was likewise washed in DMEM. Thereafter, the splenocytes and myeloma cells were mixed in a ratio of 5:1 and centrifuged for 5 min at 2000 rpm. Then, the supernatant was removed and the cell pellet was used for the fusion. For this purpose, 1 ml of PEG was slowly added to the cell pellet and mixed carefully within 1 min. Thereafter, PEG was diluted very slowly with warm DMEM according to the following protocol: 1 min=1 ml, 1 min=1 ml, 1 min=1 ml, 1 min=1.5 ml, 1 min=1.5 ml, 1 min=2.5 ml, 1 min=2.5 ml, 1 min=5 ml, 1 min=5 ml, 1 min=5 ml, 1 min=5 ml, 1 min=5 ml, 1 min=5 ml.

Then, the fused cells were centrifuged (10 min at 800 rpm) and the supernatant was carefully removed. Then, the cell pellet was resuspended (8 ml of HAT medium per $10^7$ NS/1/0 cells) and the cells were plated out in flat-bottomed 96-hole cell culture plates for HAT selection. The medium was removed every third day. After 10 to 14 days, when cell clones were visible, and the medium became yellow due to the pH shift, supernatants were tested for secreted anti-human-CEACAM1 antibody by means of continuous-flow cytometry and ELISA. Positive cell clones were subcloned (=monoclonal), further tested and used for a mAb production.

Subsequently, mAbs were freed from the cell culture supernatant (for example 500 ml) via protein G-sepharose columns (column chromatography), eluted by pH shift with the use of 0.1 M glycine buffer (pH 2.5) and dialyzed against sterile PBS. Sterile-filtered mAb solution was used in order to determine the Ig concentration by measuring the $OD_{280\,nm}$ and the concentration was calculated using the formula $OD_{280\,nm}/1.36$=x mg/ml.

1.2.10 Statistical Analysis:

Data were expressed in figures as means±S.E.M. (statistical standard error of mean) and in tables as means±S.D. (standard deviation). The Student t-test (paired or unpaired, one-sided or two-sided) was used in order to determine statistically significant differences between groups. Significant differences between different groups were determined by one-way analysis of variance (ANOVA), with post-hoc tests as per Bonferroni or Dunnett. Survival was compared with log-rank tests (Mantel-Cox tests). The statistical level of significance was established as $P<0.05$.

1.2.11 Characterization of Antibody Binding

Cells: CHO cells were transfected with entire CEACAM1 or with CEACAM1 without N domain (Muturi HAT et al. PLoS One. 2013 Sep. 11; 8(9):e74654.).

ELISA: Sandwich ELISA was coated with 0.25 µg/100 microL/well of anti-CEA (Dako). ELISA was washed and remaining binding sites blocked. Subsequently, CEACAM1 or CEACAM1deltaN (therefore CEACAM1 without N-domain, CEACAM1dN) was added thereto. CEACAM1 and CEACAM1deltaN were obtained from CHO transfectants. The ELISA was then incubated with differing antibodies. After 4 hours of incubation, the ELISA was washed and incubated with anti-mouse Ig-HRP. After 1 hour, the substrate TMB was added and the absorption measured at 450 nm.

FACS: For analysis of antibody binding to human immune cells, PBMCs (=peripheral blood mononuclear cells) were incubated for at least 20 minutes at 4° C. with anti-CEACAM1 antibodies. Thereafter, the cells were washed and anti-mice IgG-APC (eBioscience) together with anti-CD8 antibodies (eBioscience) were added thereto. After 30 minutes, the cells were washed and the fluorescence measured in FACS.

1.2.12 Activation of T Cells

In vitro Activation of CD8$^+$ T cells: In order to analyze the effect of anti-CEACAM1 antibody on the proliferation of CD8+ T cells, PBMCs of HLA-A2+CMV+ healthy donors were incubated together with CMV peptide PP65-73 or influenza matrix peptide 57-68 together with IL2 in RPMI 10% human serum for 10 to 13 days. Thereafter, the cells were restimulated with antigen and intracellular IFN-gamma was measured.

Intracellular cytokine staining: 100 000 cells were transferred to 96-well plate (U-shaped bottom). Cells were treated with peptide 1 (1 µg/ml) or left untreated. After 2 hours, Brefeldin A was added (Sigma). After a further 6 to 8 hours, cells were incubated with anti-CD8 antibody (eBiosciences). Cells were then fixed for 10 minutes with formalin (2% in PBS) and washed 2× with saponin in FACS buffer. Subsequently, cells were incubated with anti-IFN-gamma antibody (eBiosciences) and the fluorescence was measured in the FACS.

Results: The experimental results are shown in the tables hereinafter:

Table 2, B3-17, but not 18-20 and 6G5J can bind in the absence of N domains: the table shows the binding of the antibodies B3-17, 18-20 and 6G5J to CEACAM1 and CEACAM1 without N-domain (=CEACAM1dN) measured in the ELISA. The table shows means±SD (standard deviation) of the absorption at 450 nm. The binding of antibody 18-20 to CEACAM1 was significantly higher than to CEACAM1 dN (18-20 CEACAM1 versus 18-20 CEACAM1 dN, $p<0.05$, t-test). The binding of 6G5J to CEACAM1 was significantly higher than to CEACAM1 dN (6G5J CEACAM1 versus 6G5J CEACAM1 dN p<0.05, t-test). The binding of B3-17 to CEACAM1 was not higher than to CEACAM1 dN (B3-17 CEACAM1 versus B3-17 CEACAM1 dN).

TABLE 2

|  | WT (Mean ± SD, n) | CEACAM1 (Mean ± SD, n) | CEACAM1 dN (Mean ± SD, n) |
| --- | --- | --- | --- |
| B3-17 | 0.05 ± 0.003, 3 | 0.62 ± 0.048, 3 | 0.910 ± 0.056, 3 |
| 18-20 | 0.06 ± 0.004, 3 | 1.30 ± 0.093, 3 | 0.053 ± 0.0057, 3 |
| 6G5J | 0.054 ± 0.004, 3 | 1.09 ± 0.088, 3 | 0.066 ± 0.0053, 3 |

The experimental results given in table 2 show that the antibodies that have an antibody binding site $CDR2^H$ of the sequence SEQ ID No. 21 (i.e. antibodies 18-20 and 6G5J), in contrast to the antibody B3-17 that does not have such an antibody binding site $CDR2^H$, bind effectively to the N-domain of CEACAM1.

Table 3: B3-17 and 18-20 bind human $CD8^+$ T cells: the table shows the binding of isotype control and the antibodies B3-17 and 18-20 to $CD8^+$ T cells from the blood of healthy donors. The table shows means±SD of the mean fluorescence intensity. The binding of antibody B3-17 to $CD8^+$ T cells is significantly higher than the binding of isotype p<0.05 (paired t-test). The binding of 18-20 to $CD8^+$ T cells is significantly higher than the binding of isotype p<0.05 (paired t-test).

TABLE 3

|  | Isotype (Mean ± SD, n) | B3-17 (Mean ± SD, n) | 18-20 (Mean ± SD, n) |
| --- | --- | --- | --- |
| Mean ± SD | 436 ± 57.38, 10 | 913 ± 298.80, 10 | 632 ± 72.72, 10 |

The experimental results given in table 3 show that the antibodies also bind to (human) T cells. These were then, in the case of the antibody 18-20 and 6G5J according to the present invention, surprisingly strongly activated (see below tables 4-6), whereas antibody B3-17 had a significantly lower activating effect when stimulated.

Table 4, 18-20, 6G5J, but not B3-17 activates $CD8^+$ T cells: PBMCs of healthy donors were incubated with or without CMV peptide in the presence or absence of isotype control and the antibodies 18-20, 6G5J or B3-17. On day 10, the cells were no longer stimulated or were restimulated for 8 hours with CMV peptide. Intracellular IFN-gamma was measured in the FACS. The table shows the percentage±SD of the IFN-gamma-positive $CD8^+$ T cells. Presence of antibody 18-20 led to the significant increase of the IFN-gamma positive T cells (CMV stimulated versus CMV, 18-20 stimulated, p<0.05, t-test). Presence of B3-17 led to no significant increase in IFN-gamma positive T cells (CMV stimulated versus CMV, B3-17 stimulated, p=0.344, t-test). 18-20 stimulates significantly better than B3-17 (CMV, 18-20 stimulated versus CMV, B3-17 stimulated, p<0.05, t-test).

TABLE 4

|  | Not stimulated (Mean ± SD, n) | Stimulated (Mean ± SD, n) |
| --- | --- | --- |
| None | 0.111 ± 0.104, 3 | 0.367 ± 0.048, 3 |
| CMV | 0.177 ± 0.131, 3 | 0.540 ± 0.287, 3 |
| CMV + Isotype | 0.221, 2 | 0.372, 2 |
| CMV + 18-20 | 0.296 ± 0.165, 3 | 3.876 ± 2.598, 3 |

TABLE 4-continued

|  | Not stimulated (Mean ± SD, n) | Stimulated (Mean ± SD, n) |
| --- | --- | --- |
| CMV + 6G5J | 0.112 ± 0.067, 3 | 2.951 ± 2.200, 3 |
| CMV + B3-17 | 0.219 ± 0.148, 3 | 0.465 ± 0.095, 3 |

Table 5, 18-20 activates influenza-specific $CD8^+$ T cells: PBMCs of healthy donors were incubated with influenza-peptide together with anti-CD28 in the presence or absence of 18-20 antibody. After 13 days, the cells were restimulated with influenza peptide and after 6 hours intracellular IFN-gamma was measured. The table shows the percentage±SD of the IFN-gamma positive $CD8^+$ T cells. The presence of antibody 18-20 led to significantly more IFN-gamma-producing T cells (CD28 stimulated versus CD28+18-20 stimulated, p<0.05 t-test).

TABLE 5

|  | Not stimulated (Mean ± SD, n) | Stimulated (Mean ± SD, n) |
| --- | --- | --- |
| CD28 | 1.12 ± 1.99, 5 | 4.08 ± 4.33, 8 |
| CD28 + 18-20 | 0.217 ± 0.150, 3 | 11.74 ± 9.914, 10 |

Table 6, humanized 18-20 activates human $CD8^+$ T cells: PBMCs of healthy donors were incubated with or without CMV peptide in the presence or absence of humanized 18-20 antibody. On day 10, the cells were restimulated with CMV peptide and after 8 hours, intracellular IFN-gamma in the FACS was measured. Table shows percentage±SD of the IFN-gamma positive $CD8^+$ T cells. The presence of humanized antibody 18-20 led to a significant increase in the IFN-gamma-positive T cells (CMV stimulated versus CMV+hu18-20 stimulated, p<0.05, t-test).

TABLE 6

|  | Not stimulated (Mean ± SD, n) | Stimulated (Mean ± SD, n) |
| --- | --- | --- |
| None | 0.106 ± 0.109, 3 | 0.211 ± 0.017, 3 |
| CMV | 0.186 ± 0.180, 3 | 2.64 ± 3.049, 3 |
| CM + hu18-20 | 0.456 ± 0.250, 3 | 7.44 ± 5.57, 3 |

The following binding values were determined for binding of the antibody to CEACAM1:

Antibody 18-20: $K_d$ 26 nM; $K_{on}$: $1.2 \times 10^{-4}$; $K_{off}$: $3.5 \times 10^{-4}$
Antibody 6G5J: $K_d$ 23 nM; $K_{on}$: $1.0 \times 10^{-4}$; $K_{off}$: $3.1 \times 10^{-4}$
Antibody B3-17: $K_d$ 10 nM; $K_{on}$: $3.4 \times 10^{-4}$; $K_{off}$: $3.4 \times 10^{-4}$ All three antibodies are accordingly binding in the lower double figure nanomolar range. The differences in the activation of the T cells therefore do not arise via different total binding strengths, but via the targeted binding to the N-domain of the CEACAM1 by the antibodies 18-20 and 6G5J according to the present invention.

Further preferred embodiments:

The present invention also relates to a substance for application in the therapy of viral infections and/or viral infectious diseases, wherein the substance activates the expression and/or function of CEACAM1.

In addition, the present invention relates to a substance for application in the therapy of B-cell-dependent diseases, wherein the substance inhibits the expression and/or function of CEACAM1.

In addition, the present invention relates to a substance for application in the diagnosis of viral infections, viral infectious diseases and/or B-cell-dependent diseases, wherein the substance is used for detection of the expression and/or function of CEACAM1.

The present invention further relates to an antibody, a therapeutic antibody, a variable antibody heavy chain ($V_H$) domain, a variable antibody light chain ($V_L$) domain, an isolated nucleic acid encoding a variable antibody heavy chain ($V_H$) domain, an isolated nucleic acid encoding a variable antibody light chain ($V_L$) domain, a hybridoma cell and also a method for producing an antibody.

Further preferred embodiments are:

1. Substance for application in the therapy of viral infections and/or viral infectious diseases, characterized in that the substance activates the expression and/or function of CEACAM1.
2. Substance according to embodiment 1, characterized in that CEACAM1 is CEACAM1 as per SEQ ID No. 1.
3. Substance according to embodiment 1 or 2, characterized in that the substance is a substance directed against CEACAM1.
4. Substance according to any one of the preceding embodiments, characterized in that the substance is an antibody directed against CEACAM1 (anti-CEACAM1 antibody).
5. Substance according to embodiment 4, characterized in that the antibody comprises a variable antibody heavy chain ($V_H$) domain selected from the group consisting of variable antibody heavy chain ($V_H$) domain as per SEQ ID No. 3, variable antibody heavy chain ($V_H$) domain as per SEQ ID No. 7 and variable antibody heavy chain ($V_H$) domain as per SEQ ID No. 11, and/or a variable antibody light chain ($V_L$) domain selected from the group consisting of variable antibody light chain ($V_L$) domain as per SEQ ID No. 5, variable antibody light chain ($V_L$) domain as per SEQ ID No. 9 and variable antibody light chain ($V_L$) domain as per SEQ ID No. 13.
6. Substance according to one of embodiments 1 to 3, characterized in that the substance is the soluble protein UspA1 of *Moraxella catarrhalis* as per SEQ ID No. 15.
7. Substance according to one of embodiments 1 to 3, characterized in that the substance is the soluble protein Opa of *Neisseria gonorrhoeae* as per SEQ ID No. 17.
8. Substance according to one of embodiments 1 to 3, characterized in that the substance is the soluble variable protein P5 of *Haemophilus* influenza as per SEQ ID No. 18.
9. Substance according to one of embodiments 1 to 3, characterized in that the substance is the soluble human recombinant CEACAM1 fusion protein as per SEQ ID No. 19.
10. Substance according to one of the preceding embodiments, characterized in that the viral infections and/or infectious diseases are selected from the group consisting of viral hepatitis, hepatitis B, hepatitis C, HIV infection, Aids, influenza, poliomyelitis, virus-induced myocarditis, glandular fever, herpes simplex, cytomegalie, rabies and Ebola.
11. Drug for application in the therapy of viral infections and/or viral infectious diseases containing at least one substance according to one of the preceding embodiments.
12. Antibody comprising a variable antibody heavy chain ($V_H$) domain as per SEQ ID No. 3 and/or a variable antibody light chain ($V_L$) domain as per SEQ ID No. 5.
13. Therapeutic antibody comprising a variable antibody heavy chain ($V_H$) domain that is selected from the group consisting of variable antibody heavy chain ($V_H$) domain as per SEQ ID No. 3, variable antibody heavy chain ($V_H$) domain as per SEQ ID No. 7 and antibody heavy chain ($V_H$) domain as per SEQ ID No. 11, and/or a variable antibody light chain ($V_L$) domain which is selected from the group consisting of variable antibody light chain ($V_L$) domain as per SEQ ID No. 5, variable antibody light chain ($V_L$) domain as per SEQ ID No. 9 and antibody light chain ($V_L$) domain as per SEQ ID No. 13.
14. Variable antibody heavy chain ($V_H$) domain as per SEQ ID No. 3 or SEQ ID No. 7.
15. Variable antibody light chain ($V_L$) domain as per SEQ ID No. 5 or SEQ ID No. 9.
16. Isolated nucleic acid encoding a variable antibody heavy chain ($V_H$) domain, wherein the nucleic acid comprises a nucleotide sequence or consists of a nucleotide sequence that is selected from the group consisting of SEQ ID No. 4 and SEQ ID No. 8.
17. Isolated nucleic acid encoding a variable antibody light chain ($V_L$) domain, wherein the nucleic acid comprises a nucleotide sequence or consists of a nucleotide sequence that is selected from the group consisting of SEQ ID No. 6 and SEQ ID No. 10.
18. Hybridoma cell that produces an antibody according to embodiment 12 or 13.
19. Method for producing an antibody, in particular an antibody according to embodiment 12 or 13, comprising the following steps:
    a) fusing B cells, which originate from an experimental animal immunized against an antigen, and myeloma cells, forming hybridoma cells,
    b) selecting the hybridoma cells,
    c) isolating hybridoma cells that produce antibodies directed against the antigen,
    characterized in that the antigen is CEACAM1 as per SEQ ID No. 1 or a fragment, in particular epitope, thereof.

The present invention is not limited to embodiments described herein; reference should be had to the appended claims.

What is claimed is:

1. An anti-CEACAM1 antibody comprising:
   at least one antibody heavy chain ($V_H$) domain comprising antigen binding sites $CDR1^H$, $CDR2^H$ and $CDR3^H$; and
   at least one antibody light chain ($V_L$) domain comprising antigen binding sites $CDR1^L$, $CDR2^L$ and $CDR3^L$,
   wherein,
   the antigen binding site $CDR1^H$ has the amino acid sequence GYTFTVYGMN (SEQ ID No. 26),
   the antigen binding site $CDR2^H$ has the amino acid sequence WINTYTGEPT, (SEQ ID No. 21)

the antigen binding site $CDR3^H$ has the amino acid sequence YRYDGGMDY (SEQ ID No. 34),
   the antigen binding site $CDR1^L$ has the amino acid sequence KASQDINKFLA (SEQ ID No. 30),
   the antigen binding site $CDR2^L$ has the amino acid sequence YTSTLQP (SEQ ID No. 23), and
   the antigen binding site $CDR3^L$ has the amino acid sequence LQYDNLYT (SEQ ID No. 37).

2. An anti-CEACAM1 antibody comprising:
   at least one antibody heavy chain (VH) domain comprising antigen binding sites $CDR1^H$, $CDR2^H$ and $CDR3^H$; and
   at least one antibody light chain (VL) domain comprising antigen binding sites $CDR1^L$, $CDR2^L$ and $CDR3^L$,
   wherein,
   the antigen binding site $CDR1^H$ has the amino acid sequence GYIFRNYGMK (SEQ ID No. 27),
   the antigen binding site $CDR2^H$ has the amino acid sequence WINTYTGEPT (SEQ ID No. 21),
   the antigen binding site $CDR3^H$ has the amino acid sequence ITTSNYALDN (SEQ ID No. 35),
   the antigen binding site $CDR1^L$ has the amino acid sequence RASQDISNYLN (SEQ ID No. 31),
   the antigen binding site $CDR2^L$ has the amino acid sequence YTSKLHS (SEQ ID No. 24), and
   the antigen binding site $CDR3^L$ has the amino acid sequence QQGNTLPWT (SEQ ID No. 38).

3. A humanized anti-CEACAM1 antibody comprising:
   at least one antibody heavy chain (VH) domain comprising antigen binding sites $CDR1^H$, $CDR2^H$ and $CDR3^H$; and
   at least one antibody light chain (VL) domain comprising antigen binding sites $CDR1^L$, $CDR2^L$ and $CDR3^L$,
   wherein,
   the antigen binding site $CDR1^H$ has the amino acid sequence GYTFTTYVMH at positions 19-28 of SEQ ID No. 11,
   the antigen binding site $CDR2^H$ has the amino acid sequence FFNPYNDGTK at positions 43-52 of SEQ ID No. 11,
   the antigen binding site $CDR3^H$ has the amino acid sequence WAYDGSYAY at positions 92-100 of SEQ ID No. 11,
   the antigen binding site $CDR1^L$ has the amino acid sequence KASDHINNWLA at positions 16-26 of SEQ ID No. 13,
   the antigen binding site $CDR2^L$ has the amino acid sequence GATSLET at positions 42-48 of SEQ ID No. 13, and
   the antigen binding site $CDR3^L$ has the amino acid sequence QQYWRTPFT at positions 81-89 of SEQ ID No. 13.

4. A nucleic acid encoding the anti-CEACAM1 antibody as recited in claim 1.

5. A nucleic acid encoding the anti-CEACAM1 antibody as recited in claim 2.

6. A nucleic acid encoding the anti-CEACAM1 antibody as recited in claim 3.

7. A method for activating T cells in vitro, the method comprising:
   providing non-activated T cells;
   contacting the non-activated T cells with:
      an anti-CEACAM1 antibody as recited in claim 1, and
      an epitope directed against the T cells, thereby treating the T cells; and
   culturing the treated T cells under conditions that do not hinder an activation of the T cells.

8. A method for activating T cells in vitro, the method comprising:
   providing non-activated T cells;
   contacting the non-activated T cells with:
      an anti-CEACAM1 antibody as recited in claim 2, and
      an epitope directed against the T cells, thereby treating the T cells; and
   culturing the treated T cells under conditions that do not hinder an activation of the T cells.

* * * * *

SEQUENCE LISTING

```
<160> NUMBER OF SEQ ID NOS: 43

<210> SEQ ID NO 1
<211> LENGTH: 1806
<212> TYPE: DNA
<213> ORGANISM: Homo sapiens

<400> SEQUENCE: 1
cagctgacca ccgagagcat gcccttcaac gtggccgagg gcaaggaggt gctgctgctg      60
```

-continued

```
gtgcacaacc tgccccagca gctgttcggc tacagctggt acaagggcga gagggtggac      120
ggcaacaggc agatcgtggg ctacgccatc ggcacccagc aggccacccc cggccccgcc      180
aacagcggca gggagaccat ctaccccaac gccagcctgc tgatccagaa cgtgacccag      240
aacgacaccg gcttctacac cctgcaggtg atcaagagcg acctggtgaa cgaggaggcc      300
accggccagt ccacgtgta ccccgagctg cccaagccca gcatcagcag caacaacagc      360
aaccccgtgg aggacaagga cgccgtggcc ttcacctgcg agcccgagac caggacacc      420 acctacctgt ggtggatcaa caaccagagc ctgcccgtga gccccaggct gcagctgagc      480
aacggcaaca ggaccctgac cctgctgagc gtgaccagga cgacaccgg ccctacgag       540 tgcgagatcc agaacccgt gagcgccaac aggagcgacc ccgtgaccct gaacgtgacc       600 tacgccccg acacccccac catcagcccc agcgacacct actacaggcc cggcgccaac       660
ctgagcctga gctgctacgc cgccagcaac ccccccgccc agtacagctg gctgatcaac       720
ggcaccttcc agcagagcac ccaggagctg ttcatcccca acatcaccgt gaacaacagc       780
ggcagctaca cctgccacgc caacaacagc gtgaccggct gcaacaggac caccgtgaag       840
accatcatcg tgaccgagct gagccccgtg gtggccaagc cccagatcaa ggccagcaag       900
accaccgtga ccggcgacaa ggacagcgtg aacctgacct gcagcaccaa cgacaccggc       960
atcagcatca ggtggttctt caagaaccag agcctgccca gcagcgagag gatgaagctg      1020
agccagggca caccaccct gagcatcaac cccgtgaaga gggaggacgc cggcacctac      1080
tggtgcgagg tgttcaaccc catcagcaag aaccagagcg accccatcat gctgaacgtg      1140
gagtgcccac cttgcccagc accacctgtg gcaggacctt cagtcttcct cttcccccca      1200
aaacccaagg acaccctcat gatctcccgg acccctgagg tcacatgcgt ggtggtggac      1260
gtgagccacg aagaccctga ggtcaagttc aactggtacg tggacggcgt ggaggtgcat      1320
aatgccaaga caaagccgcg ggaggagcag tacaacagca cgtaccgtgt ggtcagcgtc      1380
ctcaccgtcc tgcaccagga ctggctgaat ggcaaggagt acaagtgcaa ggtctccaac      1440
aaaggcctcc catcctccat cgagaaaacc atctccaaag ccaaagggca gccccgagaa      1500
ccacaggtgt acaccctgcc cccatcccgg gaggagatga ccaagaacca ggtcagcctg      1560
acctgcctgg tcaaaggctt ctatcccagc gacatcgccg tggagtggga gagcaatggg      1620
cagccggaga acaactacaa gaccacgcct cccgtgctgg actccgacgg ctccttcttc      1680
ctctacagca agctcaccgt ggacaagagc aggtggcagc aggggaacgt cttctcatgc      1740
tccgtgatgc atgaggctct gcacaaccac tacacgcaga agagcctctc cctgtctccg      1800
ggtaaa                                                                1806
```

<210> SEQ ID NO 2
<211> LENGTH: 1895
<212> TYPE: DNA
<213> ORGANISM: Homo sapiens

<400> SEQUENCE: 2

```
cctgagatca ccggcgaagg agggccacca tgtacaggat gcaactcctg tcttgcattg       60
cactaagtct tgcacttgtc acgaattcgc agctgaccac cgagagcatg cccttcaacg      120
tggccgaggg caaggaggtg ctgctgctgg tgcacaacct gccccagcag ctgttcggct      180
acagctggta caagggcgag agggtggacg gcaacaggca gatcgtgggc tacgccatcg      240
gcacccagca ggccaccccc ggccccgcca acagcggcag ggagaccatc taccccaacg      300
```

| | |
|---|---|
| ccagcctgct gatccagaac gtgacccaga acgacaccgg cttctacacc ctgcaggtga | 360 |
| tcaagagcga cctggtgaac gaggaggcca ccggccagtt ccacgtgtac ccgagctgc | 420 |
| ccaagcccag catcagcagc aacaacagca accccgtgga ggacaaggac gccgtggcct | 480 |
| tcacctgcga gcccgagacc caggacacca cctacctgtg gtggatcaac aaccagagcc | 540 |
| tgcccgtgag ccccaggctg cagctgagca acggcaacag gaccctgacc ctgctgagcg | 600 |
| tgaccaggaa cgacaccggc ccctacgagt gcgagatcca gaaccccgtg agcgccaaca | 660 |
| ggagcgaccc cgtgaccctg aacgtgacct acggccccga cacccccacc atcagcccca | 720 |
| gcgacaccta ctacaggccc ggcgccaacc tgagcctgag ctgctacgcc gccagcaacc | 780 |
| cccccgccca gtacagctgg ctgatcaacg gcaccttcca gcagagcacc caggagctgt | 840 |
| tcatccccaa catcaccgtg aacaacagcg gcagctacac ctgccacgcc aacaacagcg | 900 |
| tgaccggctg caacaggacc accgtgaaga ccatcatcgt gaccgagctg agccccgtgg | 960 |
| tggccaagcc ccagatcaag gccagcaaga ccaccgtgac cggcgacaag acagcgtga | 1020 |
| acctgacctg cagcaccaac gacaccggca tcagcatcag gtggttcttc aagaaccaga | 1080 |
| gcctgcccag cagcgagagg atgaagctga gccagggcaa caccaccctg agcatcaacc | 1140 |
| ccgtgaagag ggaggacgcc ggcacctact ggtgcgaggt gttcaacccc atcagcaaga | 1200 |
| accagagcga ccccatcatg ctgaacgtgg agtgcccacc ttgcccagca ccacctgtgg | 1260 |
| caggaccttc agtcttcctc ttccccccaa acccaagga caccctcatg atctcccgga | 1320 |
| cccctgaggt cacatgcgtg gtggtggacg tgagccacga agaccctgag gtcaagttca | 1380 |
| actggtacgt ggacggcgtg gaggtgcata atgccaagac aaagccgcgg gaggagcagt | 1440 |
| acaacagcac gtaccgtgtg gtcagcgtcc tcaccgtcct gcaccaggac tggctgaatg | 1500 |
| gcaaggagta caagtgcaag gtctccaaca aaggcctccc atcctccatc gagaaaacca | 1560 |
| tctccaaagc caaagggcag ccccgagaac acaggtgta caccctgccc ccatcccggg | 1620 |
| aggagatgac caagaaccag gtcagcctga cctgcctggt caaaggcttc tatcccagcg | 1680 |
| acatcgccgt ggagtgggag agcaatgggc agccggagaa caactacaag accacgcctc | 1740 |
| ccgtgctgga ctccgacggc tccttcttcc tctacagcaa gctcaccgtg gacaagagca | 1800 |
| ggtggcagca ggggaacgtc ttctcatgct ccgtgatgca tgaggctctg cacaaccact | 1860 |
| acacgcagaa gagcctctcc ctgtctccgg gtaaa | 1895 |

<210> SEQ ID NO 3
<211> LENGTH: 110
<212> TYPE: PRT
<213> ORGANISM: Mus musculus

<400> SEQUENCE: 3

Lys Pro Gly Glu Thr Val Lys Ile Ser Cys Lys Thr Ser Gly Tyr Ile
1               5                   10                  15

Phe Arg Asn Tyr Gly Met Lys Trp Val Lys Gln Ala Pro Gly Lys Gly
            20                  25                  30

Leu Lys Trp Met Gly Trp Ile Asn Thr Tyr Thr Gly Glu Pro Thr Tyr
        35                  40                  45

Ala Asp Asp Phe Lys Gly Arg Phe Ala Phe Ser Leu Glu Thr Ser Ala
    50                  55                  60

Ser Thr Ala Tyr Leu Gln Ile Asn Asn Leu Lys Asn Glu Asp Met Ala
65                  70                  75                  80

Thr Tyr Phe Cys Ala Arg Arg Gly Met Ile Thr Thr Ser Asn Tyr Ala
                85                  90                  95

Leu Asp Asn Trp Gly Gln Gly Thr Ser Val Thr Val Ser Ser
            100                 105                 110

<210> SEQ ID NO 4
<211> LENGTH: 331
<212> TYPE: DNA
<213> ORGANISM: Mus musculus

<400> SEQUENCE: 4
aagcctggag agacagtcaa gatctcctgc aagacttctg ggtatatatt cagaaactat      60
ggaatgaaat gggtgaagca ggctccagga aagggtttaa agtggatggg ctggataaac     120
acctatactg gagagccaac atatgctgat gacttcaagg gacggtttgc cttctctttg     180
gaaacctctg ccagcactgc ctatttgcag atcaacaacc tcaaaaatga ggacatggct     240
acatatttct gtgcaagaag ggggatgatt acgacgagta attatgctct ggacaactgg     300
ggtcaaggaa cctcagtcac cgtctcctca g                                    331

<210> SEQ ID NO 5
<211> LENGTH: 99
<212> TYPE: PRT
<213> ORGANISM: Mus musculus

<400> SEQUENCE: 5

Ser Ser Leu Ser Ala Ser Leu Gly Asp Arg Val Thr Ile Ser Cys Arg
1               5                   10                  15

Ala Ser Gln Asp Ile Ser Asn Tyr Leu Asn Trp Tyr Gln Gln Lys Pro
            20                  25                  30

Asp Gly Thr Ile Lys Leu Leu Ile Tyr Tyr Thr Ser Lys Leu His Ser
        35                  40                  45

Gly Val Pro Ser Arg Phe Ser Gly Ser Gly Ser Gly Thr Asp Tyr Ser
    50                  55                  60

Leu Thr Ile Ser Asn Leu Asp Gln Glu Asp Ile Ala Thr Tyr Phe Cys
65                  70                  75                  80

Gln Gln Gly Asn Thr Leu Pro Trp Thr Phe Gly Gly Gly Thr Lys Leu
                85                  90                  95

Glu Ile Lys

<210> SEQ ID NO 6
<211> LENGTH: 298
<212> TYPE: DNA
<213> ORGANISM: Mus musculus

<400> SEQUENCE: 6 tcctcccctgt ctgcctctct gggagacaga gtcaccatca gttgcagggc aagtcaggac      60
attagcaatt atttaaactg gtatcagcag aaaccagatg gaactattaa actcctgatc     120
tactacacat caaagttaca ctcaggagtc ccatcaagat tcagtggcag tgggtctgga     180
acagattatt ctctcaccat tagcaacctg gaccaggaag atattgccac ttactttgc     240 caacagggta atactcttcc gtggacgttc ggtggaggca ccaagctgga aatcaaac      298

<210> SEQ ID NO 7
<211> LENGTH: 109
<212> TYPE: PRT
<213> ORGANISM: Mus musculus

<400> SEQUENCE: 7

Lys Pro Gly Glu Thr Val Lys Ile Ser Cys Lys Ala Ser Gly Tyr Thr

```
            1               5                  10                 15
         Phe Thr Val Tyr Gly Met Asn Trp Val Lys Gln Ala Pro Gly Lys Asp
                         20                  25                  30

Leu Lys Trp Met Gly Trp Ile Asn Thr Tyr Thr Gly Glu Pro Thr Tyr
                         35                  40                  45

Ala Asp Asp Phe Lys Gly Arg Phe Ala Phe Ser Leu Glu Thr Ser Ala
                 50                  55                  60

Ser Thr Ala Tyr Leu Gln Ile Asn Asn Leu Lys Asn Glu Asp Met Ala
         65                  70                  75                  80

Thr Tyr Phe Cys Ala Arg Lys Ala Phe Tyr Arg Tyr Asp Gly Gly Met
                         85                  90                  95

Asp Tyr Trp Gly Gln Gly Thr Ser Val Thr Val Ser Ser
                         100                 105
```

<210> SEQ ID NO 8
<211> LENGTH: 328
<212> TYPE: DNA
<213> ORGANISM: Mus musculus

<400> SEQUENCE: 8

```
aagcctggag agacagtcaa gatctcctgc aaggcttctg gtataccttt cacagtctat        60
ggaatgaact gggtgaagca ggctccagga aaggatttaa agtggatggg ctggataaac       120
acctacactg gagagccaac atatgctgat gacttcaagg gacggtttgc cttctctttg       180
gaaacctctg ccagcactgc ctatttgcag atcaacaacc tcaaaaatga ggacatggct       240
acatatttct gtgcaagaaa ggccttctat aggtacgacg ggggtatgga ctactggggt       300
caaggaacct cagtcaccgt ctcctcag                                          328
```

<210> SEQ ID NO 9
<211> LENGTH: 98
<212> TYPE: PRT
<213> ORGANISM: Mus musculus

<400> SEQUENCE: 9

```
         Ser Ser Leu Ser Ala Ser Leu Gly Gly Lys Val Thr Ile Thr Cys Lys
         1               5                  10                  15

Ala Ser Gln Asp Ile Asn Lys Phe Leu Ala Trp Tyr Gln His Lys Pro
                         20                  25                  30

Gly Lys Gly Pro Arg Leu Leu Ile His Tyr Thr Ser Thr Leu Gln Pro
                         35                  40                  45

Gly Ile Pro Ser Arg Phe Ser Gly Ser Gly Ser Gly Arg Asp Tyr Ser
                 50                  55                  60

Phe Ser Ile Ser Asn Leu Glu Pro Glu Asp Ile Ala Thr Tyr Tyr Cys
         65                  70                  75                  80

Leu Gln Tyr Asp Asn Leu Tyr Thr Phe Gly Gly Gly Thr Lys Leu Glu
                         85                  90                  95

Ile Lys
```

<210> SEQ ID NO 10
<211> LENGTH: 295
<212> TYPE: DNA
<213> ORGANISM: Mus musculus

<400> SEQUENCE: 10

```
tcctcactgt ctgcatctct gggaggcaaa gtcaccatca cttgcaaggc aagccaagac        60
attaacaagt ttttagcttg gtaccaacac aagcctggaa aaggtcctag gctgctcata       120
```

```
cattacacat ctacattaca gccaggcatc ccatcaaggt tcagtggaag tgggtctggg    180
agagattatt ccttcagcat cagcaacctg gagcctgaag atattgcaac ttattattgt    240
ctacaatatg ataatctgta cacgttcggt gggggaccca agctggaaat aaaac         295
```

<210> SEQ ID NO 11
<211> LENGTH: 111
<212> TYPE: PRT
<213> ORGANISM: Mus musculus

<400> SEQUENCE: 11

```
Gly Pro Glu Leu Val Lys Pro Gly Thr Ser Val Lys Met Ser Cys Lys
1               5                   10                  15

Ala Ser Gly Tyr Thr Phe Thr Thr Tyr Val Met His Trp Val Gln Gln
            20                  25                  30

Lys Pro Gly Gln Gly Leu Asp Trp Ile Gly Phe Phe Asn Pro Tyr Asn
        35                  40                  45

Asp Gly Thr Lys Tyr Asn Glu Lys Phe Lys Gly Lys Ala Thr Leu Thr
    50                  55                  60

Ser Asp Lys Ser Ser Ser Thr Ala Tyr Met Glu Leu Ser Ser Leu Thr
65                  70                  75                  80

Ser Glu Asp Ser Ala Val Tyr Tyr Cys Ala Arg Trp Ala Tyr Asp Gly
                85                  90                  95

Ser Tyr Ala Tyr Trp Gly Gln Gly Thr Thr Leu Thr Val Ser Ser
            100                 105                 110
```

<210> SEQ ID NO 12
<211> LENGTH: 334
<212> TYPE: DNA
<213> ORGANISM: Mus musculus

<400> SEQUENCE: 12

```
ggacctgagc tggtaaagcc tgggacttca gtgaagatgt cctgcaaggc ttctggatac    60
acattcacta cctatgttat gcactgggtg caacagaagc ctgggcaggg ccttgactgg    120
attggatttt ttaatcctta caatgatggt actaagtaca atgagaagtt caaaggcaag    180
gccacactga cttcagacaa atcctccagc acagcctaca tggaactcag cagcctgacc    240
tctgaggact ctgcggtcta ttactgtgca gatgggcct acgatggtag ctacgcctac    300
tggggccaag gcaccactct cacagtctcc tcag                                 334
```

<210> SEQ ID NO 13
<211> LENGTH: 99
<212> TYPE: PRT
<213> ORGANISM: Mus musculus

<400> SEQUENCE: 13

```
Ser Tyr Leu Ser Val Phe Leu Gly Gly Arg Val Thr Ile Thr Cys Lys
1               5                   10                  15

Ala Ser Asp His Ile Asn Asn Trp Leu Ala Trp Tyr Gln Gln Lys Pro
            20                  25                  30

Gly Asn Ala Pro Arg Leu Leu Ile Ser Gly Ala Thr Ser Leu Glu Thr
        35                  40                  45

Gly Val Pro Ser Arg Phe Ser Gly Ser Gly Ser Gly Lys Asp Tyr Thr
    50                  55                  60

Leu Ser Ile Ile Ser Leu Gln Thr Glu Asp Val Ala Thr Tyr Tyr Cys
65                  70                  75                  80
```

```
Gln Gln Tyr Trp Arg Thr Pro Phe Thr Phe Gly Ser Gly Thr Lys Leu
                85                  90                  95

Glu Ile Lys
```

```
<210> SEQ ID NO 14
<211> LENGTH: 298
<212> TYPE: DNA
<213> ORGANISM: Mus musculus

<400> SEQUENCE: 14
tcctacttgt ctgtatttct aggaggcaga gtcaccatta cttgcaaggc aagtgaccac      60
attaataatt ggttagcctg gtatcagcag aaaccaggaa atgctcctag gctcttaata     120 tctgggcaa ccagtttgga aactggggtt ccttcaagat tcagtggcag tggatctgga     180
aaggattaca ctctcagcat tatcagtctt cagactgaag atgttgctac ttattactgt     240
caacagtatt ggagaactcc attcacgttc ggctcgggga caaagttgga aataaaac       298
```

```
<210> SEQ ID NO 15
<211> LENGTH: 892
<212> TYPE: PRT
<213> ORGANISM: Moraxella catarrhalis

<400> SEQUENCE: 15

Met Asn Lys Ile Tyr Lys Val Lys Lys Asn Ala Ala Gly His Leu Val
1               5                   10                  15

Ala Cys Ser Glu Phe Ala Lys Gly His Thr Lys Lys Ala Val Leu Gly
                20                  25                  30

Ser Leu Leu Ile Val Gly Ala Leu Gly Met Ala Thr Thr Ala Ser Ala
            35                  40                  45

Gln Ala Thr Lys Gly Thr Gly Lys His Val Val Asp Asn Lys Asp Asn
        50                  55                  60

Lys Ala Lys Gly Asp Tyr Ser Thr Ala Ser Gly Gly Lys Asp Asn Glu
65                  70                  75                  80

Ala Lys Gly Asn Tyr Ser Thr Val Gly Gly Asp Tyr Asn Glu Ala
                85                  90                  95

Lys Gly Asn Tyr Ser Thr Val Gly Gly Ser Ser Asn Thr Ala Lys
            100                 105                 110

Gly Glu Lys Ser Thr Ile Gly Gly Gly Asp Thr Asn Asp Ala Asn Gly
        115                 120                 125

Thr Tyr Ser Thr Ile Gly Gly Gly Tyr Tyr Ser Arg Ala Ile Gly Asp
        130                 135                 140

Ser Ser Thr Ile Gly Gly Gly Tyr Tyr Asn Gln Ala Thr Gly Glu Lys
145                 150                 155                 160

Ser Thr Val Ala Gly Gly Arg Asn Asn Gln Ala Thr Gly Asn Asn Ser
                165                 170                 175

Thr Val Ala Gly Gly Ser Tyr Asn Gln Ala Thr Gly Asn Asn Ser Thr
            180                 185                 190

Val Ala Gly Gly Ser His Asn Gln Ala Thr Gly Glu Gly Ser Phe Ala
        195                 200                 205

Ala Gly Val Glu Asn Lys Ala Asn Ala Asn Ala Val Ala Leu Gly
        210                 215                 220

Lys Asn Asn Thr Ile Asp Gly Asp Asn Ser Val Ala Ile Gly Ser Asn
225                 230                 235                 240

Asn Thr Ile Asp Ser Gly Lys Gln Asn Val Phe Ile Leu Gly Ser Ser
                245                 250                 255
```

```
Thr Asn Thr Thr Asn Ala Gln Ser Gly Ser Val Leu Leu Gly His Asn
                260                 265                 270

Thr Ala Gly Lys Lys Ala Thr Ala Val Ser Ser Ala Lys Val Asn Gly
                275                 280                 285

Leu Thr Leu Gly Asn Phe Ala Gly Ala Ser Lys Thr Gly Asn Gly Thr
                290                 295                 300

Val Ser Val Gly Ser Glu Asn Asn Glu Arg Gln Ile Val Asn Val Gly
305                 310                 315                 320

Ala Gly Asn Ile Ser Ala Asp Ser Thr Asp Ala Val Asn Gly Ser Gln
                325                 330                 335

Leu Tyr Ala Leu Ala Thr Ala Val Lys Ala Asp Ala Asp Glu Asn Phe
                340                 345                 350

Lys Ala Leu Thr Lys Thr Gln Asn Thr Leu Ile Glu Gln Gly Glu Ala
                355                 360                 365

Gln Asp Ala Leu Ile Ala Gln Asn Gln Thr Asp Ile Thr Ala Asn Lys
                370                 375                 380

Thr Ala Ile Glu Arg Asn Phe Asn Arg Thr Val Val Asn Gly Phe Glu
385                 390                 395                 400

Ile Glu Lys Asn Lys Ala Gly Ile Ala Lys Asn Gln Ala Asp Ile Gln
                405                 410                 415

Thr Leu Glu Asn Asn Val Gly Glu Leu Leu Asn Leu Ser Gly Arg
                420                 425                 430

Leu Leu Asp Gln Lys Ala Asp Ile Asp Asn Asn Ile Asn Ile Tyr
                435                 440                 445

Asp Leu Ala Gln Gln Asp Gln His Ser Ser Asp Ile Lys Thr Leu
450                 455                 460

Lys Lys Asn Val Glu Glu Gly Leu Leu Asp Leu Ser Gly Arg Leu Ile
465                 470                 475                 480

Asp Gln Lys Ala Asp Leu Thr Lys Asp Ile Lys Thr Leu Glu Asn Asn
                485                 490                 495

Val Glu Glu Gly Leu Leu Asp Leu Ser Gly Arg Leu Ile Asp Gln Lys
                500                 505                 510

Ala Asp Ile Ala Lys Asn Gln Ala Asp Ile Ala Gln Asn Gln Thr Asp
                515                 520                 525

Ile Gln Asp Leu Ala Ala Tyr Asn Glu Leu Gln Asp Gln Tyr Ala Gln
                530                 535                 540

Lys Gln Thr Glu Ala Ile Asp Ala Leu Asn Lys Ala Ser Ser Ala Asn
545                 550                 555                 560

Thr Asp Arg Ile Ala Thr Ala Glu Leu Gly Ile Ala Glu Asn Lys Lys
                565                 570                 575

Asp Ala Gln Ile Ala Lys Ala Gln Ala Asn Glu Asn Lys Asp Gly Ile
                580                 585                 590

Ala Lys Asn Gln Ala Asp Ile Gln Leu His Asp Lys Lys Ile Thr Asn
                595                 600                 605

Leu Gly Ile Leu His Ser Met Val Ala Arg Ala Val Gly Asn Asn Thr
                610                 615                 620

Gln Gly Val Ala Thr Asn Lys Ala Asp Ile Ala Lys Asn Gln Ala Asp
625                 630                 635                 640

Ile Ala Asn Asn Ile Lys Asn Ile Tyr Glu Leu Ala Gln Gln Gln Asp
                645                 650                 655

Gln His Ser Ser Asp Ile Lys Thr Leu Ala Lys Val Ser Ala Ala Asn
                660                 665                 670

Thr Asp Arg Ile Ala Lys Asn Lys Ala Glu Ala Asp Ala Ser Phe Glu
```

```
                675                 680                 685
Thr Leu Thr Lys Asn Gln Asn Thr Leu Ile Glu Gln Gly Glu Ala Leu
    690                 695                 700

Val Glu Gln Asn Lys Ala Ile Asn Gln Glu Leu Glu Gly Phe Ala Ala
705                 710                 715                 720

His Ala Asp Val Gln Asp Lys Gln Ile Leu Gln Asn Gln Ala Asp Ile
                725                 730                 735

Thr Thr Asn Lys Ala Ala Ile Glu Gln Asn Ile Asn Arg Thr Val Ala
            740                 745                 750

Asn Gly Phe Glu Ile Glu Lys Asn Lys Ala Gly Ile Ala Thr Asn Lys
        755                 760                 765

Gln Glu Leu Ile Leu Gln Asn Asp Arg Leu Asn Gln Ile Asn Glu Thr
    770                 775                 780

Asn Asn Arg Gln Asp Gln Lys Ile Asp Gln Leu Gly Tyr Ala Leu Lys
785                 790                 795                 800

Glu Gln Gly Gln His Phe Asn Asn Arg Ile Ser Ala Val Glu Arg Gln
                805                 810                 815

Thr Ala Gly Gly Ile Ala Asn Ala Ile Ala Ile Ala Thr Leu Pro Ser
            820                 825                 830

Pro Ser Arg Ala Gly Glu His His Val Leu Phe Gly Ser Gly Tyr His
        835                 840                 845

Asn Gly Gln Ala Ala Val Ser Leu Gly Ala Ala Gly Leu Ser Asp Thr
    850                 855                 860

Gly Lys Ser Thr Tyr Lys Ile Gly Leu Ser Trp Ser Asp Ala Gly Gly
865                 870                 875                 880

Leu Ser Gly Gly Val Gly Gly Ser Tyr Arg Trp Lys
                885                 890
```

<210> SEQ ID NO 16
<211> LENGTH: 3381
<212> TYPE: DNA
<213> ORGANISM: Moraxella catarrhalis

<400> SEQUENCE: 16

```
tgtgagcaaa tgactggcgt aaatgactga tgaatgtcta tttaatgaaa gatatcaata      60
tataaaagtt gactatagcg atgcaataca gtaaaatttg ttacggctaa acataacgac     120
ggtccaagat ggcggatatc gccatttacc aacctgataa tcagtttgat agccattagc     180
gatggcatca agttgtgttg ttgtattgtc atataaacgg taaatttggt ttggtggatg     240
ccccatctga tttaccgtcc ccctaataag tgagggggg ggagacccca gtcatttatt      300
aggagactaa gatgaacaaa atttataaag tgaaaaaaaa tgccgcaggt cacttggtgg     360
catgttctga atttgccaaa ggccatacca aaaaggcagt tttgggcagt ttattgattg     420
ttggggcatt gggcatggca acgacggcgt ctgcacaagc aaccaaaggc acaggcaagc     480
acgttgttga caataaggac aacaaagcca aaggcgatta ctctaccgcc agtggtggca     540
aggacaacga agccaaaggc aattactcta ccgtcggtgg tggcgattat aacgaagcca     600
aaggcaatta ctctaccgtc ggtggtggct ctagtaatac cgccaaaggc gagaaatcaa     660
ccatcggtgg tggcgatact aacgacgcca acggcacata ctctaccatc ggtggtggct     720
attatagccg agccataggc gatagctcta ccatcggtgg tggttattat aaccaagcca     780
caggcgagaa atcaacggtt gcaggggggca ggaataacca agccacaggc aacaactcaa     840
cggttgcagg cggctcttat aaccaagcca caggcaacaa ctcaacggtt gcaggtggct     900
```

```
ctcataacca agccacaggt gaaggttcat ttgcagcagg tgtagagaac aaagccaatg    960
ccaacaacgc cgtcgctcta ggtaaaaata caccatcga tggcgataac tcagtagcca   1020
tcggctctaa taataccatt gacagtggca acaaaatgt ctttattctt ggctctagca   1080
caaacacaac aaatgcacaa agcggctccg tgctgctggg tcataatacc gctggcaaaa   1140
aagcaaccgc tgttagcagt gccaaagtga acggcttaac cctaggaaat tttgcaggtg   1200
catcaaaaac tggtaatggt actgtatctg tcggtagtga gaataatgag cgtcaaatcg   1260
tcaatgttgg tgcaggtaat atcagtgctg attcaacaga tgctgttaat ggctcacagc   1320
tatatgcttt ggccacagct gtcaaagccg atgccgatga aaactttaaa gcactcacca   1380
aaactcaaaa tactttgatt gagcaaggtg aagcacaaga cgcattaatc gctcaaaatc   1440
aaactgacat cactgccaat aaaactgcca ttgagcgaaa ttttaataga actgttgtca   1500
atgggtttga gattgagaaa aataaagctg gtattgctaa aaaccaagcg gatatccaaa   1560
cgcttgaaaa caatgtcgga gaagaactat taaatctaag cggtcgcctg cttgatcaaa   1620
aagcggatat tgataataac atcaacaata tctatgatct ggcacaacag caagatcagc   1680
atagctctga tatcaaaaca cttaaaaaaa atgtcgaaga aggtttgttg gatctaagtg   1740
gtcgcctcat tgatcaaaaa gcagatctta cgaaagacat caaaacactt gaaaacaatg   1800
tcgaagaagg tttgttggat ctaagcggtc gcctcattga tcaaaaagca gatattgcta   1860
aaaaccaagc tgacattgct caaaaccaaa cagacatcca agatctggcc gcttacaacg   1920
agctacaaga ccagtatgct caaaagcaaa ccgaagcgat tgacgctcta aataaagcaa   1980
gctctgccaa tactgatcgt attgctactg ctgaattggg tatcgctgag aacaaaaaag   2040
acgctcagat cgccaaagca caagccaatg aaaataaaga cggcattgct aaaaaccaag   2100
ctgatatcca gttgcacgat aaaaaaatca ccaatctagg tatccttcac agcatggttg   2160
caagagcggt aggaaataac acacaaggtg ttgctaccaa taaagctgac attgctaaaa   2220
accaagcaga tattgctaat aacatcaaaa atatctatga gctggcacaa cagcaagatc   2280
agcatagctc tgatatcaaa accttggcaa agtaagtgc tgccaatact gatcgtattg   2340
ctaaaaacaa agctgaagct gatgcaagtt ttgaaacgct caccaaaaat caaaatactt   2400
tgattgagca aggtgaagca ttggttgagc aaaataaagc catcaatcaa gagcttgaag   2460
ggtttgcggc tcatgcagat gttcaagata agcaaatttt acaaaaccaa gctgatatca   2520
ctaccaataa ggccgctatt gaacaaaata tcaatagaac tgttgccaat gggtttgaga   2580
ttgagaaaaa taaagctggt attgctacca ataagcaaga gcttattctt caaaatgatc   2640
gattaaatca aattaatgag acaaataatc gtcaggatca gaagattgat caattaggtt   2700
atgcactaaa agagcagggt cagcatttta taatcgtat tagtgctgtt gagcgtcaaa   2760
cagctggagg tattgcaaat gctatcgcaa ttgcaacttt accatcgccc agtagagcag   2820
gtgagcatca tgtcttattt ggttcaggtt atcacaatgg tcaagctgcg gtatcattgg   2880
gtgcggctgg gttaagtgat acaggaaaat caacttataa gattggtcta agctggtcag   2940
atgcaggtgg attatctggt ggtgttggtg gcagttaccg ctggaaatag agcctaaatt   3000
taactgctgt atcaaaaaat atggtctgta taaacagacc atattttat ctaaaaactt   3060 atcttaactt ttatgaagca tcataagcca aagctgagta ataataagag atgttaaaat   3120
aagagatgtt aaaactgcta acaatcggc ttacgacgat aaaataaaat acctggaatg   3180
gacagcccca aaaccaatgc tgagatgata aaaatcgcct caaaaaaatg acgcatcata   3240 acgataaaata aatccatatc aaatccaaaa tagccaattt gtaccatgct aaccatggct   3300
```

```
ttataggcag cgattcccgg catcatacaa atcaagctag gtacaatcaa ggctttaggc   3360
ggcaggccat gacgctgagc a                                            3381
```

<210> SEQ ID NO 17
<211> LENGTH: 170
<212> TYPE: PRT
<213> ORGANISM: Neisseria gonorrhoeae

<400> SEQUENCE: 17

```
Tyr Ala Ala Glu Arg Ile Thr His Asp Tyr Pro Lys Ala Thr Gly Ala
1               5                   10                  15

Asn Asn Thr Ser Thr Val Ser Asp Tyr Phe Arg Asn Ile Arg Ala His
            20                  25                  30

Ser Ile His Pro Arg Val Ser Val Gly Tyr Asp Phe Gly Gly Trp Arg
        35                  40                  45

Ile Ala Ala Asp Tyr Ala Ser Tyr Arg Lys Trp Lys Glu Ser Asn Ser
    50                  55                  60

Ser Thr Asn Ala Glu Asn Arg Asp Ser Ile Gln Asn Tyr Val Lys Ile
65                  70                  75                  80

Glu Thr Lys His Gln Gly Asn Gly Ser Phe His Ala Ala Ser Ser Leu
                85                  90                  95

Gly Leu Ser Ala Ile Tyr Asp Phe Lys Leu Asn Asp Lys Phe Lys Pro
            100                 105                 110

Tyr Ile Gly Ala Arg Val Ala Tyr Gly His Val Lys His Gln Val His
        115                 120                 125

Ser Val Glu Ser Lys Asn Thr Ile Ile Thr Ser Lys Pro Thr Gly Asn
    130                 135                 140

Thr Pro Ala Gly Gly Pro Val Pro Thr Gly Phe Val Pro Lys Ser Ala
145                 150                 155                 160

Tyr His Glu Ser His Ser Ile Ser Ser Leu
                165                 170
```

<210> SEQ ID NO 18
<211> LENGTH: 353
<212> TYPE: PRT
<213> ORGANISM: Haemophilus influenzae

<400> SEQUENCE: 18

```
Met Lys Lys Thr Ala Ile Ala Leu Val Val Ala Gly Leu Ala Ala Ala
1               5                   10                  15

Ser Val Ala Gln Ala Ala Pro Gln Glu Asn Thr Phe Tyr Ala Gly Val
            20                  25                  30

Lys Ala Gly Gln Ala Ser Phe His Asp Gly Leu Arg Ala Leu Ala Arg
        35                  40                  45

Glu Tyr Lys Val Gly Tyr His Arg Asn Ser Phe Thr Tyr Gly Val Phe
    50                  55                  60

Gly Gly Tyr Gln Ile Leu Asn Gln Asn Asn Leu Gly Leu Ala Val Glu
65                  70                  75                  80

Leu Gly Tyr Asp Asp Phe Gly Arg Ala Lys Gly Arg Glu Lys Gly Lys
                85                  90                  95

Thr Val Val Lys His Thr Asn His Gly Thr His Leu Ser Leu Lys Gly
            100                 105                 110

Ser Tyr Glu Val Leu Glu Gly Leu Asp Val Tyr Gly Lys Ala Gly Val
        115                 120                 125

Ala Leu Val Arg Ser Asp Tyr Lys Leu Tyr Asn Glu Asn Ser Ser Thr
```

```
                130                 135                 140
Leu Lys Lys Leu Gly Glu His His Arg Ala Arg Ala Ser Gly Leu Phe
145                 150                 155                 160

Ala Val Gly Ala Glu Tyr Ala Val Leu Pro Glu Leu Ala Val Arg Leu
                165                 170                 175

Glu Tyr Gln Trp Leu Thr Arg Val Gly Lys Tyr Arg Pro Gln Asp Lys
                180                 185                 190

Pro Asn Thr Ala Leu Asn Tyr Asn Pro Trp Ile Gly Ser Ile Asn Ala
                195                 200                 205

Gly Ile Ser Tyr Arg Phe Gly Gln Gly Ala Ala Pro Val Val Ala Ala
                210                 215                 220

Pro Glu Val Val Ser Lys Thr Phe Ser Leu Asn Ser Asp Val Thr Phe
225                 230                 235                 240

Ala Phe Gly Lys Ala Asn Leu Lys Pro Gln Ala Gln Ala Thr Leu Asp
                245                 250                 255

Ser Ile Tyr Gly Glu Met Ser Gln Val Lys Ser Ala Lys Val Ala Val
                260                 265                 270

Ala Gly Tyr Thr Asp Arg Ile Gly Ser Asp Ala Phe Asn Val Lys Leu
                275                 280                 285

Ser Gln Glu Arg Ala Asp Ser Val Ala Asn Tyr Phe Val Ala Lys Gly
                290                 295                 300

Val Ala Ala Asp Ala Ile Ser Ala Thr Gly Tyr Gly Lys Ala Asn Pro
305                 310                 315                 320

Val Thr Gly Ala Thr Cys Asp Gln Val Lys Gly Arg Lys Ala Leu Ile
                325                 330                 335

Ala Cys Phe Ala Pro Asp Arg Arg Val Glu Ile Ala Val Asn Gly Thr
                340                 345                 350

Lys

<210> SEQ ID NO 19
<211> LENGTH: 631
<212> TYPE: PRT
<213> ORGANISM: Homo sapiens

<400> SEQUENCE: 19

Pro Glu Ile Thr Gly Glu Gly Pro Pro Cys Thr Gly Cys Asn Ser
1               5                   10                  15

Cys Leu Ala Leu His Val Leu His Leu Ser Arg Ile Arg Gln Leu Thr
                20                  25                  30

Thr Glu Ser Met Pro Phe Asn Val Ala Glu Gly Lys Glu Val Leu Leu
                35                  40                  45

Leu Val His Asn Leu Pro Gln Gln Leu Phe Gly Tyr Ser Trp Tyr Lys
                50                  55                  60

Gly Glu Arg Val Asp Gly Asn Arg Gln Ile Val Gly Tyr Ala Ile Gly
65                  70                  75                  80

Thr Gln Gln Ala Thr Pro Gly Pro Ala Asn Ser Gly Arg Glu Thr Ile
                85                  90                  95

Tyr Pro Asn Ala Ser Leu Leu Ile Gln Asn Val Thr Gln Asn Asp Thr
                100                 105                 110

Gly Phe Tyr Thr Leu Gln Val Ile Lys Ser Asp Leu Val Asn Glu Glu
                115                 120                 125

Ala Thr Gly Gln Phe His Val Tyr Pro Glu Leu Pro Lys Pro Ser Ile
                130                 135                 140

Ser Ser Asn Asn Ser Asn Pro Val Glu Asp Lys Asp Ala Val Ala Phe
```

-continued

```
            145                 150                 155                 160

Thr Cys Glu Pro Glu Thr Gln Asp Thr Thr Tyr Leu Trp Trp Ile Asn
                    165                 170                 175

Asn Gln Ser Leu Pro Val Ser Pro Arg Leu Gln Leu Ser Asn Gly Asn
                180                 185                 190

Arg Thr Leu Thr Leu Ser Val Thr Arg Asn Asp Thr Gly Pro Tyr
            195                 200                 205

Glu Cys Glu Ile Gln Asn Pro Val Ser Ala Asn Arg Ser Asp Pro Val
            210                 215                 220

Thr Leu Asn Val Thr Tyr Gly Pro Asp Thr Pro Thr Ile Ser Pro Ser
225                 230                 235                 240

Asp Thr Tyr Tyr Arg Pro Gly Ala Asn Leu Ser Leu Ser Cys Tyr Ala
                    245                 250                 255

Ala Ser Asn Pro Pro Ala Gln Tyr Ser Trp Leu Ile Asn Gly Thr Phe
                260                 265                 270

Gln Gln Ser Thr Gln Glu Leu Phe Ile Pro Asn Ile Thr Val Asn Asn
            275                 280                 285

Ser Gly Ser Tyr Thr Cys His Ala Asn Asn Ser Val Thr Gly Cys Asn
            290                 295                 300

Arg Thr Thr Val Lys Thr Ile Ile Val Thr Glu Leu Ser Pro Val Val
305                 310                 315                 320

Ala Lys Pro Gln Ile Lys Ala Ser Lys Thr Thr Val Thr Gly Asp Lys
                    325                 330                 335

Asp Ser Val Asn Leu Thr Cys Ser Thr Asn Asp Thr Gly Ile Ser Ile
                340                 345                 350

Arg Trp Phe Phe Lys Asn Gln Ser Leu Pro Ser Ser Glu Arg Met Lys
            355                 360                 365

Leu Ser Gln Gly Asn Thr Thr Leu Ser Ile Asn Pro Val Lys Arg Glu
            370                 375                 380

Asp Ala Gly Thr Tyr Trp Cys Glu Val Phe Asn Pro Ile Ser Lys Asn
385                 390                 395                 400

Gln Ser Asp Pro Ile Met Leu Asn Val Glu Cys Pro Pro Cys Pro Ala
                    405                 410                 415

Pro Pro Val Ala Gly Pro Ser Val Phe Leu Phe Pro Pro Lys Pro Lys
                420                 425                 430

Asp Thr Leu Met Ile Ser Arg Thr Pro Glu Val Thr Cys Val Val Val
            435                 440                 445

Asp Val Ser His Glu Asp Pro Glu Val Lys Phe Asn Trp Tyr Val Asp
            450                 455                 460

Gly Val Glu Val His Asn Ala Lys Thr Lys Pro Arg Glu Glu Gln Tyr
465                 470                 475                 480

Asn Ser Thr Tyr Arg Val Val Ser Val Leu Thr Val Leu His Gln Asp
                    485                 490                 495

Trp Leu Asn Gly Lys Glu Tyr Lys Cys Lys Val Ser Asn Lys Gly Leu
                500                 505                 510

Pro Ser Ser Ile Glu Lys Thr Ile Ser Lys Ala Lys Gly Gln Pro Arg
            515                 520                 525

Glu Pro Gln Val Tyr Thr Leu Pro Pro Ser Arg Glu Glu Met Thr Lys
            530                 535                 540

Asn Gln Val Ser Leu Thr Cys Leu Val Lys Gly Phe Tyr Pro Ser Asp
545                 550                 555                 560

Ile Ala Val Glu Trp Glu Ser Asn Gly Gln Pro Glu Asn Asn Tyr Lys
                    565                 570                 575
```

```
Thr Thr Pro Pro Val Leu Asp Ser Asp Gly Ser Phe Phe Leu Tyr Ser
            580                 585                 590
Lys Leu Thr Val Asp Lys Ser Arg Trp Gln Gln Gly Asn Val Phe Ser
        595                 600                 605
Cys Ser Val Met His Glu Ala Leu His Asn His Tyr Thr Gln Lys Ser
    610                 615                 620
Leu Ser Leu Ser Pro Gly Lys
625                 630

<210> SEQ ID NO 20
<211> LENGTH: 1895
<212> TYPE: DNA
<213> ORGANISM: Homo sapiens

<400> SEQUENCE: 20
```

| | | | | |
|---|---|---|---|---|
| cctgagatca ccggcgaagg agggccacca tgtacaggat gcaactcctg tcttgcattg | | | | 60 |
| cactaagtct tgcacttgtc acgaattcgc agctgaccac cgagagcatg cccttcaacg | | | | 120 |
| tggccgaggg caaggaggtg ctgctgctgg tgcacaacct gccccagcag ctgttcggct | | | | 180 |
| acagctggta caagggcgag agggtggacg gcaacaggca gatcgtgggc tacgccatcg | | | | 240 |
| gcacccagca ggccaccccc ggccccgcca acagcggcag ggagaccatc taccccaacg | | | | 300 |
| ccagcctgct gatccagaac gtgacccaga cgacaccgg cttctacacc ctgcaggtga | | | | 360 |
| tcaagagcga cctggtgaac gaggaggcca ccggccagtt ccacgtgtac cccgagctgc | | | | 420 |
| ccaagcccag catcagcagc aacaacagca ccccgtgga ggacaaggac gccgtggcct | | | | 480 |
| tcacctgcga gcccgagacc aggacacca cctacctgtg gtggatcaac aaccagagcc | | | | 540 |
| tgccccgtgag ccccaggctg cagctgagca cggcaacag gaccctgacc ctgctgagcg | | | | 600 |
| tgaccaggaa cgacaccggc ccctacgagt gcgagatcca gaaccccgtg agcgccaaca | | | | 660 |
| ggagcgaccc cgtgaccctg aacgtgacct acgccccga caccccacc atcagcccca | | | | 720 |
| gcgacaccta ctacaggccc ggcgccaacc tgagcctgag ctgctacgcc gccagcaacc | | | | 780 |
| cccccgccca gtacgctgg ctgatcaacg gcaccttcca gcagagcacc caggagctgt | | | | 840 |
| tcatccccaa catcaccgtg aacaacagcg gcagctacac ctgccacgcc aacaacagcg | | | | 900 |
| tgaccggctg caacaggacc accgtgaaga ccatcatcgt gaccgagctg agccccgtgg | | | | 960 |
| tggccaagcc ccagatcaag gccagcaaga ccaccgtgac cggcgacaag acagcgtga | | | | 1020 |
| acctgacctg cagcaccaac gacaccggca tcagcatcag gtggttcttc aagaaccaga | | | | 1080 |
| gcctgcccag cagcgagagg atgaagctga gccagggcaa caccaccctg agcatcaacc | | | | 1140 |
| ccgtgaagag ggaggacgcc ggcacctact ggtgcgaggt gttcaacccc atcagcaaga | | | | 1200 |
| accagagcga cccatcatg ctgaacgtgg agtgcccacc ttgcccagca ccacctgtgg | | | | 1260 |
| caggaccttc agtcttcctc ttcccccaa acccaagga caccctcatg atctcccgga | | | | 1320 |
| cccctgaggt cacatgcgtg gtggtggacg tgagccacga agaccctgag gtcaagttca | | | | 1380 |
| actggtacgt ggacggcgtg gaggtgcata atgccaagac aaagccgcgg gaggagcagt | | | | 1440 |
| acaacagcac gtaccgtgtg gtcagcgtcc tcaccgtcct gcaccaggac tggctgaatg | | | | 1500 |
| gcaaggagta caagtgcaag gtctccaaca aaggcctccc atcctccatc gagaaaacca | | | | 1560 |
| tctccaaagc caaagggcag ccccgagaac acaggtgta ccctgcccc catcccggga | | | | 1620 |
| aggagatgac caagaaccag gtcagcctga cctgcctggt caaaggcttc tatcccagcg | | | | 1680 |
| acatcgccgt ggagtgggag agcaatgggc agccggagaa caactacaag accacgcctc | | | | 1740 |

```
ccgtgctgga ctccgacggc tccttcttcc tctacagcaa gctcaccgtg gacaagagca    1800
ggtggcagca ggggaacgtc ttctcatgct ccgtgatgca tgaggctctg cacaaccact    1860
acacgcagaa gagcctctcc ctgtctccgg gtaaa                               1895
```

```
<210> SEQ ID NO 21
<211> LENGTH: 10
<212> TYPE: PRT
<213> ORGANISM: Mus musculus

<400> SEQUENCE: 21

Trp Ile Asn Thr Tyr Thr Gly Glu Pro Thr
1               5                   10

<210> SEQ ID NO 22
<211> LENGTH: 7
<212> TYPE: PRT
<213> ORGANISM: Mus musculus
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be any naturally occurring amino acid

<400> SEQUENCE: 22

Tyr Thr Ser Xaa Leu Xaa Xaa
1               5

<210> SEQ ID NO 23
<211> LENGTH: 7
<212> TYPE: PRT
<213> ORGANISM: Mus musculus

<400> SEQUENCE: 23

Tyr Thr Ser Thr Leu Gln Pro
1               5

<210> SEQ ID NO 24
<211> LENGTH: 7
<212> TYPE: PRT
<213> ORGANISM: Mus musculus

<400> SEQUENCE: 24

Tyr Thr Ser Lys Leu His Ser
1               5

<210> SEQ ID NO 25
<211> LENGTH: 10
<212> TYPE: PRT
<213> ORGANISM: Mus musculus
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid
```

```
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be any naturally occurring amino acid

<400> SEQUENCE: 25

Gly Tyr Xaa Phe Xaa Xaa Tyr Xaa Met Xaa
1               5                   10

<210> SEQ ID NO 26
<211> LENGTH: 10
<212> TYPE: PRT
<213> ORGANISM: Mus musculus

<400> SEQUENCE: 26

Gly Tyr Thr Phe Thr Val Tyr Gly Met Asn
1               5                   10

<210> SEQ ID NO 27
<211> LENGTH: 10
<212> TYPE: PRT
<213> ORGANISM: Mus musculus

<400> SEQUENCE: 27

Gly Tyr Ile Phe Arg Asn Tyr Gly Met Lys
1               5                   10

<210> SEQ ID NO 28
<211> LENGTH: 10
<212> TYPE: PRT
<213> ORGANISM: Mus musculus

<400> SEQUENCE: 28

Gly Tyr Thr Phe Thr Thr Tyr Val Met His
1               5                   10

<210> SEQ ID NO 29
<211> LENGTH: 11
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
```

<223> OTHER INFORMATION: Xaa can be any naturally occurring amino acid

<400> SEQUENCE: 29

Xaa Ala Ser Xaa Xaa Ile Xaa Xaa Xaa Leu Xaa
1               5                   10

<210> SEQ ID NO 30
<211> LENGTH: 11
<212> TYPE: PRT
<213> ORGANISM: Mus musculus

<400> SEQUENCE: 30

Lys Ala Ser Gln Asp Ile Asn Lys Phe Leu Ala
1               5                   10

<210> SEQ ID NO 31
<211> LENGTH: 11
<212> TYPE: PRT
<213> ORGANISM: Mus musculus

<400> SEQUENCE: 31

Arg Ala Ser Gln Asp Ile Ser Asn Tyr Leu Asn
1               5                   10

<210> SEQ ID NO 32
<211> LENGTH: 11
<212> TYPE: PRT
<213> ORGANISM: Mus musculus

<400> SEQUENCE: 32

Lys Ala Ser Asp His Ile Asn Asn Trp Leu Ala
1               5                   10

<210> SEQ ID NO 33
<211> LENGTH: 10
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: Tyr or Ile
<220> FEATURE:
<221> NAME/KEY: MISC_FEATURE
<222> LOCATION: (2)..(2)
<223> OTHER INFORMATION: Arg or Thr
<220> FEATURE:
<221> NAME/KEY: MISC_FEATURE
<222> LOCATION: (3)..(3)
<223> OTHER INFORMATION: Tyr or Thr
<220> FEATURE:
<221> NAME/KEY: MISC_FEATURE
<222> LOCATION: (4)..(4)
<223> OTHER INFORMATION: Ser or Asp
<220> FEATURE:
<221> NAME/KEY: MISC_FEATURE
<222> LOCATION: (5)..(5)
<223> OTHER INFORMATION: Gly or Asn
<220> FEATURE:
<221> NAME/KEY: MISC_FEATURE
<222> LOCATION: (6)..(6)
<223> OTHER INFORMATION: Gly or Tyr
<220> FEATURE:
<221> NAME/KEY: MISC_FEATURE
<222> LOCATION: (7)..(7)
<223> OTHER INFORMATION: Met or Ala
<220> FEATURE:
<221> NAME/KEY: MISC_FEATURE
<222> LOCATION: (8)..(8)
<223> OTHER INFORMATION: Asp or Leu
<220> FEATURE:
<221> NAME/KEY: MISC_FEATURE

```
<222> LOCATION: (9)..(9)
<223> OTHER INFORMATION: Tyr or Asp
<220> FEATURE:
<221> NAME/KEY: MISC_FEATURE
<222> LOCATION: (10)..(10)
<223> OTHER INFORMATION: Asn or absent

<400> SEQUENCE: 33

Xaa Xaa Xaa Xaa Xaa Xaa Xaa Xaa Xaa Xaa
1               5                   10

<210> SEQ ID NO 34
<211> LENGTH: 9
<212> TYPE: PRT
<213> ORGANISM: Mus musculus

<400> SEQUENCE: 34

Tyr Arg Tyr Asp Gly Gly Met Asp Tyr
1               5

<210> SEQ ID NO 35
<211> LENGTH: 10
<212> TYPE: PRT
<213> ORGANISM: Mus musculus

<400> SEQUENCE: 35

Ile Thr Thr Ser Asn Tyr Ala Leu Asp Asn
1               5                   10

<210> SEQ ID NO 36
<211> LENGTH: 9
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be any naturally occurring amino acid

<400> SEQUENCE: 36

Xaa Gln Xaa Xaa Xaa Leu Xaa Xaa Xaa
1               5

<210> SEQ ID NO 37
<211> LENGTH: 8
<212> TYPE: PRT
<213> ORGANISM: Mus musculus
```

```
<400> SEQUENCE: 37

Leu Gln Tyr Asp Asn Leu Tyr Thr
1               5

<210> SEQ ID NO 38
<211> LENGTH: 9
<212> TYPE: PRT
<213> ORGANISM: Mus musculus

<400> SEQUENCE: 38

Gln Gln Gly Asn Thr Leu Pro Trp Thr
1               5

<210> SEQ ID NO 39
<211> LENGTH: 108
<212> TYPE: PRT
<213> ORGANISM: Homo sapiens

<400> SEQUENCE: 39

Gln Leu Thr Thr Glu Ser Met Pro Phe Asn Val Ala Glu Gly Lys Glu
1               5                   10                  15

Val Leu Leu Leu Val His Asn Leu Pro Gln Gln Leu Phe Gly Tyr Ser
            20                  25                  30

Trp Tyr Lys Gly Glu Arg Val Asp Gly Asn Arg Gln Ile Val Gly Tyr
        35                  40                  45

Ala Ile Gly Thr Gln Gln Ala Thr Pro Gly Pro Ala Asn Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro
            100                 105

<210> SEQ ID NO 40
<211> LENGTH: 88
<212> TYPE: PRT
<213> ORGANISM: Homo sapiens

<400> SEQUENCE: 40

Pro Lys Pro Ser Ile Ser Ser Asn Asn Ser Pro Val Glu Asp Lys
1               5                   10                  15

Asp Ala Val Ala Phe Thr Cys Glu Pro Glu Thr Gln Asp Thr Thr Tyr
            20                  25                  30

Leu Trp Trp Ile Asn Asn Gln Ser Leu Pro Val Ser Pro Arg Leu Gln
        35                  40                  45

Leu Ser Asn Gly Asn Arg Thr Leu Thr Leu Leu Ser Val Thr Arg Asn
    50                  55                  60

Asp Thr Gly Pro Tyr Glu Cys Glu Ile Gln Asn Pro Val Ser Ala Asn
65                  70                  75                  80

Arg Ser Asp Pro Val Thr Leu Asn
                85

<210> SEQ ID NO 41
<211> LENGTH: 81
<212> TYPE: PRT
<213> ORGANISM: Homo sapiens

<400> SEQUENCE: 41
```

```
Pro Asp Thr Pro Thr Ile Ser Pro Ser Asp Thr Tyr Tyr Arg Pro Gly
1               5                   10                  15

Ala Asn Leu Ser Leu Ser Cys Tyr Ala Ala Ser Asn Pro Pro Ala Gln
            20                  25                  30

Tyr Ser Trp Leu Ile Asn Gly Thr Phe Gln Gln Ser Thr Gln Glu Leu
        35                  40                  45

Phe Ile Pro Asn Ile Thr Val Asn Asn Ser Gly Ser Tyr Thr Cys His
50                  55                  60

Ala Asn Asn Ser Val Thr Gly Cys Asn Arg Thr Thr Val Lys Thr Ile
65                  70                  75                  80

Ile

<210> SEQ ID NO 42
<211> LENGTH: 91
<212> TYPE: PRT
<213> ORGANISM: Homo sapiens

<400> SEQUENCE: 42

Pro Val Val Ala Lys Pro Gln Ile Lys Ala Ser Lys Thr Thr Val Thr
1               5                   10                  15

Gly Asp Lys Asp Ser Val Asn Leu Thr Cys Ser Thr Asn Asp Thr Gly
            20                  25                  30

Ile Ser Ile Arg Trp Phe Phe Lys Asn Gln Ser Leu Pro Ser Ser Glu
        35                  40                  45

Arg Met Lys Leu Ser Gln Gly Asn Thr Thr Leu Ser Ile Asn Pro Val
50                  55                  60

Lys Arg Glu Asp Ala Gly Thr Tyr Trp Cys Glu Val Phe Asn Pro Ile
65                  70                  75                  80

Ser Lys Asn Gln Ser Asp Pro Ile Met Leu Asn
                85                  90

<210> SEQ ID NO 43
<211> LENGTH: 525
<212> TYPE: PRT
<213> ORGANISM: Homo sapiens

<400> SEQUENCE: 43

Gly His Leu Ser Ala Pro Leu His Arg Val Arg Val Pro Trp Gln Gly
1               5                   10                  15

Leu Leu Leu Thr Ala Ser Leu Leu Thr Phe Trp Asn Pro Pro Thr Thr
            20                  25                  30

Ala Gln Leu Thr Thr Glu Ser Met Pro Phe Asn Val Ala Glu Gly Lys
        35                  40                  45

Glu Val Leu Leu Leu Val His Asn Leu Pro Gln Gln Leu Phe Gly Tyr
50                  55                  60

Ser Trp Tyr Lys Gly Glu Arg Val Asp Gly Asn Arg Gln Ile Val Gly
65                  70                  75                  80

Tyr Ala Ile Gly Thr Gln Gln Ala Thr Pro Gly Pro Ala Asn Ser Gly
                85                  90                  95

Arg Glu Thr Ile Tyr Pro Asn Ala Ser Leu Leu Ile Gln Asn Val Thr
            100                 105                 110

Gln Asn Asp Thr Gly Phe Tyr Thr Leu Gln Val Ile Lys Ser Asp Leu
        115                 120                 125
```

-continued

```
Val Asn Glu Glu Ala Thr Gly Gln Phe His Val Tyr Pro Glu Leu Pro
    130                 135                 140

Lys Pro Ser Ile Ser Ser Asn Asn Ser Asn Pro Val Glu Asp Lys Asp
145                 150                 155                 160

Ala Val Ala Phe Thr Cys Glu Pro Glu Thr Gln Asp Thr Thr Tyr Leu
                165                 170                 175

Trp Trp Ile Asn Asn Gln Ser Leu Pro Val Ser Pro Arg Leu Gln Leu
                180                 185                 190

Ser Asn Gly Asn Arg Thr Leu Thr Leu Leu Ser Val Thr Arg Asn Asp
                195                 200                 205

Thr Gly Pro Tyr Glu Cys Glu Ile Gln Asn Pro Val Ser Ala Asn Arg
    210                 215                 220

Ser Asp Pro Val Thr Leu Asn Val Thr Tyr Gly Pro Asp Thr Pro Thr
225                 230                 235                 240

Ile Ser Pro Ser Asp Thr Tyr Tyr Arg Pro Gly Ala Asn Leu Ser Leu
                245                 250                 255

Ser Cys Tyr Ala Ala Ser Asn Pro Pro Ala Gln Tyr Ser Trp Leu Ile
                260                 265                 270

Asn Gly Thr Phe Gln Gln Ser Thr Gln Glu Leu Phe Ile Pro Asn Ile
                275                 280                 285

Thr Val Asn Asn Ser Gly Ser Tyr Thr Cys His Ala Asn Asn Ser Val
    290                 295                 300

Thr Gly Cys Asn Arg Thr Thr Val Lys Thr Ile Ile Val Thr Glu Leu
305                 310                 315                 320

Ser Pro Val Val Ala Lys Pro Gln Ile Lys Ala Ser Lys Thr Thr Val
                325                 330                 335

Thr Gly Asp Lys Asp Ser Val Asn Leu Thr Cys Ser Thr Asn Asp Thr
                340                 345                 350

Gly Ile Ser Ile Arg Trp Phe Phe Lys Asn Gln Ser Leu Pro Ser Ser
                355                 360                 365

Glu Arg Met Lys Leu Ser Gln Gly Asn Thr Thr Leu Ser Ile Asn Pro
    370                 375                 380

Val Lys Arg Glu Asp Ala Gly Thr Tyr Trp Cys Glu Val Phe Asn Pro
385                 390                 395                 400

Ile Ser Lys Asn Gln Ser Asp Pro Ile Met Leu Asn Val Asn Tyr Asn
                405                 410                 415

Ala Leu Pro Gln Glu Asn Gly Leu Ser Pro Gly Ala Ile Ala Gly Ile
                420                 425                 430

Val Ile Gly Val Val Ala Leu Val Ala Leu Ile Ala Val Ala Leu Ala
                435                 440                 445

Cys Phe Leu His Phe Gly Lys Thr Gly Arg Ala Ser Asp Gln Arg Asp
    450                 455                 460

Leu Thr Glu His Lys Pro Ser Val Ser Asn His Thr Gln Asp His Ser
465                 470                 475                 480

Asn Asp Pro Pro Asn Lys Met Asn Glu Val Thr Tyr Ser Thr Leu Asn
                485                 490                 495

Phe Glu Ala Gln Gln Pro Thr Gln Pro Thr Ser Ala Ser Pro Ser Leu
                500                 505                 510

Thr Ala Thr Glu Ile Ile Tyr Ser Glu Val Lys Lys Gln
                515                 520                 525
```